(12) United States Patent
Nguyen et al.

(10) Patent No.: US 8,692,064 B2
(45) Date of Patent: Apr. 8, 2014

(54) QUANTITATIVE TRAIT LOCI ASSOCIATED WITH SOYBEAN CYST NEMATODE RESISTANCE AND METHODS OF THEIR USE

(75) Inventors: Henry T. Nguyen, Columbia, MO (US); David A. Sleper, Columbia, MO (US); James G. Shannon, Kennett, MO (US); Tri D. Vuong, Columbia, MO (US); Xiaolei Wu, Cary, NC (US)

(73) Assignee: The Curators of the University of Missouri, Columbia, MO (US)

( * ) Notice: Subject to any disclaimer, the term of this patent is extended or adjusted under 35 U.S.C. 154(b) by 383 days.

(21) Appl. No.: 12/896,864

(22) Filed: Oct. 2, 2010

(65) Prior Publication Data
US 2011/0083234 A1 Apr. 7, 2011

Related U.S. Application Data

(60) Provisional application No. 61/278,233, filed on Oct. 2, 2009.

(51) Int. Cl.
*A01H 1/00* (2006.01)
*A01H 1/04* (2006.01)

(52) U.S. Cl.
USPC .......................... 800/278; 800/265; 800/260

(58) Field of Classification Search
None
See application file for complete search history.

(56) References Cited

U.S. PATENT DOCUMENTS

| | | | |
|---|---|---|---|
| 4,743,548 | A | 5/1988 | Crossway et al. |
| 4,940,838 | A | 7/1990 | Schilperoort et al. |
| 4,945,050 | A | 7/1990 | Sanford et al. |
| 5,015,580 | A | 5/1991 | Christou et al. |
| 5,149,655 | A | 9/1992 | McCabe et al. |
| 5,302,523 | A | 4/1994 | Coffee et al. |
| 5,453,367 | A | 9/1995 | Paszkowski et al. |
| 5,464,763 | A | 11/1995 | Schilperoort et al. |
| 6,096,944 | A | 8/2000 | Vierling et al. |
| 6,538,175 | B1 | 3/2003 | Webb |

OTHER PUBLICATIONS

Anand et al (Crop Sci 28: 563-564, 1988).*
Chen et al (Genome 49: 938-949, 2006).*
Anand, S.C., et al. (1988) Soybean plant introductions with resistance to races 4 or 5 of soybean cyst nematode. Crop Sci 28:563-564.
Anand, S.C. & Rao Arelli, A.P. (1989) Genetic analyses of soybean genotypes resistant to soybean cyst nematode race 5. Crop Sci 29:1181-1184.
Arelli P.R., et al. (2000) Soybean reaction to races 1 and 2 of Heterodera glycines. Crop Sci 40:824-826.
Arelli P.R.. et al. (1997) Soybean germplasm resistant to races 1 and 2 of Heterodera glycines. Crop Sci 37:1367-1369.
Arelli, P.R., et al. (2009) Inheritance of resistance in soybean PI 567516C to LY1 nematode population infecting cv. Hartwig. Euphytica 165:1-4.
Caldwell, et al. (1960) Inheritance of resistance of soybeans to the cyst nematode, Heterodera glycines. Agron J 52:635-636.
Chen, Y., et al. (2006) Molecular marker diversity of SCN-resistant sources in soybean. Genome 49:938-949.
Churchill, G.A. & Doerge, R.W. (1994) Empirical threshold values for quantitative trait mapping. Genetics 138:963-971.
Concibido, V.C., et al. (1994) DNA marker analysis of loci underlying resistance to soybean cyst nematode (Heterodera glycines Ichinohe). Crop Sci 34:240-246.
Concibido, V.C., et al. (1996) RFIP mapping and marker-assisted selection of soybean cyst nematode resistance in PI 209332. Crop Sci 36:1643-1650.
Concibido V.C., et al. (2004) A decade of QTL mapping for cyst nematode resistance in soybean. Crop Sci 44:1121-1131.
Cregan, P.B., (1999) Two simple sequences repeat markers to select for soybean cyst nematode resistance conditioned by the rhg1 locus. Theor Appl Genet 99:811-818.
Fan J, et al. (2006) Ilumina universal bead arrays, Methods in Enzymology, vol. 410 410:57-73.
Guo B. et al. (2005) Identification of QTLs associated with resistance to soybean cyst nematode races 2, 3 and 5 in soybean PI90763. Theor Appl Genet 111:965-971.
Guo B, et al. (2006b) Quantitative trait loci underlying resistance to three soybean cyst nematode populations in soybean PI 404198A. Crop Sci 46:224-233.
Hyten D, et al. (2008) High-throughput genotyping with the GoldenGate assay in the complex genome of soybean. Theor Appl Genet 116:945-952.
Mansur L.M. et al. (1993) Generation mean analysis of resistance to race-3 of soybean: lcyst nematode. Crop Sci 33:1249-1253.
Matson, A.L. & Williams, L.F. (1965) Evidence of a fourth gene for resistance to the soybean cyst nematode. Crop Sci 5:477.
Meksem K, et al. (1999) Clustering among loci underlying soybean resistance to *Fusarium solani*, SDS and SCN in near-isogenic lines. Theor Appl Genet 99:1131-1142.
Niblack, T.L., et al. (2002) A revised classification scheme for genetically diverse populations of Heterodera glycines. J Nematol 34:279-288.
Rao-Arelli, A.P. (1994) Inheritance of resistance to Heterodera glycines race 3 in soybean accessions. Plant Dis :78:898-900.
Schapaugh, W.T., et al. (1998) Registration of 'Magellan' soybean. Crop Sci 38:892.
Song, Q.J. (2004) A new integrated genetic linkage map of the soybean. Theor Appl Genet 109:122-128.
Wang D, et al. (2001) Loci underlying resistance to Race 3 of soybean cyst nematode in Glycine soja plant introduction 468916. Theor Appl Genet 103:561-566.

(Continued)

*Primary Examiner* — Shubo (Joe) Zhou
*Assistant Examiner* — Keith Robinson
(74) *Attorney, Agent, or Firm* — Lathrop & Gage LLP; Dan Cleveland, Jr.

(57) ABSTRACT

Several QTLs that are genetically linked to resistance to soybean cyst nematode (SCN) are disclosed. These QTLs have been mapped to genomic regions on Chrs. 4, 8, 10, 11, 18, and 20 of soybean, *G. max*. Candidate genes underlying these QTLs as defined by the flanking markers, as well as genetic markers associated with these QTLs are also disclosed. These markers can be utilized for introgressing SCN resistance into non-resistant soybean germplasm. The unique resistance genes can be introduced into a non-resistant plant by marker-assisted selection (MAS) or by transgenic methods.

8 Claims, 39 Drawing Sheets

(56) References Cited

OTHER PUBLICATIONS

Winter, S.M.J., et al. (2007) QTL associated with horizontal resistance to soybean cyst nematode in Glycine soja P1464925B. Theor Appl Genet 114:461-472.

Wu, X., et al. (2008) QTL, additive, and epistatic effects for SCN resistance in PI 437654. Theor Appl Genet (accepted), 13 pages.

Young, L.D. (1995) Soybean germplasm resistant to race 3, 5, and 14 of soybean cyst nematode. Crop Sci :35:895-896.

Yue P. et al., (2001a) Mapping resistance to multiple races of Heterodera glycines in soybean PI 89772 Crop Sci 41:1589-95.

Arelli PR, Young ID (2005) Genetics of resistance in soybean PI 567516C to LY1 nematode population infecting cv. Hartwig. Crop Sci Soc Am p. 234 (Abstracts).

Elliott RJ (1999) learning SAS in the computer lab (2nd Ed.) Duxbury Thomson learning, USA:39-48.

Vooriips RE (2002) MapChart: software for the graphical presentation of the linkage maps and QTLs. J Hered 93:77-78.

Webb DM, Baltazar BM, Rao-Arelli PA, Schupp J, Clayton K, Keim P, Beavis WD (1995) Genetic mapping of soybean cyst nematode race-3 resistance loci in soybean PI 437654,Theor Appl Genet 91 :574-581.

Xie M, Arelli PR, Sleper DA (1998) Genetic relationships among soybean plant introductions with resistance to Heterodera glycines using RFLP's, Soybean Genetics Newsletter, Xie continued: 25:157-163.

Young LD (1998) Heterodera glycines populations selected for reproduction on Hartwig soybean. J Nematol, 30:523.

* cited by examiner

>Glyma18g02560.1    >Glyma18g02990.1    >Glyma18g03440.1
>Glyma18g02570.1    >Glyma18g03000.1    >Glyma18g03450.1
>Glyma18g02580.1    >Glyma18g03010.1    >Glyma18g03460.1
>Glyma18g02590.1    >Glyma18g03020.1    >Glyma18g03470.1
>Glyma18g02600.1    >Glyma18g03030.1    >Glyma18g03480.1
>Glyma18g02610.1    >Glyma18g03040.1    >Glyma18g03490.1
>Glyma18g02620.1    >Glyma18g03050.1    >Glyma18g03500.1
>Glyma18g02630.1    >Glyma18g03060.1    >Glyma18g03510.1
>Glyma18g02640.1    >Glyma18g03070.1    >Glyma18g03520.1
>Glyma18g02650.1    >Glyma18g03080.1    >Glyma18g03530.1
>Glyma18g02650.2    >Glyma18g03090.1    >Glyma18g03540.1
>Glyma18g02660.1    >Glyma18g03100.1    >Glyma18g03550.1
>Glyma18g02670.1    >Glyma18g03110.1    >Glyma18g03560.1
>Glyma18g02680.1    >Glyma18g03120.1    >Glyma18g03570.1
>Glyma18g02690.1    >Glyma18g03130.1    >Glyma18g03580.1
>Glyma18g02700.1    >Glyma18g03140.1    >Glyma18g03590.1
>Glyma18g02710.1    >Glyma18g03150.1    >Glyma18g03600.1
>Glyma18g02720.1    >Glyma18g03160.1    >Glyma18g03610.1
>Glyma18g02730.1    >Glyma18g03170.1    >Glyma18g03620.1
>Glyma18g02740.1    >Glyma18g03180.1    >Glyma18g03630.1
>Glyma18g02750.1    >Glyma18g03190.1    >Glyma18g03640.1
>Glyma18g02760.1    >Glyma18g03200.1    >Glyma18g03640.2
>Glyma18g02770.1    >Glyma18g03210.1    >Glyma18g03650.1
>Glyma18g02780.1    >Glyma18g03220.1    >Glyma18g03660.1
>Glyma18g02790.1    >Glyma18g03220.2    >Glyma18g03670.1
>Glyma18g02800.1    >Glyma18g03230.1    >Glyma18g03680.1
>Glyma18g02800.2    >Glyma18g03240.1    >Glyma18g03690.1
>Glyma18g02810.1    >Glyma18g03250.1    >Glyma18g03700.1
>Glyma18g02820.1    >Glyma18g03260.1    >Glyma18g03710.1
>Glyma18g02830.1    >Glyma18g03270.1    >Glyma18g03720.1
>Glyma18g02840.1    >Glyma18g03280.1    >Glyma18g03730.1
>Glyma18g02850.1    >Glyma18g03290.1    >Glyma18g03740.1
>Glyma18g02860.1    >Glyma18g03300.1    >Glyma18g03750.1
>Glyma18g02870.1    >Glyma18g03310.1    >Glyma18g03760.1
>Glyma18g02880.1    >Glyma18g03320.1    >Glyma18g03770.1
>Glyma18g02890.1    >Glyma18g03330.1    >Glyma18g03780.1
>Glyma18g02900.1    >Glyma18g03340.1    >Glyma18g03790.1
>Glyma18g02910.1    >Glyma18g03350.1    >Glyma18g03800.1
>Glyma18g02920.1    >Glyma18g03360.1    >Glyma18g03810.1
>Glyma18g02930.1    >Glyma18g03370.1    >Glyma18g03820.1
>Glyma18g02940.1    >Glyma18g03380.1    >Glyma18g03830.1
>Glyma18g02950.1    >Glyma18g03390.1    >Glyma18g03840.1
>Glyma18g02960.1    >Glyma18g03400.1    >Glyma18g03850.1
>Glyma18g02970.1    >Glyma18g03420.1    >Glyma18g03860.1
>Glyma18g02980.1    >Glyma18g03430.1

FIG. 1

>Glyma08g12490.1
>Glyma08g12500.1
>Glyma08g12510.1
>Glyma08g12520.1
>Glyma08g12520.2
>Glyma08g12530.1
>Glyma08g12540.1
>Glyma08g12550.1
>Glyma08g12560.1
>Glyma08g12560.2
>Glyma08g12560.3
>Glyma08g12570.1
>Glyma08g12580.1
>Glyma08g12590.1
>Glyma08g12600.1
>Glyma08g12610.1
>Glyma08g12620.1
>Glyma08g12630.1
>Glyma08g12640.1
>Glyma08g12650.1
>Glyma08g12650.2
>Glyma08g12650.3
>Glyma08g12660.1
>Glyma08g12670.1
>Glyma08g12680.1
>Glyma08g12690.1
>Glyma08g12700.1
>Glyma08g12710.1
>Glyma08g12720.1
>Glyma08g12730.1
>Glyma08g12740.1
>Glyma08g12750.1
>Glyma08g12760.1
>Glyma08g12770.1
>Glyma08g12780.1
>Glyma08g12790.1
>Glyma08g12800.1
>Glyma08g12810.1
>Glyma08g12820.1
>Glyma08g12820.2
>Glyma08g12830.1
>Glyma08g12840.1
>Glyma08g12850.1
>Glyma08g12860.1
>Glyma08g12870.1

>Glyma08g12880.1
>Glyma08g12890.1
>Glyma08g12900.1
>Glyma08g12900.2
>Glyma08g12910.1
>Glyma08g12920.1
>Glyma08g12930.1
>Glyma08g12940.1
>Glyma08g12940.2
>Glyma08g12950.1
>Glyma08g12960.1
>Glyma08g12970.1
>Glyma08g12980.1
>Glyma08g12980.2
>Glyma08g12990.1
>Glyma08g13000.1
>Glyma08g13010.1
>Glyma08g13020.1
>Glyma08g13030.1
>Glyma08g13040.1
>Glyma08g13040.2
>Glyma08g13050.1
>Glyma08g13060.1
>Glyma08g13070.1
>Glyma08g13080.1
>Glyma08g13090.1
>Glyma08g13090.2
>Glyma08g13100.1
>Glyma08g13110.1
>Glyma08g13110.2
>Glyma08g13120.1
>Glyma08g13130.1
>Glyma08g13130.2
>Glyma08g13140.1
>Glyma08g13150.1
>Glyma08g13160.1
>Glyma08g13170.1
>Glyma08g13180.1
>Glyma08g13180.2
>Glyma08g13190.1
>Glyma08g13200.1
>Glyma08g13210.1
>Glyma08g13220.1
>Glyma08g13220.2
>Glyma08g13230.1

>Glyma08g13240.1
>Glyma08g13240.2
>Glyma08g13240.3
>Glyma08g13250.1
>Glyma08g13260.1
>Glyma08g13270.1
>Glyma08g13280.1
>Glyma08g13290.1
>Glyma08g13300.1
>Glyma08g13300.2
>Glyma08g13300.3
>Glyma08g13300.4
>Glyma08g13310.1
>Glyma08g13320.1
>Glyma08g13330.1
>Glyma08g13340.1
>Glyma08g13340.2
>Glyma08g13350.1
>Glyma08g13360.1
>Glyma08g13370.1
>Glyma08g13380.1
>Glyma08g13390.1
>Glyma08g13400.1
>Glyma08g13410.1
>Glyma08g13420.1
>Glyma08g13430.1
>Glyma08g13440.1
>Glyma08g13440.2
>Glyma08g13450.1
>Glyma08g13450.2
>Glyma08g13460.1
>Glyma08g13470.1
>Glyma08g13480.1
>Glyma08g13490.1
>Glyma08g13500.1
>Glyma08g13510.1
>Glyma08g13520.1
>Glyma08g13520.2
>Glyma08g13530.1
>Glyma08g13540.1
>Glyma08g13550.1
>Glyma08g13560.1
>Glyma08g13560.2
>Glyma08g13570.1
>Glyma08g13580.1

FIG. 2

>Glyma08g13590.1
>Glyma08g13600.1
>Glyma08g13610.1
>Glyma08g13620.1
>Glyma08g13630.1
>Glyma08g13630.2
>Glyma08g13640.1
>Glyma08g13650.1
>Glyma08g13660.1
>Glyma08g13670.1
>Glyma08g13680.1
>Glyma08g13690.1
>Glyma08g13700.1
>Glyma08g13720.1
>Glyma08g13730.1
>Glyma08g13740.1
>Glyma08g13740.2
>Glyma08g13740.3
>Glyma08g13740.4
>Glyma08g13750.1
>Glyma08g13760.1
>Glyma08g13770.1
>Glyma08g13780.1
>Glyma08g13790.1
>Glyma08g13800.1
>Glyma08g13810.1
>Glyma08g13820.1
>Glyma08g13830.1
>Glyma08g13840.1
>Glyma08g13850.1
>Glyma08g13860.1
>Glyma08g13870.1
>Glyma08g13880.1
>Glyma08g13890.1
>Glyma08g13900.1
>Glyma08g13910.1
>Glyma08g13910.2
>Glyma08g13910.3
>Glyma08g13920.1
>Glyma08g13930.1
>Glyma08g13930.2
>Glyma08g13940.1
>Glyma08g13950.1
>Glyma08g13960.1
>Glyma08g13970.1

>Glyma08g13980.1
>Glyma08g13980.2
>Glyma08g13990.1
>Glyma08g14000.1
>Glyma08g14010.1
>Glyma08g14020.1
>Glyma08g14030.1
>Glyma08g14040.1
>Glyma08g14050.1
>Glyma08g14060.1
>Glyma08g14070.1
>Glyma08g14080.1
>Glyma08g14090.1
>Glyma08g14100.1
>Glyma08g14110.1
>Glyma08g14120.1
>Glyma08g14130.1
>Glyma08g14130.2
>Glyma08g14140.1
>Glyma08g14150.1
>Glyma08g14160.1
>Glyma08g14170.1
>Glyma08g14180.1
>Glyma08g14190.1
>Glyma08g14200.1
>Glyma08g14210.1
>Glyma08g14220.1
>Glyma08g14230.1
>Glyma08g14240.1
>Glyma08g14250.1
>Glyma08g14250.2
>Glyma08g14260.1
>Glyma08g14270.1
>Glyma08g14280.1
>Glyma08g14280.2
>Glyma08g14280.3
>Glyma08g14280.4
>Glyma08g14280.5
>Glyma08g14290.1
>Glyma08g14300.1
>Glyma08g14310.1
>Glyma08g14320.1
>Glyma08g14330.1
>Glyma08g14340.1
>Glyma08g14350.1

>Glyma08g14360.1
>Glyma08g14370.1
>Glyma08g14380.1
>Glyma08g14390.1
>Glyma08g14400.1
>Glyma08g14410.1
>Glyma08g14420.1
>Glyma08g14430.1
>Glyma08g14440.1
>Glyma08g14440.2
>Glyma08g14440.3
>Glyma08g14440.4
>Glyma08g14440.5
>Glyma08g14440.6
>Glyma08g14450.1
>Glyma08g14450.2
>Glyma08g14460.1
>Glyma08g14460.2
>Glyma08g14460.3
>Glyma08g14470.1
>Glyma08g14480.1
>Glyma08g14490.1
>Glyma08g14500.1
>Glyma08g14510.1
>Glyma08g14520.1
>Glyma08g14530.1
>Glyma08g14540.1
>Glyma08g14550.1
>Glyma08g14560.1
>Glyma08g14570.1
>Glyma08g14580.1
>Glyma08g14590.1
>Glyma08g14590.2
>Glyma08g14600.1
>Glyma08g14610.1
>Glyma08g14620.1
>Glyma08g14630.1
>Glyma08g14640.1
>Glyma08g14650.1
>Glyma08g14660.1
>Glyma08g14670.1
>Glyma08g14670.2
>Glyma08g14670.3

FIG. 2 (cont.)

>Glyma08g14680.1　　　　>Glyma08g14950.1　　　　>Glyma08g15280.1
>Glyma08g14680.2　　　　>Glyma08g14960.1　　　　>Glyma08g15290.1
>Glyma08g14690.1　　　　>Glyma08g14970.1　　　　>Glyma08g15300.1
>Glyma08g14700.1　　　　>Glyma08g14980.1　　　　>Glyma08g15310.1
>Glyma08g14710.1　　　　>Glyma08g14980.2　　　　>Glyma08g15310.2
>Glyma08g14720.1　　　　>Glyma08g14990.1　　　　>Glyma08g15320.1
>Glyma08g14720.2　　　　>Glyma08g15000.1　　　　>Glyma08g15330.1
>Glyma08g14720.3　　　　>Glyma08g15000.2　　　　>Glyma08g15340.1
>Glyma08g14730.1　　　　>Glyma08g15000.3　　　　>Glyma08g15350.1
>Glyma08g14740.1　　　　>Glyma08g15000.4　　　　>Glyma08g15360.1
>Glyma08g14740.2　　　　>Glyma08g15000.5　　　　>Glyma08g15370.1
>Glyma08g14750.1　　　　>Glyma08g15000.6　　　　>Glyma08g15370.2
>Glyma08g14750.2　　　　>Glyma08g15010.1　　　　>Glyma08g15370.3
>Glyma08g14750.3　　　　>Glyma08g15010.2　　　　>Glyma08g15370.4
>Glyma08g14760.1　　　　>Glyma08g15020.1　　　　>Glyma08g15380.1
>Glyma08g14770.1　　　　>Glyma08g15030.1　　　　>Glyma08g15390.1
>Glyma08g14780.1　　　　>Glyma08g15040.1　　　　>Glyma08g15400.1
>Glyma08g14780.2　　　　>Glyma08g15050.1　　　　>Glyma08g15410.1
>Glyma08g14790.1　　　　>Glyma08g15060.1　　　　>Glyma08g15420.1
>Glyma08g14790.2　　　　>Glyma08g15070.1　　　　>Glyma08g15430.1
>Glyma08g14800.1　　　　>Glyma08g15080.1　　　　>Glyma08g15440.1
>Glyma08g14810.1　　　　>Glyma08g15090.1　　　　>Glyma08g15450.1
>Glyma08g14820.1　　　　>Glyma08g15090.2　　　　>Glyma08g15460.1
>Glyma08g14830.1　　　　>Glyma08g15100.1　　　　>Glyma08g15460.2
>Glyma08g14830.2　　　　>Glyma08g15100.2　　　　>Glyma08g15460.3
>Glyma08g14830.3　　　　>Glyma08g15110.1　　　　>Glyma08g15470.1
>Glyma08g14830.4　　　　>Glyma08g15120.1　　　　>Glyma08g15480.1
>Glyma08g14830.5　　　　>Glyma08g15130.1　　　　>Glyma08g15490.1
>Glyma08g14830.6　　　　>Glyma08g15140.1　　　　>Glyma08g15500.1
>Glyma08g14840.1　　　　>Glyma08g15150.1　　　　>Glyma08g15510.1
>Glyma08g14840.2　　　　>Glyma08g15160.1　　　　>Glyma08g15520.1
>Glyma08g14850.1　　　　>Glyma08g15170.1　　　　>Glyma08g15530.1
>Glyma08g14850.2　　　　>Glyma08g15180.1　　　　>Glyma08g15540.1
>Glyma08g14860.1　　　　>Glyma08g15210.1　　　　>Glyma08g15550.1
>Glyma08g14870.1　　　　>Glyma08g15210.2　　　　>Glyma08g15560.1
>Glyma08g14880.1　　　　>Glyma08g15210.3　　　　>Glyma08g15570.1
>Glyma08g14890.1　　　　>Glyma08g15220.1　　　　>Glyma08g15580.1
>Glyma08g14900.1　　　　>Glyma08g15230.1　　　　>Glyma08g15590.1
>Glyma08g14910.1　　　　>Glyma08g15240.1　　　　>Glyma08g15600.1
>Glyma08g14920.1　　　　>Glyma08g15250.1　　　　>Glyma08g15610.1
>Glyma08g14930.1　　　　>Glyma08g15260.1　　　　>Glyma08g15620.1
>Glyma08g14940.1　　　　>Glyma08g15270.1　　　　>Glyma08g15630.1
>Glyma08g14940.2　　　　>Glyma08g15270.2　　　　>Glyma08g15640.1

FIG. 2 (cont.)

>Glyma08g15650.1
>Glyma08g15660.1
>Glyma08g15670.1
>Glyma08g15680.1
>Glyma08g15690.1
>Glyma08g15700.1
>Glyma08g15730.1
>Glyma08g15740.1
>Glyma08g15740.2
>Glyma08g15750.1
>Glyma08g15760.1
>Glyma08g15780.1
>Glyma08g15790.1
>Glyma08g15800.1
>Glyma08g15810.1
>Glyma08g15820.1
>Glyma08g15830.1
>Glyma08g15840.1
>Glyma08g15850.1
>Glyma08g15860.1
>Glyma08g15870.1
>Glyma08g15880.1
>Glyma08g15890.1
>Glyma08g15910.1
>Glyma08g15920.1
>Glyma08g15930.1
>Glyma08g15940.1
>Glyma08g15950.1
>Glyma08g15960.1
>Glyma08g15960.2
>Glyma08g15970.1
>Glyma08g15980.1
>Glyma08g15990.1
>Glyma08g16000.1
>Glyma08g16010.1
>Glyma08g16020.1
>Glyma08g16020.2
>Glyma08g16020.3
>Glyma08g16030.1
>Glyma08g16040.1
>Glyma08g16050.1
>Glyma08g16060.1
>Glyma08g16070.1

>Glyma08g16080.1
>Glyma08g16090.1
>Glyma08g16100.1
>Glyma08g16110.1
>Glyma08g16120.1
>Glyma08g16130.1
>Glyma08g16130.2
>Glyma08g16130.3
>Glyma08g16140.1
>Glyma08g16150.1
>Glyma08g16160.1
>Glyma08g16170.1
>Glyma08g16180.1
>Glyma08g16190.1
>Glyma08g16200.1
>Glyma08g16210.1
>Glyma08g16220.1
>Glyma08g16230.1
>Glyma08g16240.1
>Glyma08g16250.1

FIG. 2 (cont.)

>Glyma11g34400.1
>Glyma11g34410.1
>Glyma11g34420.1
>Glyma11g34430.1
>Glyma11g34440.1
>Glyma11g34450.1
>Glyma11g34460.1
>Glyma11g34460.2
>Glyma11g34470.1
>Glyma11g34470.2
>Glyma11g34480.1
>Glyma11g34490.1
>Glyma11g34500.1
>Glyma11g34510.1
>Glyma11g34520.1
>Glyma11g34530.1
>Glyma11g34540.1
>Glyma11g34550.1
>Glyma11g34560.1
>Glyma11g34570.1
>Glyma11g34580.1
>Glyma11g34590.1
>Glyma11g34600.1
>Glyma11g34610.1
>Glyma11g34620.1
>Glyma11g34630.1
>Glyma11g34640.1
>Glyma11g34650.1
>Glyma11g34660.1
>Glyma11g34670.1
>Glyma11g34680.1
>Glyma11g34690.1
>Glyma11g34700.1
>Glyma11g34700.2
>Glyma11g34710.1
>Glyma11g34720.1
>Glyma11g34730.1
>Glyma11g34740.1
>Glyma11g34750.1
>Glyma11g34760.1
>Glyma11g34770.1
>Glyma11g34780.1
>Glyma11g34790.1
>Glyma11g34790.2
>Glyma11g34800.1
>Glyma11g34800.2
>Glyma11g34810.1

>Glyma11g34820.1
>Glyma11g34830.1
>Glyma11g34830.2
>Glyma11g34830.3
>Glyma11g34830.4
>Glyma11g34830.5
>Glyma11g34840.1
>Glyma11g34850.1
>Glyma11g34860.1
>Glyma11g34870.1
>Glyma11g34870.2
>Glyma11g34880.1
>Glyma11g34890.1
>Glyma11g34900.1
>Glyma11g34910.1
>Glyma11g34920.1
>Glyma11g34930.1
>Glyma11g34930.2
>Glyma11g34930.3
>Glyma11g34930.4
>Glyma11g34940.1
>Glyma11g34950.1
>Glyma11g34950.2
>Glyma11g34960.1
>Glyma11g34970.1
>Glyma11g34980.1
>Glyma11g34990.1
>Glyma11g35000.1
>Glyma11g35010.1
>Glyma11g35020.1
>Glyma11g35020.2
>Glyma11g35030.1
>Glyma11g35040.1
>Glyma11g35050.1
>Glyma11g35060.1
>Glyma11g35070.1
>Glyma11g35080.1
>Glyma11g35090.1
>Glyma11g35100.1
>Glyma11g35110.1
>Glyma11g35110.2
>Glyma11g35120.1
>Glyma11g35130.1
>Glyma11g35140.1
>Glyma11g35150.1
>Glyma11g35160.1
>Glyma11g35170.1

>Glyma11g35180.1
>Glyma11g35190.1
>Glyma11g35200.1
>Glyma11g35210.1
>Glyma11g35220.1
>Glyma11g35230.1
>Glyma11g35240.1
>Glyma11g35240.2
>Glyma11g35250.1
>Glyma11g35260.1
>Glyma11g35260.2
>Glyma11g35270.1
>Glyma11g35280.1
>Glyma11g35290.1
>Glyma11g35300.1
>Glyma11g35310.1
>Glyma11g35320.1
>Glyma11g35330.1
>Glyma11g35340.1
>Glyma11g35350.1
>Glyma11g35360.1
>Glyma11g35370.1
>Glyma11g35380.1
>Glyma11g35390.1
>Glyma11g35400.1
>Glyma11g35410.1
>Glyma11g35420.1
>Glyma11g35430.1
>Glyma11g35440.1
>Glyma11g35450.1
>Glyma11g35450.2
>Glyma11g35450.3
>Glyma11g35450.4
>Glyma11g35460.1
>Glyma11g35470.1
>Glyma11g35480.1
>Glyma11g35490.1
>Glyma11g35500.1
>Glyma11g35510.1
>Glyma11g35520.1
>Glyma11g35530.1
>Glyma11g35540.1
>Glyma11g35540.2
>Glyma11g35550.1
>Glyma11g35560.1
>Glyma11g35570.1
>Glyma11g35580.1

FIG. 3

>Glyma11g35590.1
>Glyma11g35600.1
>Glyma11g35610.1
>Glyma11g35620.1
>Glyma11g35630.1
>Glyma11g35640.1
>Glyma11g35650.1
>Glyma11g35660.1
>Glyma11g35670.1
>Glyma11g35680.1
>Glyma11g35690.1
>Glyma11g35700.1
>Glyma11g35710.1
>Glyma11g35720.1
>Glyma11g35730.1
>Glyma11g35740.1
>Glyma11g35740.2
>Glyma11g35740.3
>Glyma11g35740.4
>Glyma11g35740.5
>Glyma11g35750.1
>Glyma11g35760.1
>Glyma11g35770.1
>Glyma11g35780.1
>Glyma11g35790.1
>Glyma11g35790.2
>Glyma11g35800.1
>Glyma11g35810.1
>Glyma11g35820.1
>Glyma11g35830.1
>Glyma11g35840.1
>Glyma11g35850.1
>Glyma11g35860.1
>Glyma11g35870.1
>Glyma11g35880.1
>Glyma11g35890.1
>Glyma11g35900.1
>Glyma11g35910.1
>Glyma11g35920.1
>Glyma11g35930.1
>Glyma11g35940.1
>Glyma11g35950.1
>Glyma11g35960.1
>Glyma11g35970.1
>Glyma11g35980.1

>Glyma11g35990.1
>Glyma11g36000.1
>Glyma11g36000.2
>Glyma11g36000.3
>Glyma11g36010.1
>Glyma11g36010.2
>Glyma11g36020.1
>Glyma11g36030.1
>Glyma11g36040.1
>Glyma11g36050.1
>Glyma11g36060.1
>Glyma11g36070.1
>Glyma11g36080.1
>Glyma11g36080.2
>Glyma11g36090.1
>Glyma11g36100.1
>Glyma11g36110.1
>Glyma11g36120.1
>Glyma11g36130.1
>Glyma11g36140.1
>Glyma11g36150.1
>Glyma11g36160.1
>Glyma11g36170.1
>Glyma11g36170.2
>Glyma11g36180.1
>Glyma11g36190.1
>Glyma11g36200.1
>Glyma11g36210.1
>Glyma11g36220.1
>Glyma11g36230.1
>Glyma11g36240.1
>Glyma11g36250.1
>Glyma11g36260.1
>Glyma11g36270.1
>Glyma11g36290.1
>Glyma11g36300.1
>Glyma11g36390.1
>Glyma11g36400.1
>Glyma11g36410.1
>Glyma11g36420.1
>Glyma11g36430.1
>Glyma11g36440.1
>Glyma11g36440.2
>Glyma11g36460.1
>Glyma11g36470.1

>Glyma11g36480.1
>Glyma11g36490.1
>Glyma11g36500.1
>Glyma11g36510.1
>Glyma11g36520.1
>Glyma11g36530.1
>Glyma11g36540.1
>Glyma11g36540.2
>Glyma11g36550.1
>Glyma11g36560.1
>Glyma11g36570.1
>Glyma11g36580.1
>Glyma11g36590.1
>Glyma11g36600.1
>Glyma11g36610.1
>Glyma11g36620.1
>Glyma11g36630.1
>Glyma11g36640.1
>Glyma11g36650.1
>Glyma11g36660.1
>Glyma11g36670.1
>Glyma11g36680.1
>Glyma11g36690.1
>Glyma11g36700.1
>Glyma11g36710.1
>Glyma11g36720.1
>Glyma11g36730.1
>Glyma11g36740.1
>Glyma11g36750.1
>Glyma11g36760.1
>Glyma11g36770.1
>Glyma11g36770.2
>Glyma11g36780.1
>Glyma11g36790.1
>Glyma11g36800.1
>Glyma11g36810.1
>Glyma11g36820.1
>Glyma11g36830.1
>Glyma11g36840.1
>Glyma11g36840.2
>Glyma11g36850.1
>Glyma11g36860.1
>Glyma11g36870.1
>Glyma11g36880.1
>Glyma11g36890.1

FIG. 3 (cont.)

| | | |
|---|---|---|
| >Glyma11g36890.2 | >Glyma11g37200.1 | >Glyma11g37550.1 |
| >Glyma11g36890.3 | >Glyma11g37210.1 | >Glyma11g37560.1 |
| >Glyma11g36890.4 | >Glyma11g37210.2 | >Glyma11g37570.1 |
| >Glyma11g36900.1 | >Glyma11g37210.3 | >Glyma11g37580.1 |
| >Glyma11g36900.2 | >Glyma11g37220.1 | >Glyma11g37590.1 |
| >Glyma11g36900.3 | >Glyma11g37230.1 | >Glyma11g37600.1 |
| >Glyma11g36910.1 | >Glyma11g37240.1 | >Glyma11g37610.1 |
| >Glyma11g36920.1 | >Glyma11g37250.1 | >Glyma11g37620.1 |
| >Glyma11g36930.1 | >Glyma11g37250.2 | >Glyma11g37630.1 |
| >Glyma11g36940.1 | >Glyma11g37260.1 | >Glyma11g37630.2 |
| >Glyma11g36950.1 | >Glyma11g37270.1 | >Glyma11g37650.1 |
| >Glyma11g36950.2 | >Glyma11g37280.1 | >Glyma11g37660.1 |
| >Glyma11g36950.3 | >Glyma11g37290.1 | |
| >Glyma11g36960.1 | >Glyma11g37300.1 | |
| >Glyma11g36970.1 | >Glyma11g37310.1 | |
| >Glyma11g36980.1 | >Glyma11g37320.1 | |
| >Glyma11g36980.2 | >Glyma11g37330.1 | |
| >Glyma11g36990.1 | >Glyma11g37330.2 | |
| >Glyma11g36990.2 | >Glyma11g37330.3 | |
| >Glyma11g36990.3 | >Glyma11g37340.1 | |
| >Glyma11g37000.1 | >Glyma11g37350.1 | |
| >Glyma11g37010.1 | >Glyma11g37360.1 | |
| >Glyma11g37020.1 | >Glyma11g37370.1 | |
| >Glyma11g37030.1 | >Glyma11g37380.1 | |
| >Glyma11g37040.1 | >Glyma11g37380.2 | |
| >Glyma11g37050.1 | >Glyma11g37380.3 | |
| >Glyma11g37060.1 | >Glyma11g37390.1 | |
| >Glyma11g37070.1 | >Glyma11g37400.1 | |
| >Glyma11g37080.1 | >Glyma11g37410.1 | |
| >Glyma11g37090.1 | >Glyma11g37420.1 | |
| >Glyma11g37100.1 | >Glyma11g37430.1 | |
| >Glyma11g37100.2 | >Glyma11g37440.1 | |
| >Glyma11g37100.3 | >Glyma11g37440.2 | |
| >Glyma11g37110.1 | >Glyma11g37450.1 | |
| >Glyma11g37120.1 | >Glyma11g37460.1 | |
| >Glyma11g37130.1 | >Glyma11g37470.1 | |
| >Glyma11g37140.1 | >Glyma11g37480.1 | |
| >Glyma11g37150.1 | >Glyma11g37490.1 | |
| >Glyma11g37150.2 | >Glyma11g37500.1 | |
| >Glyma11g37150.3 | >Glyma11g37500.2 | |
| >Glyma11g37150.4 | >Glyma11g37500.3 | |
| >Glyma11g37160.1 | >Glyma11g37510.1 | |
| >Glyma11g37170.1 | >Glyma11g37520.1 | |
| >Glyma11g37180.1 | >Glyma11g37530.1 | |
| >Glyma11g37190.1 | >Glyma11g37540.1 | |

FIG. 3 (cont.)

| | | |
|---|---|---|
| >Glyma20g33290.1 | >Glyma20g33760.1 | >Glyma20g34220.1 |
| >Glyma20g33300.1 | >Glyma20g33770.1 | >Glyma20g34230.1 |
| >Glyma20g33310.1 | >Glyma20g33780.1 | >Glyma20g34240.1 |
| >Glyma20g33320.1 | >Glyma20g33790.1 | >Glyma20g34250.1 |
| >Glyma20g33330.1 | >Glyma20g33800.1 | >Glyma20g34260.1 |
| >Glyma20g33340.1 | >Glyma20g33810.1 | >Glyma20g34270.1 |
| >Glyma20g33350.1 | >Glyma20g33820.1 | >Glyma20g34280.1 |
| >Glyma20g33350.2 | >Glyma20g33830.1 | >Glyma20g34290.1 |
| >Glyma20g33360.1 | >Glyma20g33840.1 | >Glyma20g34290.2 |
| >Glyma20g33370.1 | >Glyma20g33850.1 | >Glyma20g34290.3 |
| >Glyma20g33380.1 | >Glyma20g33860.1 | >Glyma20g34300.1 |
| >Glyma20g33390.1 | >Glyma20g33870.1 | >Glyma20g34310.1 |
| >Glyma20g33400.1 | >Glyma20g33880.1 | >Glyma20g34320.1 |
| >Glyma20g33420.1 | >Glyma20g33890.1 | >Glyma20g34330.1 |
| >Glyma20g33430.1 | >Glyma20g33900.1 | >Glyma20g34340.1 |
| >Glyma20g33440.1 | >Glyma20g33910.1 | >Glyma20g34350.1 |
| >Glyma20g33450.1 | >Glyma20g33920.1 | >Glyma20g34360.1 |
| >Glyma20g33460.1 | >Glyma20g33930.1 | >Glyma20g34370.1 |
| >Glyma20g33470.1 | >Glyma20g33940.1 | >Glyma20g34380.1 |
| >Glyma20g33480.1 | >Glyma20g33950.1 | >Glyma20g34390.1 |
| >Glyma20g33490.1 | >Glyma20g33960.1 | >Glyma20g34400.1 |
| >Glyma20g33500.1 | >Glyma20g33970.1 | >Glyma20g34410.1 |
| >Glyma20g33510.1 | >Glyma20g33980.1 | >Glyma20g34410.2 |
| >Glyma20g33520.1 | >Glyma20g33990.1 | >Glyma20g34420.1 |
| >Glyma20g33530.1 | >Glyma20g34000.1 | >Glyma20g34420.2 |
| >Glyma20g33540.1 | >Glyma20g34000.2 | >Glyma20g34430.1 |
| >Glyma20g33550.1 | >Glyma20g34010.1 | >Glyma20g34440.1 |
| >Glyma20g33560.1 | >Glyma20g34020.1 | >Glyma20g34450.1 |
| >Glyma20g33560.2 | >Glyma20g34030.1 | >Glyma20g34460.1 |
| >Glyma20g33570.1 | >Glyma20g34040.1 | >Glyma20g34470.1 |
| >Glyma20g33580.1 | >Glyma20g34050.1 | >Glyma20g34480.1 |
| >Glyma20g33590.1 | >Glyma20g34060.1 | >Glyma20g34490.1 |
| >Glyma20g33600.1 | >Glyma20g34070.1 | >Glyma20g34500.1 |
| >Glyma20g33610.1 | >Glyma20g34080.1 | >Glyma20g34500.2 |
| >Glyma20g33620.1 | >Glyma20g34090.1 | >Glyma20g34510.1 |
| >Glyma20g33630.1 | >Glyma20g34100.1 | >Glyma20g34520.1 |
| >Glyma20g33640.1 | >Glyma20g34110.1 | >Glyma20g34520.2 |
| >Glyma20g33650.1 | >Glyma20g34110.2 | >Glyma20g34530.1 |
| >Glyma20g33660.1 | >Glyma20g34120.1 | >Glyma20g34540.1 |
| >Glyma20g33670.1 | >Glyma20g34130.1 | >Glyma20g34550.1 |
| >Glyma20g33680.1 | >Glyma20g34140.1 | >Glyma20g34560.1 |
| >Glyma20g33690.1 | >Glyma20g34150.1 | >Glyma20g34570.1 |
| >Glyma20g33700.1 | >Glyma20g34160.1 | >Glyma20g34580.1 |
| >Glyma20g33710.1 | >Glyma20g34170.1 | >Glyma20g34590.1 |
| >Glyma20g33710.2 | >Glyma20g34180.1 | >Glyma20g34600.1 |
| >Glyma20g33720.1 | >Glyma20g34190.1 | >Glyma20g34610.1 |
| >Glyma20g33730.1 | >Glyma20g34200.1 | >Glyma20g34620.1 |
| >Glyma20g33740.1 | >Glyma20g34210.1 | >Glyma20g34630.1 |

FIG. 4

| | | |
|---|---|---|
| >Glyma20g34630.2 | >Glyma20g35010.1 | >Glyma20g35430.1 |
| >Glyma20g34640.1 | >Glyma20g35020.1 | >Glyma20g35430.2 |
| >Glyma20g34650.1 | >Glyma20g35030.1 | >Glyma20g35430.3 |
| >Glyma20g34660.1 | >Glyma20g35040.1 | >Glyma20g35440.1 |
| >Glyma20g34670.1 | >Glyma20g35050.1 | >Glyma20g35450.1 |
| >Glyma20g34680.1 | >Glyma20g35060.1 | >Glyma20g35460.1 |
| >Glyma20g34690.1 | >Glyma20g35070.1 | >Glyma20g35470.1 |
| >Glyma20g34690.2 | >Glyma20g35080.1 | >Glyma20g35480.1 |
| >Glyma20g34690.3 | >Glyma20g35090.1 | >Glyma20g35490.1 |
| >Glyma20g34700.1 | >Glyma20g35090.2 | >Glyma20g35500.1 |
| >Glyma20g34710.1 | >Glyma20g35100.1 | >Glyma20g35510.1 |
| >Glyma20g34720.1 | >Glyma20g35110.1 | >Glyma20g35520.1 |
| >Glyma20g34730.1 | >Glyma20g35110.2 | >Glyma20g35530.1 |
| >Glyma20g34740.1 | >Glyma20g35120.1 | >Glyma20g35550.1 |
| >Glyma20g34750.1 | >Glyma20g35120.2 | >Glyma20g35570.1 |
| >Glyma20g34750.2 | >Glyma20g35120.3 | >Glyma20g35580.1 |
| >Glyma20g34760.1 | >Glyma20g35120.4 | >Glyma20g35590.1 |
| >Glyma20g34770.1 | >Glyma20g35130.1 | >Glyma20g35600.1 |
| >Glyma20g34780.1 | >Glyma20g35140.1 | >Glyma20g35610.1 |
| >Glyma20g34780.2 | >Glyma20g35150.1 | >Glyma20g35620.1 |
| >Glyma20g34780.3 | >Glyma20g35160.1 | >Glyma20g35630.1 |
| >Glyma20g34780.4 | >Glyma20g35170.1 | >Glyma20g35640.1 |
| >Glyma20g34790.1 | >Glyma20g35180.1 | >Glyma20g35650.1 |
| >Glyma20g34800.1 | >Glyma20g35190.1 | >Glyma20g35660.1 |
| >Glyma20g34810.1 | >Glyma20g35200.1 | >Glyma20g35670.1 |
| >Glyma20g34820.1 | >Glyma20g35210.1 | >Glyma20g35680.1 |
| >Glyma20g34830.1 | >Glyma20g35220.1 | >Glyma20g35690.1 |
| >Glyma20g34840.1 | >Glyma20g35230.1 | >Glyma20g35700.1 |
| >Glyma20g34850.1 | >Glyma20g35240.1 | >Glyma20g35710.1 |
| >Glyma20g34860.1 | >Glyma20g35250.1 | >Glyma20g35720.1 |
| >Glyma20g34870.1 | >Glyma20g35260.1 | >Glyma20g35730.1 |
| >Glyma20g34880.1 | >Glyma20g35260.2 | >Glyma20g35740.1 |
| >Glyma20g34880.2 | >Glyma20g35270.1 | >Glyma20g35750.1 |
| >Glyma20g34890.1 | >Glyma20g35280.1 | >Glyma20g35750.2 |
| >Glyma20g34900.1 | >Glyma20g35290.1 | >Glyma20g35760.1 |
| >Glyma20g34910.1 | >Glyma20g35300.1 | >Glyma20g35770.1 |
| >Glyma20g34920.1 | >Glyma20g35300.2 | >Glyma20g35770.2 |
| >Glyma20g34930.1 | >Glyma20g35310.1 | >Glyma20g35770.3 |
| >Glyma20g34930.2 | >Glyma20g35320.1 | >Glyma20g35770.4 |
| >Glyma20g34940.1 | >Glyma20g35340.1 | >Glyma20g35770.5 |
| >Glyma20g34950.1 | >Glyma20g35350.1 | >Glyma20g35780.1 |
| >Glyma20g34960.1 | >Glyma20g35360.1 | >Glyma20g35790.1 |
| >Glyma20g34970.1 | >Glyma20g35370.1 | >Glyma20g35800.1 |
| >Glyma20g34980.1 | >Glyma20g35380.1 | >Glyma20g35810.1 |
| >Glyma20g34980.2 | >Glyma20g35390.1 | >Glyma20g35820.1 |
| >Glyma20g34990.1 | >Glyma20g35400.1 | >Glyma20g35830.1 |
| >Glyma20g35000.1 | >Glyma20g35410.1 | >Glyma20g35830.2 |
| >Glyma20g35000.2 | >Glyma20g35420.1 | >Glyma20g35830.3 |

FIG. 4 (cont.)

| | | |
|---|---|---|
| >Glyma20g35840.1 | >Glyma20g36250.1 | >Glyma20g36690.1 |
| >Glyma20g35850.1 | >Glyma20g36260.1 | >Glyma20g36690.2 |
| >Glyma20g35860.1 | >Glyma20g36270.1 | >Glyma20g36700.1 |
| >Glyma20g35870.1 | >Glyma20g36280.1 | >Glyma20g36720.1 |
| >Glyma20g35880.1 | >Glyma20g36290.1 | >Glyma20g36730.1 |
| >Glyma20g35890.1 | >Glyma20g36300.1 | >Glyma20g36740.1 |
| >Glyma20g35900.1 | >Glyma20g36310.1 | >Glyma20g36740.2 |
| >Glyma20g35910.1 | >Glyma20g36320.1 | >Glyma20g36740.3 |
| >Glyma20g35920.1 | >Glyma20g36330.1 | >Glyma20g36750.1 |
| >Glyma20g35930.1 | >Glyma20g36330.2 | >Glyma20g36750.2 |
| >Glyma20g35940.1 | >Glyma20g36340.1 | >Glyma20g36760.1 |
| >Glyma20g35950.1 | >Glyma20g36350.1 | >Glyma20g36760.2 |
| >Glyma20g35960.1 | >Glyma20g36360.1 | >Glyma20g36770.1 |
| >Glyma20g35970.1 | >Glyma20g36370.1 | >Glyma20g36770.2 |
| >Glyma20g35970.2 | >Glyma20g36380.1 | >Glyma20g36780.1 |
| >Glyma20g35980.1 | >Glyma20g36390.1 | >Glyma20g36790.1 |
| >Glyma20g35990.1 | >Glyma20g36400.1 | >Glyma20g36800.1 |
| >Glyma20g35990.2 | >Glyma20g36410.1 | >Glyma20g36810.1 |
| >Glyma20g36000.1 | >Glyma20g36420.1 | >Glyma20g36820.1 |
| >Glyma20g36010.1 | >Glyma20g36430.1 | >Glyma20g36830.1 |
| >Glyma20g36010.2 | >Glyma20g36440.1 | >Glyma20g36840.1 |
| >Glyma20g36020.1 | >Glyma20g36450.1 | >Glyma20g36850.1 |
| >Glyma20g36030.1 | >Glyma20g36460.1 | >Glyma20g36860.1 |
| >Glyma20g36040.1 | >Glyma20g36470.1 | >Glyma20g36870.1 |
| >Glyma20g36050.1 | >Glyma20g36480.1 | >Glyma20g36880.1 |
| >Glyma20g36050.2 | >Glyma20g36490.1 | >Glyma20g36880.2 |
| >Glyma20g36060.1 | >Glyma20g36500.1 | >Glyma20g36890.1 |
| >Glyma20g36070.1 | >Glyma20g36510.1 | >Glyma20g36900.1 |
| >Glyma20g36080.1 | >Glyma20g36520.1 | >Glyma20g36910.1 |
| >Glyma20g36090.1 | >Glyma20g36530.1 | >Glyma20g36930.1 |
| >Glyma20g36100.1 | >Glyma20g36540.1 | >Glyma20g36940.1 |
| >Glyma20g36110.1 | >Glyma20g36550.1 | >Glyma20g36950.1 |
| >Glyma20g36110.2 | >Glyma20g36560.1 | >Glyma20g36960.1 |
| >Glyma20g36120.1 | >Glyma20g36570.1 | >Glyma20g36960.2 |
| >Glyma20g36120.2 | >Glyma20g36580.1 | >Glyma20g36970.1 |
| >Glyma20g36130.1 | >Glyma20g36590.1 | >Glyma20g36980.1 |
| >Glyma20g36140.1 | >Glyma20g36590.2 | >Glyma20g36990.1 |
| >Glyma20g36150.1 | >Glyma20g36600.1 | >Glyma20g37000.1 |
| >Glyma20g36160.1 | >Glyma20g36600.2 | >Glyma20g37010.1 |
| >Glyma20g36170.1 | >Glyma20g36620.1 | >Glyma20g37020.1 |
| >Glyma20g36180.1 | >Glyma20g36620.2 | >Glyma20g37040.1 |
| >Glyma20g36190.1 | >Glyma20g36630.1 | >Glyma20g37050.1 |
| >Glyma20g36190.2 | >Glyma20g36630.2 | >Glyma20g37100.1 |
| >Glyma20g36200.1 | >Glyma20g36640.1 | >Glyma20g37110.1 |
| >Glyma20g36210.1 | >Glyma20g36650.1 | >Glyma20g37120.1 |
| >Glyma20g36220.1 | >Glyma20g36660.1 | >Glyma20g37130.1 |
| >Glyma20g36230.1 | >Glyma20g36670.1 | >Glyma20g37150.1 |
| >Glyma20g36240.1 | >Glyma20g36680.1 | >Glyma20g37160.1 |

FIG. 4 (cont.)

>Glyma20g37170.1
>Glyma20g37170.2
>Glyma20g37180.1
>Glyma20g37190.1
>Glyma20g37190.2
>Glyma20g37190.3
>Glyma20g37200.1
>Glyma20g37210.1
>Glyma20g37220.1
>Glyma20g37230.1
>Glyma20g37240.1
>Glyma20g37250.1
>Glyma20g37260.1
>Glyma20g37260.2
>Glyma20g37270.1
>Glyma20g37280.1
>Glyma20g37280.2
>Glyma20g37280.3
>Glyma20g37290.1
>Glyma20g37310.1
>Glyma20g37320.1
>Glyma20g37330.1
>Glyma20g37330.2
>Glyma20g37330.3
>Glyma20g37340.1
>Glyma20g37350.1
>Glyma20g37360.1
>Glyma20g37370.1
>Glyma20g37380.1
>Glyma20g37390.1
>Glyma20g37400.1
>Glyma20g37410.1
>Glyma20g37420.1
>Glyma20g37430.1
>Glyma20g37440.1
>Glyma20g37450.1
>Glyma20g37460.1
>Glyma20g37460.2
>Glyma20g37470.1
>Glyma20g37480.1
>Glyma20g37500.1
>Glyma20g37510.1
>Glyma20g37520.1
>Glyma20g37530.1
>Glyma20g37540.1
>Glyma20g37550.1
>Glyma20g37560.1
>Glyma20g37570.1

>Glyma20g37580.1
>Glyma20g37590.1
>Glyma20g37600.1
>Glyma20g37610.1
>Glyma20g37620.1
>Glyma20g37630.1
>Glyma20g37640.1
>Glyma20g37650.1
>Glyma20g37660.1
>Glyma20g37660.2
>Glyma20g37670.1
>Glyma20g37680.1
>Glyma20g37690.1
>Glyma20g37690.2
>Glyma20g37700.1
>Glyma20g37710.1
>Glyma20g37720.1
>Glyma20g37730.1
>Glyma20g37730.2
>Glyma20g37740.1
>Glyma20g37750.1
>Glyma20g37750.2
>Glyma20g37760.1
>Glyma20g37770.1
>Glyma20g37780.1

FIG. 4 (cont.)

>Glyma18g51590.1
>Glyma18g51600.1
>Glyma18g51610.1
>Glyma18g51620.1
>Glyma18g51630.1
>Glyma18g51640.1
>Glyma18g51650.1
>Glyma18g51660.1
>Glyma18g51670.1
>Glyma18g51680.1
>Glyma18g51690.1
>Glyma18g51700.1
>Glyma18g51710.1
>Glyma18g51720.1
>Glyma18g51730.1
>Glyma18g51740.1
>Glyma18g51750.1
>Glyma18g51760.1
>Glyma18g51770.1
>Glyma18g51780.1
>Glyma18g51790.1
>Glyma18g51800.1
>Glyma18g51810.1
>Glyma18g51820.1
>Glyma18g51830.1
>Glyma18g51840.1
>Glyma18g51850.1
>Glyma18g51860.1
>Glyma18g51870.1
>Glyma18g51880.1
>Glyma18g51890.1
>Glyma18g51900.1
>Glyma18g51920.1
>Glyma18g51930.1
>Glyma18g51950.1
>Glyma18g51960.1
>Glyma18g51970.1
>Glyma18g51980.1
>Glyma18g51990.1
>Glyma18g52000.1
>Glyma18g52010.1

>Glyma18g52020.1
>Glyma18g52030.1
>Glyma18g52040.1
>Glyma18g52050.1
>Glyma18g52060.1
>Glyma18g52070.1
>Glyma18g52080.1
>Glyma18g52090.1
>Glyma18g52110.1
>Glyma18g52120.1
>Glyma18g52130.1
>Glyma18g52140.1
>Glyma18g52150.1
>Glyma18g52160.1
>Glyma18g52170.1
>Glyma18g52180.1
>Glyma18g52190.1
>Glyma18g52200.1
>Glyma18g52210.1
>Glyma18g52220.1
>Glyma18g52230.1
>Glyma18g52240.1
>Glyma18g52250.1
>Glyma18g52260.1
>Glyma18g52270.1
>Glyma18g52280.1
>Glyma18g52290.1
>Glyma18g52300.1
>Glyma18g52300.2
>Glyma18g52310.1
>Glyma18g52320.1
>Glyma18g52330.1
>Glyma18g52340.1
>Glyma18g52350.1
>Glyma18g52360.1
>Glyma18g52370.1
>Glyma18g52380.1
>Glyma18g52390.1
>Glyma18g52400.1
>Glyma18g52410.1
>Glyma18g52420.1

>Glyma18g52430.1
>Glyma18g52440.1
>Glyma18g52450.1
>Glyma18g52450.2
>Glyma18g52450.3
>Glyma18g52460.1
>Glyma18g52470.1
>Glyma18g52480.1
>Glyma18g52490.1
>Glyma18g52500.1
>Glyma18g52510.1

FIG. 5

>Glyma04g34160.1
>Glyma04g34170.1
>Glyma04g34170.2
>Glyma04g34180.1
>Glyma04g34190.1
>Glyma04g34200.1
>Glyma04g34210.1
>Glyma04g34220.1
>Glyma04g34230.1
>Glyma04g34240.1
>Glyma04g34250.1
>Glyma04g34260.1
>Glyma04g34270.1
>Glyma04g34280.1
>Glyma04g34290.1
>Glyma04g34300.1
>Glyma04g34310.1
>Glyma04g34320.1
>Glyma04g34330.1
>Glyma04g34330.2
>Glyma04g34340.1
>Glyma04g34350.1
>Glyma04g34360.1
>Glyma04g34370.1
>Glyma04g34380.1
>Glyma04g34390.1
>Glyma04g34400.1
>Glyma04g34420.1
>Glyma04g34430.1
>Glyma04g34440.1
>Glyma04g34450.1
>Glyma04g34460.1
>Glyma04g34470.1
>Glyma04g34480.1
>Glyma04g34490.1
>Glyma04g34500.1
>Glyma04g34510.1
>Glyma04g34520.1
>Glyma04g34530.1
>Glyma04g34540.1

>Glyma04g34550.1
>Glyma04g34550.2
>Glyma04g34560.1
>Glyma04g34570.1
>Glyma04g34580.1
>Glyma04g34590.1
>Glyma04g34600.1
>Glyma04g34610.1
>Glyma04g34620.1
>Glyma04g34630.1
>Glyma04g34640.1
>Glyma04g34650.1
>Glyma04g34660.1
>Glyma04g34660.2
>Glyma04g34670.1
>Glyma04g34680.1
>Glyma04g34690.1
>Glyma04g34700.1
>Glyma04g34710.1
>Glyma04g34720.1
>Glyma04g34730.1
>Glyma04g34740.1
>Glyma04g34760.1
>Glyma04g34770.1
>Glyma04g34780.1
>Glyma04g34790.1
>Glyma04g34790.2
>Glyma04g34800.1
>Glyma04g34810.1
>Glyma04g34820.1
>Glyma04g34830.1
>Glyma04g34840.1
>Glyma04g34850.1
>Glyma04g34860.1
>Glyma04g34870.1
>Glyma04g34870.2
>Glyma04g34880.1
>Glyma04g34880.2
>Glyma04g34890.1
>Glyma04g34900.1

>Glyma04g34910.1
>Glyma04g34920.1
>Glyma04g34930.1
>Glyma04g34940.1
>Glyma04g34950.1
>Glyma04g34960.1
>Glyma04g34960.2
>Glyma04g34970.1
>Glyma04g34980.1
>Glyma04g34980.2
>Glyma04g34990.1
>Glyma04g35000.1
>Glyma04g35010.1
>Glyma04g35020.1
>Glyma04g35030.1
>Glyma04g35040.1
>Glyma04g35050.1
>Glyma04g35060.1
>Glyma04g35070.1
>Glyma04g35080.1
>Glyma04g35080.2
>Glyma04g35090.1
>Glyma04g35100.1
>Glyma04g35100.2
>Glyma04g35110.1
>Glyma04g35110.2
>Glyma04g35120.1
>Glyma04g35130.1
>Glyma04g35140.1
>Glyma04g35150.1
>Glyma04g35160.1
>Glyma04g35170.1
>Glyma04g35180.1
>Glyma04g35190.1
>Glyma04g35200.1
>Glyma04g35210.1
>Glyma04g35220.1
>Glyma04g35230.1
>Glyma04g35230.2
>Glyma04g35230.3

FIG. 6

| | | |
|---|---|---|
| >Glyma04g35240.1 | >Glyma04g35780.1 | >Glyma04g36170.1 |
| >Glyma04g35250.1 | >Glyma04g35790.1 | >Glyma04g36180.1 |
| >Glyma04g35260.1 | >Glyma04g35800.1 | >Glyma04g36190.1 |
| >Glyma04g35270.1 | >Glyma04g35810.1 | >Glyma04g36200.1 |
| >Glyma04g35280.1 | >Glyma04g35820.1 | >Glyma04g36210.1 |
| >Glyma04g35290.1 | >Glyma04g35820.2 | >Glyma04g36210.2 |
| >Glyma04g35300.1 | >Glyma04g35820.3 | >Glyma04g36220.1 |
| >Glyma04g35310.1 | >Glyma04g35830.1 | |
| >Glyma04g35320.1 | >Glyma04g35840.1 | |
| >Glyma04g35330.1 | >Glyma04g35850.1 | |
| >Glyma04g35340.1 | >Glyma04g35860.1 | |
| >Glyma04g35360.1 | >Glyma04g35860.2 | |
| >Glyma04g35370.1 | >Glyma04g35870.1 | |
| >Glyma04g35380.1 | >Glyma04g35880.1 | |
| >Glyma04g35390.1 | >Glyma04g35890.1 | |
| >Glyma04g35400.1 | >Glyma04g35890.2 | |
| >Glyma04g35410.1 | >Glyma04g35900.1 | |
| >Glyma04g35470.1 | >Glyma04g35910.1 | |
| >Glyma04g35540.1 | >Glyma04g35940.1 | |
| >Glyma04g35560.1 | >Glyma04g35950.1 | |
| >Glyma04g35570.1 | >Glyma04g35960.1 | |
| >Glyma04g35580.1 | >Glyma04g35970.1 | |
| >Glyma04g35590.1 | >Glyma04g35980.1 | |
| >Glyma04g35600.1 | >Glyma04g35990.1 | |
| >Glyma04g35610.1 | >Glyma04g36000.1 | |
| >Glyma04g35620.1 | >Glyma04g36010.1 | |
| >Glyma04g35630.1 | >Glyma04g36020.1 | |
| >Glyma04g35640.1 | >Glyma04g36030.1 | |
| >Glyma04g35650.1 | >Glyma04g36040.1 | |
| >Glyma04g35660.1 | >Glyma04g36050.1 | |
| >Glyma04g35670.1 | >Glyma04g36070.1 | |
| >Glyma04g35680.1 | >Glyma04g36080.1 | |
| >Glyma04g35690.1 | >Glyma04g36090.1 | |
| >Glyma04g35700.1 | >Glyma04g36100.1 | |
| >Glyma04g35710.1 | >Glyma04g36110.1 | |
| >Glyma04g35720.1 | >Glyma04g36120.1 | |
| >Glyma04g35730.1 | >Glyma04g36130.1 | |
| >Glyma04g35740.1 | >Glyma04g36140.1 | |
| >Glyma04g35760.1 | >Glyma04g36150.1 | |
| >Glyma04g35770.1 | >Glyma04g36160.1 | |

FIG. 6 (cont.)

>Glyma04g00930.1
>Glyma04g00940.1
>Glyma04g00950.1
>Glyma04g00950.2
>Glyma04g00960.1
>Glyma04g00970.1
>Glyma04g00980.1
>Glyma04g00990.1
>Glyma04g01000.1
>Glyma04g01000.2
>Glyma04g01000.3
>Glyma04g01010.1
>Glyma04g01010.2
>Glyma04g01020.1
>Glyma04g01020.2
>Glyma04g01020.3
>Glyma04g01030.1
>Glyma04g01040.1
>Glyma04g01050.1
>Glyma04g01060.1
>Glyma04g01070.1
>Glyma04g01070.2
>Glyma04g01080.1
>Glyma04g01090.1
>Glyma04g01090.2
>Glyma04g01100.1
>Glyma04g01100.2
>Glyma04g01110.1
>Glyma04g01120.1
>Glyma04g01130.1
>Glyma04g01130.2
>Glyma04g01130.3
>Glyma04g01140.1
>Glyma04g01150.1
>Glyma04g01160.1
>Glyma04g01170.1
>Glyma04g01170.2
>Glyma04g01170.3
>Glyma04g01180.1
>Glyma04g01190.1
>Glyma04g01190.2
>Glyma04g01200.1
>Glyma04g01210.1

>Glyma04g01220.1
>Glyma04g01230.1
>Glyma04g01240.1
>Glyma04g01250.1
>Glyma04g01260.1
>Glyma04g01270.1
>Glyma04g01280.1
>Glyma04g01290.1
>Glyma04g01300.1
>Glyma04g01310.1
>Glyma04g01320.1
>Glyma04g01330.1
>Glyma04g01340.1
>Glyma04g01350.1
>Glyma04g01360.1
>Glyma04g01370.1
>Glyma04g01370.2
>Glyma04g01380.1
>Glyma04g01380.2
>Glyma04g01390.1
>Glyma04g01390.2
>Glyma04g01390.3
>Glyma04g01390.4
>Glyma04g01400.1
>Glyma04g01400.2
>Glyma04g01400.3
>Glyma04g01410.1
>Glyma04g01430.1
>Glyma04g01440.1
>Glyma04g01450.1
>Glyma04g01460.1
>Glyma04g01470.1
>Glyma04g01480.1
>Glyma04g01490.1
>Glyma04g01500.1
>Glyma04g01510.1
>Glyma04g01520.1
>Glyma04g01530.1
>Glyma04g01540.1
>Glyma04g01550.1
>Glyma04g01560.1
>Glyma04g01570.1
>Glyma04g01580.1

>Glyma04g01580.2
>Glyma04g01580.3
>Glyma04g01580.4
>Glyma04g01590.1
>Glyma04g01600.1
>Glyma04g01600.2
>Glyma04g01610.1
>Glyma04g01610.2
>Glyma04g01620.1
>Glyma04g01630.1
>Glyma04g01630.2
>Glyma04g01640.1
>Glyma04g01650.1
>Glyma04g01660.1
>Glyma04g01670.1
>Glyma04g01680.1
>Glyma04g01690.1
>Glyma04g01700.1
>Glyma04g01700.2
>Glyma04g01700.3
>Glyma04g01700.4
>Glyma04g01710.1
>Glyma04g01720.1
>Glyma04g01730.1
>Glyma04g01740.1
>Glyma04g01750.1
>Glyma04g01750.2
>Glyma04g01760.1
>Glyma04g01770.1
>Glyma04g01780.1
>Glyma04g01790.1
>Glyma04g01800.1
>Glyma04g01810.1
>Glyma04g01820.1
>Glyma04g01820.2
>Glyma04g01830.1
>Glyma04g01840.1
>Glyma04g01840.2
>Glyma04g01840.3
>Glyma04g01840.4
>Glyma04g01840.5
>Glyma04g01840.6
>Glyma04g01840.7

FIG. 7

| | | |
|---|---|---|
| >Glyma04g01840.8 | >Glyma04g02190.1 | >Glyma04g02540.2 |
| >Glyma04g01850.1 | >Glyma04g02200.1 | >Glyma04g02550.1 |
| >Glyma04g01860.1 | >Glyma04g02210.1 | >Glyma04g02560.1 |
| >Glyma04g01870.1 | >Glyma04g02220.1 | >Glyma04g02570.1 |
| >Glyma04g01880.1 | >Glyma04g02220.2 | >Glyma04g02580.1 |
| >Glyma04g01890.1 | >Glyma04g02230.1 | >Glyma04g02590.1 |
| >Glyma04g01900.1 | >Glyma04g02240.1 | >Glyma04g02600.1 |
| >Glyma04g01910.1 | >Glyma04g02250.1 | >Glyma04g02610.1 |
| >Glyma04g01920.1 | >Glyma04g02260.1 | >Glyma04g02620.1 |
| >Glyma04g01920.2 | >Glyma04g02270.1 | >Glyma04g02630.1 |
| >Glyma04g01920.3 | >Glyma04g02280.1 | >Glyma04g02640.1 |
| >Glyma04g01930.1 | >Glyma04g02290.1 | >Glyma04g02640.2 |
| >Glyma04g01940.1 | >Glyma04g02300.1 | >Glyma04g02650.1 |
| >Glyma04g01950.1 | >Glyma04g02320.1 | >Glyma04g02660.1 |
| >Glyma04g01960.1 | >Glyma04g02330.1 | >Glyma04g02670.1 |
| >Glyma04g01970.1 | >Glyma04g02340.1 | >Glyma04g02680.1 |
| >Glyma04g01980.1 | >Glyma04g02350.1 | >Glyma04g02690.1 |
| >Glyma04g01980.2 | >Glyma04g02360.1 | >Glyma04g02700.1 |
| >Glyma04g01990.1 | >Glyma04g02360.2 | >Glyma04g02710.1 |
| >Glyma04g02000.1 | >Glyma04g02370.1 | >Glyma04g02720.1 |
| >Glyma04g02000.2 | >Glyma04g02380.1 | >Glyma04g02720.2 |
| >Glyma04g02000.3 | >Glyma04g02380.2 | >Glyma04g02730.1 |
| >Glyma04g02010.1 | >Glyma04g02390.1 | >Glyma04g02740.1 |
| >Glyma04g02020.1 | >Glyma04g02400.1 | >Glyma04g02750.1 |
| >Glyma04g02030.1 | >Glyma04g02410.1 | >Glyma04g02760.1 |
| >Glyma04g02030.2 | >Glyma04g02410.2 | >Glyma04g02770.1 |
| >Glyma04g02030.3 | >Glyma04g02420.1 | >Glyma04g02780.1 |
| >Glyma04g02040.1 | >Glyma04g02430.1 | >Glyma04g02790.1 |
| >Glyma04g02050.1 | >Glyma04g02440.1 | >Glyma04g02800.1 |
| >Glyma04g02060.1 | >Glyma04g02450.1 | >Glyma04g02810.1 |
| >Glyma04g02070.1 | >Glyma04g02460.1 | >Glyma04g02820.1 |
| >Glyma04g02080.1 | >Glyma04g02460.2 | >Glyma04g02830.1 |
| >Glyma04g02090.1 | >Glyma04g02470.1 | >Glyma04g02840.1 |
| >Glyma04g02100.1 | >Glyma04g02480.1 | >Glyma04g02850.1 |
| >Glyma04g02110.1 | >Glyma04g02490.1 | >Glyma04g02850.2 |
| >Glyma04g02120.1 | >Glyma04g02500.1 | >Glyma04g02860.1 |
| >Glyma04g02130.1 | >Glyma04g02510.1 | >Glyma04g02870.1 |
| >Glyma04g02140.1 | >Glyma04g02510.2 | >Glyma04g02880.1 |
| >Glyma04g02150.1 | >Glyma04g02520.1 | >Glyma04g02890.1 |
| >Glyma04g02160.1 | >Glyma04g02530.1 | >Glyma04g02900.1 |
| >Glyma04g02170.1 | >Glyma04g02530.2 | >Glyma04g02900.2 |
| >Glyma04g02180.1 | >Glyma04g02530.3 | >Glyma04g02910.1 |
| >Glyma04g02180.2 | >Glyma04g02540.1 | >Glyma04g02920.1 |

FIG. 7 (cont.)

>Glyma04g02930.1
>Glyma04g02940.1
>Glyma04g02950.1
>Glyma04g02960.1
>Glyma04g02960.2
>Glyma04g02970.1
>Glyma04g02980.1
>Glyma04g02990.1
>Glyma04g03000.1
>Glyma04g03010.1
>Glyma04g03020.1
>Glyma04g03030.1
>Glyma04g03030.2
>Glyma04g03040.1
>Glyma04g03040.2
>Glyma04g03050.1
>Glyma04g03060.1
>Glyma04g03070.1
>Glyma04g03080.1
>Glyma04g03080.2
>Glyma04g03090.1
>Glyma04g03100.1
>Glyma04g03110.1
>Glyma04g03120.1
>Glyma04g03130.1
>Glyma04g03140.1
>Glyma04g03150.1
>Glyma04g03160.1
>Glyma04g03170.1
>Glyma04g03180.1
>Glyma04g03190.1
>Glyma04g03200.1
>Glyma04g03210.1
>Glyma04g03220.1
>Glyma04g03230.1
>Glyma04g03240.1
>Glyma04g03250.1

FIG. 7 (cont.)

>Glyma18g01760.1
>Glyma18g01770.1
>Glyma18g01780.1
>Glyma18g01780.2
>Glyma18g01790.1
>Glyma18g01800.1
>Glyma18g01810.1
>Glyma18g01820.1
>Glyma18g01830.1
>Glyma18g01840.1
>Glyma18g01850.1
>Glyma18g01850.2
>Glyma18g01860.1
>Glyma18g01860.2
>Glyma18g01860.3
>Glyma18g01870.1
>Glyma18g01880.1
>Glyma18g01890.1
>Glyma18g01890.2
>Glyma18g01900.1
>Glyma18g01910.1
>Glyma18g01920.1
>Glyma18g01920.2
>Glyma18g01930.1
>Glyma18g01940.1
>Glyma18g01950.1
>Glyma18g01960.1
>Glyma18g01970.1
>Glyma18g01980.1
>Glyma18g01990.1
>Glyma18g02010.1
>Glyma18g02020.1
>Glyma18g02030.1
>Glyma18g02030.2
>Glyma18g02040.1
>Glyma18g02050.1
>Glyma18g02060.1
>Glyma18g02070.1
>Glyma18g02070.2
>Glyma18g02070.3
>Glyma18g02080.1
>Glyma18g02080.2
>Glyma18g02080.3
>Glyma18g02090.1
>Glyma18g02100.1

>Glyma18g02110.1
>Glyma18g02120.1
>Glyma18g02130.1
>Glyma18g02140.1
>Glyma18g02150.1
>Glyma18g02160.1
>Glyma18g02170.1
>Glyma18g02180.1
>Glyma18g02190.1
>Glyma18g02200.1
>Glyma18g02210.1
>Glyma18g02210.2
>Glyma18g02210.3
>Glyma18g02210.4
>Glyma18g02220.1
>Glyma18g02230.1
>Glyma18g02230.2
>Glyma18g02240.1
>Glyma18g02250.1
>Glyma18g02260.1
>Glyma18g02270.1
>Glyma18g02280.1
>Glyma18g02280.2
>Glyma18g02280.3
>Glyma18g02290.1
>Glyma18g02300.1
>Glyma18g02310.1
>Glyma18g02320.1
>Glyma18g02330.1
>Glyma18g02340.1
>Glyma18g02350.1
>Glyma18g02360.1
>Glyma18g02370.1
>Glyma18g02380.1
>Glyma18g02390.1
>Glyma18g02400.1
>Glyma18g02410.1
>Glyma18g02420.1
>Glyma18g02430.1
>Glyma18g02430.2
>Glyma18g02430.3
>Glyma18g02430.4
>Glyma18g02440.1
>Glyma18g02450.1
>Glyma18g02450.2

>Glyma18g02460.1
>Glyma18g02470.1
>Glyma18g02480.1
>Glyma18g02490.1
>Glyma18g02500.1
>Glyma18g02510.1
>Glyma18g02520.1
>Glyma18g02530.1
>Glyma18g02540.1
>Glyma18g02550.1
>Glyma18g02560.1
>Glyma18g02570.1
>Glyma18g02580.1
>Glyma18g02590.1
>Glyma18g02600.1
>Glyma18g02610.1
>Glyma18g02620.1
>Glyma18g02630.1
>Glyma18g02640.1
>Glyma18g02650.1
>Glyma18g02650.2
>Glyma18g02660.1
>Glyma18g02670.1
>Glyma18g02680.1
>Glyma18g02690.1
>Glyma18g02700.1
>Glyma18g02710.1
>Glyma18g02720.1
>Glyma18g02730.1
>Glyma18g02740.1
>Glyma18g02750.1
>Glyma18g02760.1
>Glyma18g02770.1
>Glyma18g02780.1
>Glyma18g02790.1
>Glyma18g02800.1
>Glyma18g02800.2
>Glyma18g02810.1
>Glyma18g02820.1
>Glyma18g02830.1
>Glyma18g02840.1
>Glyma18g02850.1
>Glyma18g02860.1
>Glyma18g02870.1
>Glyma18g02880.1

FIG. 8

| | | |
|---|---|---|
| >Glyma18g02890.1 | >Glyma18g03330.1 | >Glyma18g03780.1 |
| >Glyma18g02900.1 | >Glyma18g03340.1 | >Glyma18g03790.1 |
| >Glyma18g02910.1 | >Glyma18g03350.1 | >Glyma18g03800.1 |
| >Glyma18g02920.1 | >Glyma18g03360.1 | >Glyma18g03810.1 |
| >Glyma18g02930.1 | >Glyma18g03370.1 | >Glyma18g03820.1 |
| >Glyma18g02940.1 | >Glyma18g03380.1 | >Glyma18g03830.1 |
| >Glyma18g02950.1 | >Glyma18g03390.1 | >Glyma18g03840.1 |
| >Glyma18g02960.1 | >Glyma18g03400.1 | >Glyma18g03850.1 |
| >Glyma18g02970.1 | >Glyma18g03420.1 | >Glyma18g03860.1 |
| >Glyma18g02980.1 | >Glyma18g03430.1 | >Glyma18g03870.1 |
| >Glyma18g02990.1 | >Glyma18g03440.1 | >Glyma18g03880.1 |
| >Glyma18g03000.1 | >Glyma18g03450.1 | >Glyma18g03890.1 |
| >Glyma18g03010.1 | >Glyma18g03460.1 | >Glyma18g03890.2 |
| >Glyma18g03020.1 | >Glyma18g03470.1 | >Glyma18g03900.1 |
| >Glyma18g03030.1 | >Glyma18g03480.1 | >Glyma18g03910.1 |
| >Glyma18g03040.1 | >Glyma18g03490.1 | >Glyma18g03930.1 |
| >Glyma18g03050.1 | >Glyma18g03500.1 | >Glyma18g03940.1 |
| >Glyma18g03060.1 | >Glyma18g03510.1 | >Glyma18g03950.1 |
| >Glyma18g03070.1 | >Glyma18g03520.1 | >Glyma18g03960.1 |
| >Glyma18g03080.1 | >Glyma18g03530.1 | >Glyma18g03970.1 |
| >Glyma18g03090.1 | >Glyma18g03540.1 | >Glyma18g03980.1 |
| >Glyma18g03100.1 | >Glyma18g03550.1 | >Glyma18g03980.2 |
| >Glyma18g03110.1 | >Glyma18g03560.1 | >Glyma18g03980.3 |
| >Glyma18g03120.1 | >Glyma18g03570.1 | >Glyma18g03990.1 |
| >Glyma18g03130.1 | >Glyma18g03580.1 | >Glyma18g04000.1 |
| >Glyma18g03140.1 | >Glyma18g03590.1 | >Glyma18g04010.1 |
| >Glyma18g03150.1 | >Glyma18g03600.1 | >Glyma18g04020.1 |
| >Glyma18g03160.1 | >Glyma18g03610.1 | >Glyma18g04030.1 |
| >Glyma18g03170.1 | >Glyma18g03620.1 | >Glyma18g04040.1 |
| >Glyma18g03180.1 | >Glyma18g03630.1 | >Glyma18g04050.1 |
| >Glyma18g03190.1 | >Glyma18g03640.1 | >Glyma18g04060.1 |
| >Glyma18g03200.1 | >Glyma18g03640.2 | >Glyma18g04070.1 |
| >Glyma18g03210.1 | >Glyma18g03650.1 | >Glyma18g04080.1 |
| >Glyma18g03220.1 | >Glyma18g03660.1 | >Glyma18g04090.1 |
| >Glyma18g03220.2 | >Glyma18g03670.1 | >Glyma18g04110.1 |
| >Glyma18g03230.1 | >Glyma18g03680.1 | >Glyma18g04120.1 |
| >Glyma18g03240.1 | >Glyma18g03690.1 | >Glyma18g04130.1 |
| >Glyma18g03250.1 | >Glyma18g03700.1 | >Glyma18g04140.1 |
| >Glyma18g03260.1 | >Glyma18g03710.1 | >Glyma18g04150.1 |
| >Glyma18g03270.1 | >Glyma18g03720.1 | >Glyma18g04160.1 |
| >Glyma18g03280.1 | >Glyma18g03730.1 | >Glyma18g04170.1 |
| >Glyma18g03290.1 | >Glyma18g03740.1 | >Glyma18g04180.1 |
| >Glyma18g03300.1 | >Glyma18g03750.1 | >Glyma18g04190.1 |
| >Glyma18g03310.1 | >Glyma18g03760.1 | >Glyma18g04200.1 |
| >Glyma18g03320.1 | >Glyma18g03770.1 | >Glyma18g04210.1 |

FIG. 8 (cont.)

| | | |
|---|---|---|
| >Glyma18g04220.1 | >Glyma18g04670.1 | >Glyma18g05120.1 |
| >Glyma18g04230.1 | >Glyma18g04680.1 | >Glyma18g05130.1 |
| >Glyma18g04240.1 | >Glyma18g04690.1 | >Glyma18g05140.1 |
| >Glyma18g04250.1 | >Glyma18g04700.1 | >Glyma18g05150.1 |
| >Glyma18g04260.1 | >Glyma18g04710.1 | >Glyma18g05160.1 |
| >Glyma18g04270.1 | >Glyma18g04720.1 | >Glyma18g05170.1 |
| >Glyma18g04280.1 | >Glyma18g04730.1 | >Glyma18g05170.2 |
| >Glyma18g04290.1 | >Glyma18g04740.1 | >Glyma18g05180.1 |
| >Glyma18g04300.1 | >Glyma18g04750.1 | >Glyma18g05190.1 |
| >Glyma18g04310.1 | >Glyma18g04760.1 | >Glyma18g05200.1 |
| >Glyma18g04320.1 | >Glyma18g04770.1 | >Glyma18g05210.1 |
| >Glyma18g04330.1 | >Glyma18g04780.1 | >Glyma18g05220.1 |
| >Glyma18g04340.1 | >Glyma18g04790.1 | >Glyma18g05230.1 |
| >Glyma18g04350.1 | >Glyma18g04800.1 | >Glyma18g05240.1 |
| >Glyma18g04360.1 | >Glyma18g04810.1 | >Glyma18g05250.1 |
| >Glyma18g04370.1 | >Glyma18g04820.1 | >Glyma18g05260.1 |
| >Glyma18g04380.1 | >Glyma18g04830.1 | >Glyma18g05270.1 |
| >Glyma18g04390.1 | >Glyma18g04840.1 | >Glyma18g05280.1 |
| >Glyma18g04400.1 | >Glyma18g04850.1 | >Glyma18g05290.1 |
| >Glyma18g04410.1 | >Glyma18g04860.1 | >Glyma18g05300.1 |
| >Glyma18g04420.1 | >Glyma18g04870.1 | >Glyma18g05310.1 |
| >Glyma18g04430.1 | >Glyma18g04880.1 | >Glyma18g05320.1 |
| >Glyma18g04440.1 | >Glyma18g04890.1 | >Glyma18g05330.1 |
| >Glyma18g04450.1 | >Glyma18g04900.1 | >Glyma18g05340.1 |
| >Glyma18g04460.1 | >Glyma18g04910.1 | >Glyma18g05350.1 |
| >Glyma18g04470.1 | >Glyma18g04920.1 | >Glyma18g05360.1 |
| >Glyma18g04480.1 | >Glyma18g04930.1 | >Glyma18g05370.1 |
| >Glyma18g04490.1 | >Glyma18g04940.1 | >Glyma18g05380.1 |
| >Glyma18g04500.1 | >Glyma18g04950.1 | >Glyma18g05390.1 |
| >Glyma18g04510.1 | >Glyma18g04960.1 | >Glyma18g05410.1 |
| >Glyma18g04520.1 | >Glyma18g04970.1 | >Glyma18g05420.1 |
| >Glyma18g04530.1 | >Glyma18g04980.1 | >Glyma18g05430.1 |
| >Glyma18g04540.1 | >Glyma18g04990.1 | >Glyma18g05440.1 |
| >Glyma18g04550.1 | >Glyma18g05000.1 | >Glyma18g05450.1 |
| >Glyma18g04560.1 | >Glyma18g05010.1 | >Glyma18g05460.1 |
| >Glyma18g04570.1 | >Glyma18g05020.1 | >Glyma18g05470.1 |
| >Glyma18g04580.1 | >Glyma18g05030.1 | >Glyma18g05480.1 |
| >Glyma18g04590.1 | >Glyma18g05040.1 | >Glyma18g05490.1 |
| >Glyma18g04600.1 | >Glyma18g05050.1 | >Glyma18g05510.1 |
| >Glyma18g04610.1 | >Glyma18g05060.1 | >Glyma18g05520.1 |
| >Glyma18g04620.1 | >Glyma18g05070.1 | >Glyma18g05530.1 |
| >Glyma18g04630.1 | >Glyma18g05080.1 | >Glyma18g05540.1 |
| >Glyma18g04640.1 | >Glyma18g05090.1 | >Glyma18g05570.1 |
| >Glyma18g04650.1 | >Glyma18g05100.1 | >Glyma18g05580.1 |
| >Glyma18g04660.1 | >Glyma18g05110.1 | >Glyma18g05590.1 |

FIG. 8 (cont.)

>Glyma18g05600.1
>Glyma18g05610.1
>Glyma18g05620.1
>Glyma18g05630.1
>Glyma18g05640.1
>Glyma18g05650.1
>Glyma18g05660.1
>Glyma18g05670.1
>Glyma18g05680.1
>Glyma18g05690.1
>Glyma18g05700.1
>Glyma18g05710.1
>Glyma18g05720.1
>Glyma18g05730.1
>Glyma18g05740.1
>Glyma18g05750.1
>Glyma18g05760.1
>Glyma18g05770.1
>Glyma18g05780.1
>Glyma18g05790.1
>Glyma18g05800.1
>Glyma18g05800.3
>Glyma18g05810.1
>Glyma18g05820.1
>Glyma18g05830.1
>Glyma18g05830.3
>Glyma18g05840.1
>Glyma18g05850.1
>Glyma18g05860.1
>Glyma18g05870.1
>Glyma18g05880.1
>Glyma18g05890.1
>Glyma18g05900.1
>Glyma18g05910.1
>Glyma18g05920.1
>Glyma18g05930.1
>Glyma18g05940.1
>Glyma18g05950.1
>Glyma18g05960.1
>Glyma18g05970.1
>Glyma18g05980.1
>Glyma18g05990.1
>Glyma18g06000.1
>Glyma18g06010.1
>Glyma18g06020.1

>Glyma18g06030.1
>Glyma18g06040.1
>Glyma18g06050.1
>Glyma18g06060.1
>Glyma18g06070.1
>Glyma18g06080.1
>Glyma18g06090.1

FIG. 8 (cont.)

| | | |
|---|---|---|
| >Glyma08g05580.2 | >Glyma08g05960.1 | >Glyma08g06410.1 |
| >Glyma08g05580.3 | >Glyma08g05970.1 | >Glyma08g06420.1 |
| >Glyma08g05580.4 | >Glyma08g05990.1 | >Glyma08g06430.1 |
| >Glyma08g05590.1 | >Glyma08g06000.1 | >Glyma08g06440.1 |
| >Glyma08g05590.2 | >Glyma08g06010.1 | >Glyma08g06450.1 |
| >Glyma08g05590.3 | >Glyma08g06010.2 | >Glyma08g06460.1 |
| >Glyma08g05590.4 | >Glyma08g06020.1 | >Glyma08g06470.1 |
| >Glyma08g05600.1 | >Glyma08g06030.1 | >Glyma08g06480.1 |
| >Glyma08g05610.1 | >Glyma08g06040.1 | >Glyma08g06490.1 |
| >Glyma08g05610.2 | >Glyma08g06050.1 | >Glyma08g06500.1 |
| >Glyma08g05620.1 | >Glyma08g06060.1 | >Glyma08g06510.1 |
| >Glyma08g05630.1 | >Glyma08g06070.1 | >Glyma08g06520.1 |
| >Glyma08g05640.1 | >Glyma08g06080.1 | >Glyma08g06530.1 |
| >Glyma08g05650.1 | >Glyma08g06090.1 | >Glyma08g06540.1 |
| >Glyma08g05660.1 | >Glyma08g06090.2 | >Glyma08g06550.1 |
| >Glyma08g05670.1 | >Glyma08g06090.3 | >Glyma08g06560.1 |
| >Glyma08g05680.1 | >Glyma08g06100.1 | >Glyma08g06570.1 |
| >Glyma08g05690.1 | >Glyma08g06110.1 | >Glyma08g06570.2 |
| >Glyma08g05700.1 | >Glyma08g06120.1 | >Glyma08g06580.1 |
| >Glyma08g05700.2 | >Glyma08g06130.1 | >Glyma08g06590.1 |
| >Glyma08g05710.1 | >Glyma08g06140.1 | >Glyma08g06610.1 |
| >Glyma08g05720.1 | >Glyma08g06150.1 | >Glyma08g06610.2 |
| >Glyma08g05730.1 | >Glyma08g06160.1 | >Glyma08g06610.3 |
| >Glyma08g05740.1 | >Glyma08g06170.1 | >Glyma08g06620.1 |
| >Glyma08g05750.1 | >Glyma08g06180.1 | >Glyma08g06630.1 |
| >Glyma08g05760.1 | >Glyma08g06190.1 | >Glyma08g06640.1 |
| >Glyma08g05770.1 | >Glyma08g06200.1 | >Glyma08g06650.1 |
| >Glyma08g05780.1 | >Glyma08g06210.1 | >Glyma08g06650.2 |
| >Glyma08g05790.1 | >Glyma08g06220.1 | >Glyma08g06660.1 |
| >Glyma08g05800.1 | >Glyma08g06230.1 | >Glyma08g06670.1 |
| >Glyma08g05810.1 | >Glyma08g06240.1 | >Glyma08g06680.1 |
| >Glyma08g05820.1 | >Glyma08g06250.1 | >Glyma08g06690.1 |
| >Glyma08g05830.1 | >Glyma08g06260.1 | >Glyma08g06700.1 |
| >Glyma08g05840.1 | >Glyma08g06270.1 | >Glyma08g06710.1 |
| >Glyma08g05850.1 | >Glyma08g06280.1 | >Glyma08g06720.1 |
| >Glyma08g05860.1 | >Glyma08g06290.1 | >Glyma08g06730.1 |
| >Glyma08g05870.1 | >Glyma08g06300.1 | >Glyma08g06740.1 |
| >Glyma08g05870.2 | >Glyma08g06300.2 | >Glyma08g06750.1 |
| >Glyma08g05880.1 | >Glyma08g06310.1 | >Glyma08g06760.1 |
| >Glyma08g05890.1 | >Glyma08g06310.2 | >Glyma08g06770.1 |
| >Glyma08g05900.1 | >Glyma08g06320.1 | >Glyma08g06780.1 |
| >Glyma08g05910.1 | >Glyma08g06330.1 | >Glyma08g06780.2 |
| >Glyma08g05920.1 | >Glyma08g06340.1 | >Glyma08g06780.3 |
| >Glyma08g05930.1 | >Glyma08g06350.1 | >Glyma08g06790.1 |
| >Glyma08g05930.2 | >Glyma08g06360.1 | >Glyma08g06810.1 |
| >Glyma08g05940.1 | >Glyma08g06370.1 | >Glyma08g06810.2 |
| >Glyma08g05940.2 | >Glyma08g06380.1 | >Glyma08g06820.1 |
| >Glyma08g05940.3 | >Glyma08g06390.1 | >Glyma08g06830.1 |
| >Glyma08g05950.1 | >Glyma08g06400.1 | >Glyma08g06840.1 |

FIG. 9

>Glyma08g06850.1
>Glyma08g06860.1
>Glyma08g06870.1
>Glyma08g06880.1
>Glyma08g06890.1
>Glyma08g06890.2
>Glyma08g06890.3
>Glyma08g06900.1
>Glyma08g06910.1
>Glyma08g06920.1
>Glyma08g06920.2
>Glyma08g06930.1
>Glyma08g06940.1
>Glyma08g06950.1
>Glyma08g06960.1
>Glyma08g06970.1
>Glyma08g06980.1
>Glyma08g06990.1
>Glyma08g07000.1
>Glyma08g07010.1
>Glyma08g07020.1
>Glyma08g07030.1
>Glyma08g07040.1
>Glyma08g07050.1
>Glyma08g07060.1
>Glyma08g07070.1
>Glyma08g07080.1
>Glyma08g07090.1
>Glyma08g07100.1
>Glyma08g07110.1
>Glyma08g07120.1
>Glyma08g07130.1
>Glyma08g07140.1
>Glyma08g07150.1
>Glyma08g07160.1
>Glyma08g07170.1
>Glyma08g07180.1
>Glyma08g07190.1
>Glyma08g07190.2
>Glyma08g07190.3
>Glyma08g07200.1
>Glyma08g07210.1
>Glyma08g07220.1
>Glyma08g07230.1
>Glyma08g07230.2
>Glyma08g07240.1
>Glyma08g07250.1
>Glyma08g07260.1
>Glyma08g07260.2

>Glyma08g07260.3
>Glyma08g07270.1
>Glyma08g07290.1
>Glyma08g07300.1
>Glyma08g07310.1
>Glyma08g07320.1
>Glyma08g07330.1
>Glyma08g07340.1
>Glyma08g07350.1
>Glyma08g07360.1
>Glyma08g07370.1
>Glyma08g07380.1
>Glyma08g07390.1
>Glyma08g07400.1
>Glyma08g07410.1
>Glyma08g07420.1
>Glyma08g07430.1
>Glyma08g07440.1
>Glyma08g07450.1
>Glyma08g07460.1
>Glyma08g07470.1
>Glyma08g07480.1
>Glyma08g07490.1
>Glyma08g07500.1
>Glyma08g07510.1
>Glyma08g07510.2
>Glyma08g07520.1
>Glyma08g07530.1
>Glyma08g07540.1
>Glyma08g07550.1
>Glyma08g07560.1
>Glyma08g07570.1
>Glyma08g07580.1
>Glyma08g07590.1
>Glyma08g07600.1
>Glyma08g07610.1
>Glyma08g07620.1
>Glyma08g07630.1
>Glyma08g07640.1
>Glyma08g07650.1
>Glyma08g07660.1
>Glyma08g07670.1
>Glyma08g07670.2
>Glyma08g07680.1
>Glyma08g07690.1
>Glyma08g07700.1
>Glyma08g07710.1
>Glyma08g07710.2
>Glyma08g07720.1

>Glyma08g07730.1
>Glyma08g07740.1
>Glyma08g07750.1
>Glyma08g07760.1
>Glyma08g07770.1
>Glyma08g07780.1
>Glyma08g07790.1
>Glyma08g07800.1
>Glyma08g07810.1
>Glyma08g07820.1
>Glyma08g07830.1
>Glyma08g07830.2
>Glyma08g07840.1
>Glyma08g07850.1
>Glyma08g07860.1
>Glyma08g07860.2
>Glyma08g07870.1
>Glyma08g07880.1
>Glyma08g07890.1
>Glyma08g07900.1
>Glyma08g07910.1
>Glyma08g07920.1
>Glyma08g07930.1
>Glyma08g07940.1
>Glyma08g07950.1
>Glyma08g07950.2
>Glyma08g07960.1
>Glyma08g07970.1
>Glyma08g07980.1
>Glyma08g07990.1
>Glyma08g07990.2
>Glyma08g08000.1
>Glyma08g08010.1
>Glyma08g08020.1
>Glyma08g08030.1
>Glyma08g08040.1
>Glyma08g08050.1
>Glyma08g08060.1
>Glyma08g08070.1
>Glyma08g08080.1
>Glyma08g08090.1
>Glyma08g08100.1
>Glyma08g08110.1
>Glyma08g08120.1
>Glyma08g08130.1
>Glyma08g08140.1
>Glyma08g08150.1
>Glyma08g08160.1
>Glyma08g08170.1

FIG. 9 (cont.)

>Glyma08g08180.1
>Glyma08g08180.2
>Glyma08g08190.1
>Glyma08g08190.2
>Glyma08g08190.3
>Glyma08g08200.1
>Glyma08g08210.1
>Glyma08g08220.1
>Glyma08g08230.1
>Glyma08g08240.1
>Glyma08g08250.1
>Glyma08g08260.1
>Glyma08g08260.2
>Glyma08g08270.1
>Glyma08g08280.1
>Glyma08g08280.2
>Glyma08g08290.1
>Glyma08g08300.1
>Glyma08g08310.1
>Glyma08g08310.2
>Glyma08g08310.3
>Glyma08g08310.4
>Glyma08g08320.1
>Glyma08g08330.1
>Glyma08g08330.2
>Glyma08g08340.1
>Glyma08g08350.1
>Glyma08g08360.1
>Glyma08g08370.1
>Glyma08g08380.1
>Glyma08g08390.1
>Glyma08g08400.1
>Glyma08g08410.1
>Glyma08g08420.1
>Glyma08g08430.1
>Glyma08g08440.1
>Glyma08g08450.1
>Glyma08g08460.1
>Glyma08g08470.1
>Glyma08g08480.1
>Glyma08g08490.1
>Glyma08g08500.1
>Glyma08g08510.1
>Glyma08g08520.1
>Glyma08g08530.1
>Glyma08g08540.1
>Glyma08g08550.1
>Glyma08g08560.1
>Glyma08g08570.1

>Glyma08g08580.1
>Glyma08g08580.2
>Glyma08g08590.1
>Glyma08g08590.2
>Glyma08g08600.1
>Glyma08g08610.1
>Glyma08g08610.2
>Glyma08g08610.3
>Glyma08g08610.4
>Glyma08g08620.1
>Glyma08g08630.1
>Glyma08g08650.1
>Glyma08g08660.1
>Glyma08g08660.2
>Glyma08g08670.1
>Glyma08g08680.1
>Glyma08g08690.1
>Glyma08g08700.1
>Glyma08g08700.2
>Glyma08g08700.3
>Glyma08g08710.1
>Glyma08g08720.1
>Glyma08g08730.1
>Glyma08g08740.1
>Glyma08g08750.1
>Glyma08g08760.1
>Glyma08g08770.1
>Glyma08g08770.2
>Glyma08g08780.1
>Glyma08g08790.1
>Glyma08g08800.1
>Glyma08g08810.1
>Glyma08g08820.1
>Glyma08g08830.1
>Glyma08g08840.1
>Glyma08g08850.1
>Glyma08g08860.1
>Glyma08g08870.1
>Glyma08g08880.1
>Glyma08g08890.1
>Glyma08g08890.2
>Glyma08g08900.1
>Glyma08g08910.1
>Glyma08g08910.2
>Glyma08g08920.1
>Glyma08g08920.2
>Glyma08g08930.1
>Glyma08g08940.1
>Glyma08g08950.1

>Glyma08g08960.1
>Glyma08g08970.1
>Glyma08g08970.2
>Glyma08g08970.3
>Glyma08g08980.1
>Glyma08g08990.1
>Glyma08g09000.1
>Glyma08g09010.1
>Glyma08g09020.1
>Glyma08g09030.1
>Glyma08g09040.1
>Glyma08g09050.1
>Glyma08g09060.1
>Glyma08g09070.1
>Glyma08g09080.1
>Glyma08g09080.2
>Glyma08g09080.3
>Glyma08g09090.1
>Glyma08g09100.1
>Glyma08g09110.1
>Glyma08g09120.1
>Glyma08g09130.1
>Glyma08g09140.1
>Glyma08g09150.1
>Glyma08g09160.1
>Glyma08g09170.1
>Glyma08g09170.2
>Glyma08g09180.1
>Glyma08g09190.1
>Glyma08g09200.1
>Glyma08g09200.2
>Glyma08g09210.1
>Glyma08g09220.1
>Glyma08g09230.1
>Glyma08g09240.1
>Glyma08g09250.1
>Glyma08g09260.1
>Glyma08g09260.2
>Glyma08g09260.3
>Glyma08g09260.4
>Glyma08g09270.1
>Glyma08g09270.2
>Glyma08g09280.1
>Glyma08g09290.1
>Glyma08g09300.1
>Glyma08g09310.1
>Glyma08g09310.2
>Glyma08g09320.1
>Glyma08g09330.1

FIG. 9 (cont.)

>Glyma08g09340.1
>Glyma08g09350.1
>Glyma08g09360.1
>Glyma08g09370.1
>Glyma08g09370.2
>Glyma08g09380.1
>Glyma08g09390.1
>Glyma08g09400.1
>Glyma08g09410.1
>Glyma08g09420.1
>Glyma08g09430.1
>Glyma08g09440.1
>Glyma08g09450.1
>Glyma08g09460.1
>Glyma08g09470.1
>Glyma08g09470.2
>Glyma08g09480.1
>Glyma08g09490.1
>Glyma08g09500.1
>Glyma08g09510.1
>Glyma08g09520.1
>Glyma08g09520.2
>Glyma08g09530.1
>Glyma08g09540.1
>Glyma08g09550.1
>Glyma08g09560.1
>Glyma08g09570.1
>Glyma08g09580.1
>Glyma08g09590.1
>Glyma08g09600.1
>Glyma08g09610.1
>Glyma08g09620.1
>Glyma08g09630.1
>Glyma08g09640.1
>Glyma08g09640.2
>Glyma08g09650.1
>Glyma08g09660.1
>Glyma08g09670.1
>Glyma08g09680.1
>Glyma08g09690.1
>Glyma08g09700.1
>Glyma08g09710.1
>Glyma08g09720.1
>Glyma08g09730.1
>Glyma08g09740.1
>Glyma08g09740.2
>Glyma08g09750.1
>Glyma08g09760.1
>Glyma08g09770.1

>Glyma08g09780.1
>Glyma08g09790.1
>Glyma08g09800.1
>Glyma08g09810.1
>Glyma08g09810.2
>Glyma08g09820.1
>Glyma08g09830.1
>Glyma08g09840.1
>Glyma08g09850.1
>Glyma08g09860.1
>Glyma08g09860.2
>Glyma08g09870.1
>Glyma08g09880.1
>Glyma08g09880.2
>Glyma08g09890.1
>Glyma08g09890.2
>Glyma08g09900.1
>Glyma08g09900.2
>Glyma08g09910.1
>Glyma08g09910.2
>Glyma08g09920.1
>Glyma08g09930.1
>Glyma08g09940.1
>Glyma08g09950.1
>Glyma08g09960.1
>Glyma08g09970.1
>Glyma08g09980.1
>Glyma08g09990.1
>Glyma08g10000.1
>Glyma08g10010.1
>Glyma08g10020.1
>Glyma08g10020.2
>Glyma08g10020.3
>Glyma08g10030.1
>Glyma08g10040.1
>Glyma08g10050.1
>Glyma08g10060.1
>Glyma08g10060.2
>Glyma08g10070.1
>Glyma08g10070.2
>Glyma08g10080.1
>Glyma08g10090.1
>Glyma08g10100.1
>Glyma08g10100.2
>Glyma08g10110.1
>Glyma08g10120.1
>Glyma08g10130.1
>Glyma08g10140.1
>Glyma08g10150.1

>Glyma08g10160.1
>Glyma08g10170.1
>Glyma08g10180.1
>Glyma08g10190.1
>Glyma08g10200.1
>Glyma08g10210.1
>Glyma08g10220.1
>Glyma08g10230.1
>Glyma08g10240.1
>Glyma08g10250.1
>Glyma08g10250.2
>Glyma08g10260.1
>Glyma08g10270.1
>Glyma08g10280.1
>Glyma08g10290.1
>Glyma08g10300.1
>Glyma08g10310.1
>Glyma08g10320.1
>Glyma08g10330.1
>Glyma08g10340.1
>Glyma08g10350.1
>Glyma08g10360.1
>Glyma08g10370.1
>Glyma08g10380.1
>Glyma08g10390.1
>Glyma08g10400.1
>Glyma08g10410.1
>Glyma08g10420.1
>Glyma08g10430.1
>Glyma08g10440.1
>Glyma08g10450.1
>Glyma08g10460.1
>Glyma08g10470.1
>Glyma08g10480.1
>Glyma08g10490.1
>Glyma08g10500.1
>Glyma08g10510.1
>Glyma08g10520.1
>Glyma08g10530.1
>Glyma08g10540.1
>Glyma08g10550.1
>Glyma08g10550.2
>Glyma08g10560.1
>Glyma08g10570.1
>Glyma08g10570.2
>Glyma08g10580.1
>Glyma08g10590.1
>Glyma08g10590.2
>Glyma08g10600.1

FIG. 9 (cont.)

>Glyma08g10610.1
>Glyma08g10610.2
>Glyma08g10620.1
>Glyma08g10620.2
>Glyma08g10630.1
>Glyma08g10640.1
>Glyma08g10650.1
>Glyma08g10660.1
>Glyma08g10680.1
>Glyma08g10690.1
>Glyma08g10700.1
>Glyma08g10710.1
>Glyma08g10720.1
>Glyma08g10730.1
>Glyma08g10740.1
>Glyma08g10750.1
>Glyma08g10760.1
>Glyma08g10770.1
>Glyma08g10780.1
>Glyma08g10790.1
>Glyma08g10790.2
>Glyma08g10800.1
>Glyma08g10810.1
>Glyma08g10810.2
>Glyma08g10820.1
>Glyma08g10830.1
>Glyma08g10840.1
>Glyma08g10850.1
>Glyma08g10860.1
>Glyma08g10870.1
>Glyma08g10870.2
>Glyma08g10880.1
>Glyma08g10890.1
>Glyma08g10890.2
>Glyma08g10890.3
>Glyma08g10890.4
>Glyma08g10900.1
>Glyma08g10910.1
>Glyma08g10910.2
>Glyma08g10920.1
>Glyma08g10930.1
>Glyma08g10940.1
>Glyma08g10950.1
>Glyma08g10960.1
>Glyma08g10960.2
>Glyma08g10970.1
>Glyma08g10980.1
>Glyma08g10990.1
>Glyma08g10990.2

>Glyma08g11000.1
>Glyma08g11010.1
>Glyma08g11020.1
>Glyma08g11030.1
>Glyma08g11030.2
>Glyma08g11040.1
>Glyma08g11050.1
>Glyma08g11060.1
>Glyma08g11060.2
>Glyma08g11070.1
>Glyma08g11080.1
>Glyma08g11090.1
>Glyma08g11100.1
>Glyma08g11110.1
>Glyma08g11120.1
>Glyma08g11130.1
>Glyma08g11140.1
>Glyma08g11150.1
>Glyma08g11160.1
>Glyma08g11170.1
>Glyma08g11180.1
>Glyma08g11190.1
>Glyma08g11200.1
>Glyma08g11210.1
>Glyma08g11220.1
>Glyma08g11230.1
>Glyma08g11240.1
>Glyma08g11250.1
>Glyma08g11260.1
>Glyma08g11270.1
>Glyma08g11280.1
>Glyma08g11290.1
>Glyma08g11300.1
>Glyma08g11310.1
>Glyma08g11320.1
>Glyma08g11330.1
>Glyma08g11340.1
>Glyma08g11350.1
>Glyma08g11360.1
>Glyma08g11370.1
>Glyma08g11380.1
>Glyma08g11390.1
>Glyma08g11400.1
>Glyma08g11410.1
>Glyma08g11420.1
>Glyma08g11430.1
>Glyma08g11440.1
>Glyma08g11450.1
>Glyma08g11450.2

>Glyma08g11460.1
>Glyma08g11470.1
>Glyma08g11480.1
>Glyma08g11490.1
>Glyma08g11490.2
>Glyma08g11500.1
>Glyma08g11510.1
>Glyma08g11520.1
>Glyma08g11530.1
>Glyma08g11540.1
>Glyma08g11550.1
>Glyma08g11550.2
>Glyma08g11550.3
>Glyma08g11560.1
>Glyma08g11570.1
>Glyma08g11580.1
>Glyma08g11590.1
>Glyma08g11600.1
>Glyma08g11610.1
>Glyma08g11620.1
>Glyma08g11630.1
>Glyma08g11630.2
>Glyma08g11630.3
>Glyma08g11640.1
>Glyma08g11650.1
>Glyma08g11660.1
>Glyma08g11670.1
>Glyma08g11680.1
>Glyma08g11680.2
>Glyma08g11680.3
>Glyma08g11710.1
>Glyma08g11720.1
>Glyma08g11730.1
>Glyma08g11740.1
>Glyma08g11760.1
>Glyma08g11770.1
>Glyma08g11770.2
>Glyma08g11770.3
>Glyma08g11780.1
>Glyma08g11790.1
>Glyma08g11790.2
>Glyma08g11800.1
>Glyma08g11810.1
>Glyma08g11820.1
>Glyma08g11830.1
>Glyma08g11840.1
>Glyma08g11850.1
>Glyma08g11850.2
>Glyma08g11860.1

FIG. 9 (cont.)

| | | |
|---|---|---|
| >Glyma08g11870.1 | >Glyma08g12250.1 | >Glyma08g12690.1 |
| >Glyma08g11880.1 | >Glyma08g12260.1 | >Glyma08g12700.1 |
| >Glyma08g11890.1 | >Glyma08g12270.1 | >Glyma08g12710.1 |
| >Glyma08g11900.1 | >Glyma08g12280.1 | >Glyma08g12720.1 |
| >Glyma08g11910.1 | >Glyma08g12290.1 | >Glyma08g12730.1 |
| >Glyma08g11920.1 | >Glyma08g12300.1 | >Glyma08g12740.1 |
| >Glyma08g11930.1 | >Glyma08g12310.1 | >Glyma08g12750.1 |
| >Glyma08g11940.1 | >Glyma08g12320.1 | >Glyma08g12760.1 |
| >Glyma08g11940.2 | >Glyma08g12330.1 | >Glyma08g12770.1 |
| >Glyma08g11950.1 | >Glyma08g12340.1 | >Glyma08g12780.1 |
| >Glyma08g11960.1 | >Glyma08g12350.1 | >Glyma08g12790.1 |
| >Glyma08g11970.1 | >Glyma08g12360.1 | >Glyma08g12800.1 |
| >Glyma08g11980.1 | >Glyma08g12370.1 | >Glyma08g12810.1 |
| >Glyma08g12000.1 | >Glyma08g12380.1 | >Glyma08g12820.1 |
| >Glyma08g12000.2 | >Glyma08g12390.1 | >Glyma08g12820.2 |
| >Glyma08g12010.1 | >Glyma08g12400.1 | >Glyma08g12830.1 |
| >Glyma08g12020.1 | >Glyma08g12410.1 | >Glyma08g12840.1 |
| >Glyma08g12030.1 | >Glyma08g12420.1 | >Glyma08g12850.1 |
| >Glyma08g12030.2 | >Glyma08g12430.1 | >Glyma08g12860.1 |
| >Glyma08g12040.1 | >Glyma08g12440.1 | >Glyma08g12870.1 |
| >Glyma08g12050.1 | >Glyma08g12450.1 | >Glyma08g12880.1 |
| >Glyma08g12060.1 | >Glyma08g12460.1 | >Glyma08g12890.1 |
| >Glyma08g12070.1 | >Glyma08g12470.1 | >Glyma08g12900.1 |
| >Glyma08g12080.1 | >Glyma08g12480.1 | >Glyma08g12900.2 |
| >Glyma08g12090.1 | >Glyma08g12490.1 | >Glyma08g12910.1 |
| >Glyma08g12090.2 | >Glyma08g12500.1 | >Glyma08g12920.1 |
| >Glyma08g12100.1 | >Glyma08g12510.1 | >Glyma08g12930.1 |
| >Glyma08g12110.1 | >Glyma08g12520.1 | >Glyma08g12940.1 |
| >Glyma08g12120.1 | >Glyma08g12520.2 | >Glyma08g12940.2 |
| >Glyma08g12130.1 | >Glyma08g12530.1 | >Glyma08g12950.1 |
| >Glyma08g12140.1 | >Glyma08g12540.1 | >Glyma08g12960.1 |
| >Glyma08g12140.2 | >Glyma08g12550.1 | >Glyma08g12970.1 |
| >Glyma08g12140.3 | >Glyma08g12560.1 | >Glyma08g12980.1 |
| >Glyma08g12150.1 | >Glyma08g12560.2 | >Glyma08g12980.2 |
| >Glyma08g12150.2 | >Glyma08g12560.3 | >Glyma08g12990.1 |
| >Glyma08g12160.1 | >Glyma08g12570.1 | >Glyma08g13000.1 |
| >Glyma08g12170.1 | >Glyma08g12580.1 | >Glyma08g13010.1 |
| >Glyma08g12180.1 | >Glyma08g12590.1 | >Glyma08g13020.1 |
| >Glyma08g12190.1 | >Glyma08g12600.1 | >Glyma08g13030.1 |
| >Glyma08g12200.1 | >Glyma08g12610.1 | >Glyma08g13040.1 |
| >Glyma08g12210.1 | >Glyma08g12620.1 | >Glyma08g13040.2 |
| >Glyma08g12220.1 | >Glyma08g12630.1 | >Glyma08g13050.1 |
| >Glyma08g12220.2 | >Glyma08g12640.1 | >Glyma08g13060.1 |
| >Glyma08g12220.3 | >Glyma08g12650.1 | >Glyma08g13070.1 |
| >Glyma08g12220.4 | >Glyma08g12650.2 | >Glyma08g13080.1 |
| >Glyma08g12220.5 | >Glyma08g12650.3 | >Glyma08g13090.1 |
| >Glyma08g12220.6 | >Glyma08g12660.1 | >Glyma08g13090.2 |
| >Glyma08g12230.1 | >Glyma08g12670.1 | >Glyma08g13100.1 |
| >Glyma08g12240.1 | >Glyma08g12680.1 | >Glyma08g13110.1 |

FIG. 9 (cont.)

>Glyma08g13110.2
>Glyma08g13120.1
>Glyma08g13130.1
>Glyma08g13130.2
>Glyma08g13140.1
>Glyma08g13150.1
>Glyma08g13160.1
>Glyma08g13170.1
>Glyma08g13180.1
>Glyma08g13180.2
>Glyma08g13190.1
>Glyma08g13200.1
>Glyma08g13210.1
>Glyma08g13220.1
>Glyma08g13220.2
>Glyma08g13230.1
>Glyma08g13240.1
>Glyma08g13240.2
>Glyma08g13240.3
>Glyma08g13250.1
>Glyma08g13260.1
>Glyma08g13270.1
>Glyma08g13280.1
>Glyma08g13290.1
>Glyma08g13300.1
>Glyma08g13300.2
>Glyma08g13300.3
>Glyma08g13300.4
>Glyma08g13310.1
>Glyma08g13320.1
>Glyma08g13330.1
>Glyma08g13340.1
>Glyma08g13340.2
>Glyma08g13350.1
>Glyma08g13360.1
>Glyma08g13370.1
>Glyma08g13380.1
>Glyma08g13390.1
>Glyma08g13400.1
>Glyma08g13410.1
>Glyma08g13420.1
>Glyma08g13430.1
>Glyma08g13440.1
>Glyma08g13440.2
>Glyma08g13450.1
>Glyma08g13450.2
>Glyma08g13460.1
>Glyma08g13470.1
>Glyma08g13480.1

>Glyma08g13490.1
>Glyma08g13500.1
>Glyma08g13510.1
>Glyma08g13520.1
>Glyma08g13520.2
>Glyma08g13530.1
>Glyma08g13540.1
>Glyma08g13550.1
>Glyma08g13560.1
>Glyma08g13560.2
>Glyma08g13570.1
>Glyma08g13580.1
>Glyma08g13590.1
>Glyma08g13600.1
>Glyma08g13610.1
>Glyma08g13620.1
>Glyma08g13630.1
>Glyma08g13630.2
>Glyma08g13640.1
>Glyma08g13650.1
>Glyma08g13660.1
>Glyma08g13670.1
>Glyma08g13680.1
>Glyma08g13690.1
>Glyma08g13700.1
>Glyma08g13720.1
>Glyma08g13730.1
>Glyma08g13740.1
>Glyma08g13740.2
>Glyma08g13740.3
>Glyma08g13740.4
>Glyma08g13750.1
>Glyma08g13760.1
>Glyma08g13770.1
>Glyma08g13780.1
>Glyma08g13790.1
>Glyma08g13800.1
>Glyma08g13810.1
>Glyma08g13820.1
>Glyma08g13830.1
>Glyma08g13840.1
>Glyma08g13850.1
>Glyma08g13860.1
>Glyma08g13870.1
>Glyma08g13880.1
>Glyma08g13890.1
>Glyma08g13900.1
>Glyma08g13910.1
>Glyma08g13910.2

>Glyma08g13910.3
>Glyma08g13920.1
>Glyma08g13930.1
>Glyma08g13930.2
>Glyma08g13940.1
>Glyma08g13950.1
>Glyma08g13960.1
>Glyma08g13970.1
>Glyma08g13980.1
>Glyma08g13980.2
>Glyma08g13990.1
>Glyma08g14000.1
>Glyma08g14010.1
>Glyma08g14020.1
>Glyma08g14030.1
>Glyma08g14040.1
>Glyma08g14050.1
>Glyma08g14060.1
>Glyma08g14070.1
>Glyma08g14080.1
>Glyma08g14090.1
>Glyma08g14100.1
>Glyma08g14110.1
>Glyma08g14120.1
>Glyma08g14130.1
>Glyma08g14130.2
>Glyma08g14140.1
>Glyma08g14150.1
>Glyma08g14160.1
>Glyma08g14170.1
>Glyma08g14180.1
>Glyma08g14190.1
>Glyma08g14200.1
>Glyma08g14210.1
>Glyma08g14220.1
>Glyma08g14230.1
>Glyma08g14240.1
>Glyma08g14250.1
>Glyma08g14250.2
>Glyma08g14260.1
>Glyma08g14270.1
>Glyma08g14280.1
>Glyma08g14280.2
>Glyma08g14280.3
>Glyma08g14280.4
>Glyma08g14280.5
>Glyma08g14290.1
>Glyma08g14300.1
>Glyma08g14310.1

FIG. 9 (cont.)

| | | |
|---|---|---|
| >Glyma08g14320.1 | >Glyma08g14690.1 | >Glyma08g15000.3 |
| >Glyma08g14330.1 | >Glyma08g14700.1 | >Glyma08g15000.4 |
| >Glyma08g14340.1 | >Glyma08g14710.1 | >Glyma08g15000.5 |
| >Glyma08g14350.1 | >Glyma08g14720.1 | >Glyma08g15000.6 |
| >Glyma08g14360.1 | >Glyma08g14720.2 | >Glyma08g15010.1 |
| >Glyma08g14370.1 | >Glyma08g14720.3 | >Glyma08g15010.2 |
| >Glyma08g14380.1 | >Glyma08g14730.1 | >Glyma08g15020.1 |
| >Glyma08g14390.1 | >Glyma08g14740.1 | >Glyma08g15030.1 |
| >Glyma08g14400.1 | >Glyma08g14740.2 | >Glyma08g15040.1 |
| >Glyma08g14410.1 | >Glyma08g14750.1 | >Glyma08g15050.1 |
| >Glyma08g14420.1 | >Glyma08g14750.2 | >Glyma08g15060.1 |
| >Glyma08g14430.1 | >Glyma08g14750.3 | >Glyma08g15070.1 |
| >Glyma08g14440.1 | >Glyma08g14760.1 | >Glyma08g15080.1 |
| >Glyma08g14440.2 | >Glyma08g14770.1 | >Glyma08g15090.1 |
| >Glyma08g14440.3 | >Glyma08g14780.1 | >Glyma08g15090.2 |
| >Glyma08g14440.4 | >Glyma08g14780.2 | >Glyma08g15100.1 |
| >Glyma08g14440.5 | >Glyma08g14790.1 | >Glyma08g15100.2 |
| >Glyma08g14440.6 | >Glyma08g14790.2 | >Glyma08g15110.1 |
| >Glyma08g14450.1 | >Glyma08g14800.1 | >Glyma08g15120.1 |
| >Glyma08g14450.2 | >Glyma08g14810.1 | >Glyma08g15130.1 |
| >Glyma08g14460.1 | >Glyma08g14820.1 | >Glyma08g15140.1 |
| >Glyma08g14460.2 | >Glyma08g14830.1 | >Glyma08g15150.1 |
| >Glyma08g14460.3 | >Glyma08g14830.2 | >Glyma08g15160.1 |
| >Glyma08g14470.1 | >Glyma08g14830.3 | >Glyma08g15170.1 |
| >Glyma08g14480.1 | >Glyma08g14830.4 | >Glyma08g15180.1 |
| >Glyma08g14490.1 | >Glyma08g14830.5 | >Glyma08g15210.1 |
| >Glyma08g14500.1 | >Glyma08g14830.6 | >Glyma08g15210.2 |
| >Glyma08g14510.1 | >Glyma08g14840.1 | >Glyma08g15210.3 |
| >Glyma08g14520.1 | >Glyma08g14840.2 | >Glyma08g15220.1 |
| >Glyma08g14530.1 | >Glyma08g14850.1 | >Glyma08g15230.1 |
| >Glyma08g14540.1 | >Glyma08g14850.2 | >Glyma08g15240.1 |
| >Glyma08g14550.1 | >Glyma08g14860.1 | >Glyma08g15250.1 |
| >Glyma08g14560.1 | >Glyma08g14870.1 | >Glyma08g15260.1 |
| >Glyma08g14570.1 | >Glyma08g14880.1 | >Glyma08g15270.1 |
| >Glyma08g14580.1 | >Glyma08g14890.1 | >Glyma08g15270.2 |
| >Glyma08g14590.1 | >Glyma08g14900.1 | >Glyma08g15280.1 |
| >Glyma08g14590.2 | >Glyma08g14910.1 | >Glyma08g15290.1 |
| >Glyma08g14600.1 | >Glyma08g14920.1 | >Glyma08g15300.1 |
| >Glyma08g14610.1 | >Glyma08g14930.1 | >Glyma08g15310.1 |
| >Glyma08g14620.1 | >Glyma08g14940.1 | >Glyma08g15310.2 |
| >Glyma08g14630.1 | >Glyma08g14940.2 | >Glyma08g15320.1 |
| >Glyma08g14640.1 | >Glyma08g14950.1 | >Glyma08g15330.1 |
| >Glyma08g14650.1 | >Glyma08g14960.1 | >Glyma08g15340.1 |
| >Glyma08g14660.1 | >Glyma08g14970.1 | >Glyma08g15350.1 |
| >Glyma08g14670.1 | >Glyma08g14980.1 | >Glyma08g15360.1 |
| >Glyma08g14670.2 | >Glyma08g14980.2 | >Glyma08g15370.1 |
| >Glyma08g14670.3 | >Glyma08g14990.1 | >Glyma08g15370.2 |
| >Glyma08g14680.1 | >Glyma08g15000.1 | >Glyma08g15370.3 |
| >Glyma08g14680.2 | >Glyma08g15000.2 | >Glyma08g15370.4 |

FIG. 9 (cont.)

>Glyma08g15380.1
>Glyma08g15390.1
>Glyma08g15400.1
>Glyma08g15410.1
>Glyma08g15420.1
>Glyma08g15430.1
>Glyma08g15440.1
>Glyma08g15450.1
>Glyma08g15460.1
>Glyma08g15460.2
>Glyma08g15460.3
>Glyma08g15470.1
>Glyma08g15480.1
>Glyma08g15490.1
>Glyma08g15500.1
>Glyma08g15510.1
>Glyma08g15520.1
>Glyma08g15530.1
>Glyma08g15540.1
>Glyma08g15550.1
>Glyma08g15560.1
>Glyma08g15570.1
>Glyma08g15580.1
>Glyma08g15590.1
>Glyma08g15600.1
>Glyma08g15610.1
>Glyma08g15620.1
>Glyma08g15630.1
>Glyma08g15640.1
>Glyma08g15650.1
>Glyma08g15660.1
>Glyma08g15670.1
>Glyma08g15680.1
>Glyma08g15690.1
>Glyma08g15700.1
>Glyma08g15730.1
>Glyma08g15740.1
>Glyma08g15740.2
>Glyma08g15750.1
>Glyma08g15760.1
>Glyma08g15780.1
>Glyma08g15790.1
>Glyma08g15800.1
>Glyma08g15810.1
>Glyma08g15820.1
>Glyma08g15830.1
>Glyma08g15840.1
>Glyma08g15850.1
>Glyma08g15860.1

>Glyma08g15870.1
>Glyma08g15880.1
>Glyma08g15890.1
>Glyma08g15910.1
>Glyma08g15920.1
>Glyma08g15930.1
>Glyma08g15940.1
>Glyma08g15950.1
>Glyma08g15960.1
>Glyma08g15960.2
>Glyma08g15970.1
>Glyma08g15980.1
>Glyma08g15990.1
>Glyma08g16000.1
>Glyma08g16010.1
>Glyma08g16020.1
>Glyma08g16020.2
>Glyma08g16020.3
>Glyma08g16030.1
>Glyma08g16040.1
>Glyma08g16050.1
>Glyma08g16060.1
>Glyma08g16070.1
>Glyma08g16080.1
>Glyma08g16090.1
>Glyma08g16100.1
>Glyma08g16110.1
>Glyma08g16120.1
>Glyma08g16130.1
>Glyma08g16130.2
>Glyma08g16130.3
>Glyma08g16140.1
>Glyma08g16150.1
>Glyma08g16160.1
>Glyma08g16170.1
>Glyma08g16180.1
>Glyma08g16190.1
>Glyma08g16200.1
>Glyma08g16210.1
>Glyma08g16220.1
>Glyma08g16230.1
>Glyma08g16240.1
>Glyma08g16250.1
>Glyma08g16260.1
>Glyma08g16270.1
>Glyma08g16280.1
>Glyma08g16290.1
>Glyma08g16300.1
>Glyma08g16310.1

>Glyma08g16320.1
>Glyma08g16330.2
>Glyma08g16340.1
>Glyma08g16350.1
>Glyma08g16360.1
>Glyma08g16370.1
>Glyma08g16380.1
>Glyma08g16390.1
>Glyma08g16400.1
>Glyma08g16410.1
>Glyma08g16420.1
>Glyma08g16430.1
>Glyma08g16440.1
>Glyma08g16450.1
>Glyma08g16460.1
>Glyma08g16470.1
>Glyma08g16480.1
>Glyma08g16490.1
>Glyma08g16500.1
>Glyma08g16510.1
>Glyma08g16520.1
>Glyma08g16530.1
>Glyma08g16540.1
>Glyma08g16550.1
>Glyma08g16560.1
>Glyma08g16570.1
>Glyma08g16580.1
>Glyma08g16590.1
>Glyma08g16600.1
>Glyma08g16610.1
>Glyma08g16620.1
>Glyma08g16630.1
>Glyma08g16630.2
>Glyma08g16640.1
>Glyma08g16650.1
>Glyma08g16660.1
>Glyma08g16670.1
>Glyma08g16670.2
>Glyma08g16670.3
>Glyma08g16680.1
>Glyma08g16690.1
>Glyma08g16700.1
>Glyma08g16710.1
>Glyma08g16730.1
>Glyma08g16740.1
>Glyma08g16750.1
>Glyma08g16760.1
>Glyma08g16770.1
>Glyma08g16770.2

FIG. 9 (cont.)

| | |
|---|---|
| >Glyma08g16780.1 | >Glyma08g17200.1 |
| >Glyma08g16790.1 | >Glyma08g17210.1 |
| >Glyma08g16800.1 | >Glyma08g17220.1 |
| >Glyma08g16810.1 | >Glyma08g17230.1 |
| >Glyma08g16820.1 | >Glyma08g17240.1 |
| >Glyma08g16830.1 | >Glyma08g17240.2 |
| >Glyma08g16840.1 | >Glyma08g17250.1 |
| >Glyma08g16850.1 | >Glyma08g17260.1 |
| >Glyma08g16860.1 | >Glyma08g17270.1 |
| >Glyma08g16870.1 | >Glyma08g17280.1 |
| >Glyma08g16870.2 | >Glyma08g17290.1 |
| >Glyma08g16870.3 | >Glyma08g17300.1 |
| >Glyma08g16870.4 | >Glyma08g17310.1 |
| >Glyma08g16880.1 | >Glyma08g17320.1 |
| >Glyma08g16890.1 | >Glyma08g17330.1 |
| >Glyma08g16900.1 | >Glyma08g17340.1 |
| >Glyma08g16900.2 | >Glyma08g17350.1 |
| >Glyma08g16910.1 | >Glyma08g17360.1 |
| >Glyma08g16920.1 | >Glyma08g17370.1 |
| >Glyma08g16930.1 | >Glyma08g17380.1 |
| >Glyma08g16940.1 | >Glyma08g17390.1 |
| >Glyma08g16950.1 | >Glyma08g17400.1 |
| >Glyma08g16960.1 | >Glyma08g17410.1 |
| >Glyma08g16970.1 | >Glyma08g17420.1 |
| >Glyma08g16980.1 | >Glyma08g17450.1 |
| >Glyma08g16990.1 | >Glyma08g17460.1 |
| >Glyma08g17000.1 | >Glyma08g17460.2 |
| >Glyma08g17010.1 | >Glyma08g17460.3 |
| >Glyma08g17010.2 | >Glyma08g17470.1 |
| >Glyma08g17020.1 | >Glyma08g17480.1 |
| >Glyma08g17030.1 | >Glyma08g17490.1 |
| >Glyma08g17040.1 | >Glyma08g17500.1 |
| >Glyma08g17050.1 | >Glyma08g17510.1 |
| >Glyma08g17060.1 | >Glyma08g17520.1 |
| >Glyma08g17070.1 | >Glyma08g17530.1 |
| >Glyma08g17080.1 | >Glyma08g17540.1 |
| >Glyma08g17090.1 | >Glyma08g17550.1 |
| >Glyma08g17100.1 | >Glyma08g17560.1 |
| >Glyma08g17110.1 | >Glyma08g17570.1 |
| >Glyma08g17120.1 | >Glyma08g17580.1 |
| >Glyma08g17120.2 | >Glyma08g17590.1 |
| >Glyma08g17130.1 | >Glyma08g17600.1 |
| >Glyma08g17140.1 | >Glyma08g17610.1 |
| >Glyma08g17160.1 | >Glyma08g17620.1 |
| >Glyma08g17170.1 | >Glyma08g17630.1 |
| >Glyma08g17180.1 | >Glyma08g17640.1 |
| >Glyma08g17180.2 | >Glyma08g17650.1 |
| >Glyma08g17180.3 | >Glyma08g17660.1 |
| >Glyma08g17190.1 | >Glyma08g17670.1 |

FIG. 9 (cont.)

>Glyma18g46750.1
>Glyma18g46760.1
>Glyma18g46780.1
>Glyma18g46790.1
>Glyma18g46800.1
>Glyma18g46810.1
>Glyma18g46820.1
>Glyma18g46830.1
>Glyma18g46840.1
>Glyma18g46850.1
>Glyma18g46860.1
>Glyma18g46870.1
>Glyma18g46880.1
>Glyma18g46890.1
>Glyma18g46900.1
>Glyma18g46910.1
>Glyma18g46920.1
>Glyma18g46930.1
>Glyma18g46940.1
>Glyma18g46950.1
>Glyma18g46960.1
>Glyma18g46970.1
>Glyma18g46980.1
>Glyma18g46990.1
>Glyma18g47000.1
>Glyma18g47010.1
>Glyma18g47020.1
>Glyma18g47030.1
>Glyma18g47040.1
>Glyma18g47050.1
>Glyma18g47060.1
>Glyma18g47070.1
>Glyma18g47080.1
>Glyma18g47090.1
>Glyma18g47100.1
>Glyma18g47110.1
>Glyma18g47120.1
>Glyma18g47130.1
>Glyma18g47140.1
>Glyma18g47150.1
>Glyma18g47160.1
>Glyma18g47170.1
>Glyma18g47180.1
>Glyma18g47190.1
>Glyma18g47200.1
>Glyma18g47210.1
>Glyma18g47220.1
>Glyma18g47230.1
>Glyma18g47240.1

>Glyma18g47250.1
>Glyma18g47260.1
>Glyma18g47270.1
>Glyma18g47280.1
>Glyma18g47290.1
>Glyma18g47300.1
>Glyma18g47310.1
>Glyma18g47320.1
>Glyma18g47330.1
>Glyma18g47340.1
>Glyma18g47350.1
>Glyma18g47360.1
>Glyma18g47370.1
>Glyma18g47380.1
>Glyma18g47390.1
>Glyma18g47400.1
>Glyma18g47410.1
>Glyma18g47420.1
>Glyma18g47430.1
>Glyma18g47440.1
>Glyma18g47450.1
>Glyma18g47460.1
>Glyma18g47470.1
>Glyma18g47480.1
>Glyma18g47490.1
>Glyma18g47500.1
>Glyma18g47500.2
>Glyma18g47510.1
>Glyma18g47520.1
>Glyma18g47530.1
>Glyma18g47540.1
>Glyma18g47550.1
>Glyma18g47560.1
>Glyma18g47570.1
>Glyma18g47580.1
>Glyma18g47590.1
>Glyma18g47600.1
>Glyma18g47610.1
>Glyma18g47620.1
>Glyma18g47630.1
>Glyma18g47640.1
>Glyma18g47650.1
>Glyma18g47660.1
>Glyma18g47670.1
>Glyma18g47690.1
>Glyma18g47700.1
>Glyma18g47710.1
>Glyma18g47720.1
>Glyma18g47730.1

FIG. 10

>Glyma18g47740.1
>Glyma18g47750.1
>Glyma18g47760.1
>Glyma18g47770.1
>Glyma18g47780.1
>Glyma18g47790.1
>Glyma18g47800.1
>Glyma18g47800.2
>Glyma18g47810.1
>Glyma18g47820.1
>Glyma18g47830.1
>Glyma18g47840.1
>Glyma18g47850.1
>Glyma18g47860.1
>Glyma18g47870.1
>Glyma18g47880.1
>Glyma18g47880.2
>Glyma18g47890.1
>Glyma18g47900.1
>Glyma18g47910.1
>Glyma18g47920.1
>Glyma18g47930.1
>Glyma18g47940.1
>Glyma18g47950.1
>Glyma18g47960.1
>Glyma18g47970.1
>Glyma18g47980.1
>Glyma18g47990.1
>Glyma18g48000.1
>Glyma18g48010.1
>Glyma18g48020.1
>Glyma18g48030.1
>Glyma18g48040.1
>Glyma18g48050.1
>Glyma18g48060.1
>Glyma18g48070.1
>Glyma18g48080.1
>Glyma18g48090.1
>Glyma18g48100.1
>Glyma18g48110.1
>Glyma18g48120.1
>Glyma18g48130.1
>Glyma18g48140.1
>Glyma18g48150.1
>Glyma18g48160.1
>Glyma18g48170.1
>Glyma18g48180.1
>Glyma18g48190.1
>Glyma18g48200.1

>Glyma18g48210.1
>Glyma18g48220.1
>Glyma18g48230.1
>Glyma18g48240.1
>Glyma18g48250.1
>Glyma18g48260.1
>Glyma18g48270.1
>Glyma18g48280.1
>Glyma18g48290.1
>Glyma18g48300.1
>Glyma18g48310.1
>Glyma18g48320.1
>Glyma18g48330.1
>Glyma18g48340.1
>Glyma18g48350.1
>Glyma18g48360.1
>Glyma18g48370.1
>Glyma18g48380.1
>Glyma18g48400.1
>Glyma18g48410.1
>Glyma18g48420.1
>Glyma18g48430.1
>Glyma18g48440.1
>Glyma18g48450.1
>Glyma18g48460.1
>Glyma18g48470.1
>Glyma18g48480.1
>Glyma18g48490.1
>Glyma18g48500.1
>Glyma18g48520.1
>Glyma18g48520.2
>Glyma18g48530.1
>Glyma18g48540.1
>Glyma18g48550.1
>Glyma18g48560.1
>Glyma18g48570.1
>Glyma18g48580.1
>Glyma18g48590.1
>Glyma18g48600.1
>Glyma18g48610.1
>Glyma18g48620.1
>Glyma18g48630.1
>Glyma18g48640.1
>Glyma18g48650.1
>Glyma18g48660.1
>Glyma18g48670.1
>Glyma18g48680.1

FIG. 10 (cont.)

>Glyma10g34810.2
>Glyma10g34810.3
>Glyma10g34820.1
>Glyma10g34830.1
>Glyma10g34840.1
>Glyma10g34850.1
>Glyma10g34860.1
>Glyma10g34870.1
>Glyma10g34880.1
>Glyma10g34890.1
>Glyma10g34900.1
>Glyma10g34910.1
>Glyma10g34920.1
>Glyma10g34930.1
>Glyma10g34940.1
>Glyma10g34950.1
>Glyma10g34960.1
>Glyma10g34970.1
>Glyma10g34980.1
>Glyma10g34990.1
>Glyma10g35000.1
>Glyma10g35010.1
>Glyma10g35010.2
>Glyma10g35020.1
>Glyma10g35030.1
>Glyma10g35030.2
>Glyma10g35040.1
>Glyma10g35040.2
>Glyma10g35050.1
>Glyma10g35060.1
>Glyma10g35070.1
>Glyma10g35080.1
>Glyma10g35090.1
>Glyma10g35090.2
>Glyma10g35100.1
>Glyma10g35110.1
>Glyma10g35120.1
>Glyma10g35130.1
>Glyma10g35130.2
>Glyma10g35130.3
>Glyma10g35140.1
>Glyma10g35160.1
>Glyma10g35160.2
>Glyma10g35160.3
>Glyma10g35160.4
>Glyma10g35160.5
>Glyma10g35160.6
>Glyma10g35170.1
>Glyma10g35180.1
>Glyma10g35180.2

>Glyma10g35190.1
>Glyma10g35190.2
>Glyma10g35210.1
>Glyma10g35210.2
>Glyma10g35220.1
>Glyma10g35230.1
>Glyma10g35230.2
>Glyma10g35230.3
>Glyma10g35240.1
>Glyma10g35250.1
>Glyma10g35260.1
>Glyma10g35270.1
>Glyma10g35270.2
>Glyma10g35280.1
>Glyma10g35280.2
>Glyma10g35290.1
>Glyma10g35300.1
>Glyma10g35300.2
>Glyma10g35300.3
>Glyma10g35310.1
>Glyma10g35310.2
>Glyma10g35320.1
>Glyma10g35320.2
>Glyma10g35330.1
>Glyma10g35340.1
>Glyma10g35350.1
>Glyma10g35360.1
>Glyma10g35370.1
>Glyma10g35380.1
>Glyma10g35390.1
>Glyma10g35400.1
>Glyma10g35410.1
>Glyma10g35430.1
>Glyma10g35440.1
>Glyma10g35450.1
>Glyma10g35450.2
>Glyma10g35460.1
>Glyma10g35470.1
>Glyma10g35480.1
>Glyma10g35490.1
>Glyma10g35490.2
>Glyma10g35500.1
>Glyma10g35510.1
>Glyma10g35520.1
>Glyma10g35520.2
>Glyma10g35530.1
>Glyma10g35540.1
>Glyma10g35550.1
>Glyma10g35560.1
>Glyma10g35560.2

FIG. 11

>Glyma10g35570.1
>Glyma10g35580.1
>Glyma10g35590.1
>Glyma10g35600.1
>Glyma10g35610.1
>Glyma10g35620.1
>Glyma10g35630.1
>Glyma10g35640.1
>Glyma10g35650.1
>Glyma10g35660.1
>Glyma10g35660.2
>Glyma10g35670.1
>Glyma10g35680.1
>Glyma10g35680.2
>Glyma10g35680.3
>Glyma10g35680.4
>Glyma10g35690.1
>Glyma10g35690.2
>Glyma10g35690.3
>Glyma10g35700.1
>Glyma10g35710.1
>Glyma10g35720.1
>Glyma10g35730.1
>Glyma10g35740.1
>Glyma10g35740.2
>Glyma10g35740.3
>Glyma10g35740.4
>Glyma10g35740.5
>Glyma10g35750.1
>Glyma10g35760.1
>Glyma10g35770.1
>Glyma10g35800.1
>Glyma10g35810.1
>Glyma10g35810.2
>Glyma10g35820.1
>Glyma10g35820.2
>Glyma10g35830.1
>Glyma10g35830.2
>Glyma10g35830.3
>Glyma10g35830.4
>Glyma10g35830.5
>Glyma10g35840.1
>Glyma10g35850.1
>Glyma10g35860.1
>Glyma10g35870.1
>Glyma10g35870.2
>Glyma10g35880.1
>Glyma10g35890.1
>Glyma10g35890.2
>Glyma10g35900.1
>Glyma10g35900.2
>Glyma10g35900.3
>Glyma10g35910.1
>Glyma10g35920.1
>Glyma10g35930.1
>Glyma10g35930.2
>Glyma10g35940.1
>Glyma10g35950.1
>Glyma10g35950.2
>Glyma10g35950.3
>Glyma10g35950.4
>Glyma10g35960.1
>Glyma10g35960.2
>Glyma10g35970.1
>Glyma10g35980.1
>Glyma10g35990.1
>Glyma10g36000.1
>Glyma10g36010.1
>Glyma10g36020.1
>Glyma10g36030.1
>Glyma10g36040.1
>Glyma10g36040.2
>Glyma10g36050.1
>Glyma10g36060.1
>Glyma10g36070.1
>Glyma10g36080.1
>Glyma10g36090.1
>Glyma10g36100.1
>Glyma10g36100.2
>Glyma10g36110.1
>Glyma10g36120.1
>Glyma10g36130.1
>Glyma10g36140.1
>Glyma10g36150.1
>Glyma10g36160.1
>Glyma10g36170.1
>Glyma10g36180.1
>Glyma10g36190.1
>Glyma10g36200.1
>Glyma10g36210.1
>Glyma10g36220.1
>Glyma10g36230.1
>Glyma10g36240.1
>Glyma10g36250.1
>Glyma10g36260.1
>Glyma10g36270.1
>Glyma10g36280.1
>Glyma10g36290.1
>Glyma10g36290.2
>Glyma10g36290.3

FIG. 11 (cont.)

>Glyma10g36300.1
>Glyma10g36310.1
>Glyma10g36320.1
>Glyma10g36330.1
>Glyma10g36340.1
>Glyma10g36350.1
>Glyma10g36360.1
>Glyma10g36370.1
>Glyma10g36380.1
>Glyma10g36390.1
>Glyma10g36400.1
>Glyma10g36410.1
>Glyma10g36420.1
>Glyma10g36420.2
>Glyma10g36430.1
>Glyma10g36440.1
>Glyma10g36450.1
>Glyma10g36460.1
>Glyma10g36470.1
>Glyma10g36480.1
>Glyma10g36490.1
>Glyma10g36490.2
>Glyma10g36500.1
>Glyma10g36500.2
>Glyma10g36510.1
>Glyma10g36520.1
>Glyma10g36530.1
>Glyma10g36540.1
>Glyma10g36550.1
>Glyma10g36560.1
>Glyma10g36570.1
>Glyma10g36580.1
>Glyma10g36580.2
>Glyma10g36580.3
>Glyma10g36590.1
>Glyma10g36600.1
>Glyma10g36600.2
>Glyma10g36610.1
>Glyma10g36610.2
>Glyma10g36610.3
>Glyma10g36620.1
>Glyma10g36630.1
>Glyma10g36640.1
>Glyma10g36650.1
>Glyma10g36670.1
>Glyma10g36680.1
>Glyma10g36690.1
>Glyma10g36700.1
>Glyma10g36710.1
>Glyma10g36720.1

>Glyma10g36730.1
>Glyma10g36740.1
>Glyma10g36750.1
>Glyma10g36760.1
>Glyma10g36770.1
>Glyma10g36780.1
>Glyma10g36790.1
>Glyma10g36800.1
>Glyma10g36810.1
>Glyma10g36820.1
>Glyma10g36830.1
>Glyma10g36840.1
>Glyma10g36850.1
>Glyma10g36860.1
>Glyma10g36870.1
>Glyma10g36880.1
>Glyma10g36880.2
>Glyma10g36880.3
>Glyma10g36890.1
>Glyma10g36900.1
>Glyma10g36910.1
>Glyma10g36920.1
>Glyma10g36930.1
>Glyma10g36940.1
>Glyma10g36940.2
>Glyma10g36950.1
>Glyma10g36960.1
>Glyma10g36970.1
>Glyma10g36980.1
>Glyma10g36990.1
>Glyma10g36990.2
>Glyma10g37000.1
>Glyma10g37010.1
>Glyma10g37020.1
>Glyma10g37030.1
>Glyma10g37040.1
>Glyma10g37050.1
>Glyma10g37060.1
>Glyma10g37070.1
>Glyma10g37070.2
>Glyma10g37080.1
>Glyma10g37090.1
>Glyma10g37090.2
>Glyma10g37100.1
>Glyma10g37100.2
>Glyma10g37110.1
>Glyma10g37120.1
>Glyma10g37130.1
>Glyma10g37140.1
>Glyma10g37140.2

FIG. 11 (cont.)

>Glyma10g37150.1
>Glyma10g37160.1
>Glyma10g37180.1
>Glyma10g37190.1
>Glyma10g37200.1
>Glyma10g37210.1
>Glyma10g37220.1
>Glyma10g37230.1
>Glyma10g37240.1
>Glyma10g37250.1
>Glyma10g37260.1
>Glyma10g37270.1
>Glyma10g37280.1
>Glyma10g37290.1
>Glyma10g37300.1
>Glyma10g37310.1
>Glyma10g37320.1
>Glyma10g37330.1
>Glyma10g37340.1
>Glyma10g37350.1
>Glyma10g37360.1
>Glyma10g37370.1
>Glyma10g37380.1
>Glyma10g37390.1
>Glyma10g37400.1
>Glyma10g37410.1
>Glyma10g37420.1
>Glyma10g37430.1
>Glyma10g37440.1
>Glyma10g37450.1
>Glyma10g37460.1
>Glyma10g37470.1
>Glyma10g37480.1
>Glyma10g37490.1
>Glyma10g37500.1
>Glyma10g37510.1

FIG. 11 (cont.)

QTL 1 Sat_210 Gm18:1621167..1621420 (SEQ ID No. 1)
QTL 1 Satt610 Gm18:2664941..2665159 (SEQ ID No. 2)
QTL 2 Sat_212 Gm08:9166013..9166312 (SEQ ID No. 3)
QTL 2 AW132402 Gm08:11868922..11869071 (SEQ ID No. 4)
QTL 3 Satt665 Gm11:36229108..36229369 (SEQ ID No. 5)
QTL 3 Satt484 Gm11:38707994..38708296 (SEQ ID No. 6)
QTL 4 GMGLPSI2 Gm20:41872927..41873044 (SEQ ID No. 7)
QTL 4 Sct_189 Gm20:45550533..45550697 (SEQ ID No. 8)
QTL 5 Sct_187 Gm18:60463046..60463189 (SEQ ID No. 9)
QTL 5 Sat_372 Gm18:61095349..61095649 (SEQ ID No. 10)
QTL 6 Satt294 Gm04:40154806..40155092 (SEQ ID No. 11)
QTL 6 Sat_207 Gm04:42773904..42774138 (SEQ ID No. 12)
QTL 7 Satt565 Gm04:511086..511274 (SEQ ID No. 13)
QTL 7 Satt194 Gm04:2402304,2402538 (SEQ ID No. 14)
QTL 8 Satt163 Gm18:998312..998557 (SEQ ID No. 15)
QTL 8 Satt217 Gm18:4692233..4692481 (SEQ ID No. 16)
QTL 9 Sat_406 Gm08:3987571..3987785 (SEQ ID No. 17)
QTL 9 Satt341 Gm08:13199923..13200142 (SEQ ID No. 18)
QTL 10 Satt612 Gm18:56453661..56453904 (SEQ ID No. 19)
QTL 10 Satt472 Gm18:58136158..58136436 (SEQ ID No. 20)
QTL 11 Satt592 Gm10:42983781..42984021 (SEQ ID No. 21)
QTL 11 Sat_038 Gm10:45480355..45480599 (SEQ ID No. 22)

FIG. 12

QUANTITATIVE TRAIT LOCI ASSOCIATED WITH SOYBEAN CYST NEMATODE RESISTANCE AND METHODS OF THEIR USE

RELATED APPLICATIONS

This application claims priority of U.S. Provisional Application No. 61/278,233 filed on Oct. 2, 2009, the contents of which are hereby incorporated into this application by reference.

GOVERNMENT INTERESTS

This invention was made with government support under grant number 2006-34113-17139 by USDA/CSREES. The government has certain rights in the invention

SEQUENCE LISTING

This application is accompanied by a sequence listing both on paper and in a computer readable form that accurately reproduces the sequences described herein.

BACKGROUND

1. Field of the Invention

The present disclosure relates to identification of quantitative trait loci (QTLs) and gene(s) that confer upon a soybean plant resistance to soybean cyst nematode (SCN) and methods to use these loci and genes to obtain soybean strains that are resistant to SCN.

2. Description of the Related Art

Soybean cyst nematode (SCN), *Heterodera glycines*, is one of the most destructive pests of soybean in the United States and worldwide. Although nematocides may be used to reduce the population of nematodes, the use of nematocides is neither economical nor environmentally friendly. Host plant resistance is an effective approach to control this pest; however, continuously growing the same resistant cultivar(s) may result in SCN population shifts and loss of SCN resistant phenotype.

Since the discovery of SCN in the United States in the 1970s, extensive efforts have been made to identify new SCN resistance sources by screening *Glycine max* plant introductions (PIs) of the USDA soybean germplasm collection (Anand et al. 1988; Arelli et al. 2000; Arelli et al. 1997; Young 1995). Chen et al. (2006) used bioassay to characterize over 120 SCN resistance soybean accessions with SCN races 3, –5, and –14 and reported many PIs including PI 437654, PI 438489B, PI 90763, PI 89772, PI 404198A, and PI 567516C with high resistance levels to multi-races.

Although several SCN resistance quantitative trait loci (QTLs) have been discovered in PI 437654 (Concibido et al., 2004, U.S. Pat. No. 6,096,944 issued to Vierling et al. and U.S. Pat. No. 6,538,175 issued to Webb), many SCN resistance QTLs remain to be identified. More SCN sources of resistance have been evaluated extensively to identify novel QTLs and epistatic effects between QTLs (Wu et al 2009). Among soybean PIs evaluated for SCN resistance, PI 437654, PI 467312, PI 438489B, and PI 567516C have been reported to be highly resistant to multi-races (also known as HG types) of SCN. In addition, PI 567516C is also resistant to a synthetic nematode population LY1 and genetically unique from most other SCN resistant sources, including Peking and PI 88788 that are widely used in current SCN resistant varieties.

SUMMARY

The instrumentalities described herein overcome the problems outlined above and advance the art by providing novel quantitative trait loci (QTLs) which may contain SCN resistance genes. Markers associated with these QTLs may also be used to obtain new soybean strains that are SCN resistant using molecular breeding or transgenic approaches.

More particularly, the disclosure relates to the identification of quantitative trait loci (QTLs) responsible for resistance to multi-SCN races in four soybean plant introductions, PI 437654, PI 467312, PI 438489B, and PI 567516C. These QTLs are mapped to genomic regions on Chrs. 4, 8, 10, 11, 18, and 20 (Table 1). Among the QTLs listed in Table 1, SCN QTLs 4, 5, 6, 7, 10, and 11 have not been previously reported in cultivated soybeans, *Glycine max*. Genomic loci that are proximate to or overlap with SCN QTLs 1-3, 8-9 have been reported in other soybean PIs but not in the PIs used in the present disclosure.

TABLE 1

QTLs underlying SCN resistance identified in new resistant soybean PIs and mapped on different soybean chromosomes (LGs).

| | QTLs | | | | | | |
|---|---|---|---|---|---|---|---|
| Source | 18 (G, rhg1) | 8 (A2, Rhg4) | 11 (B1) | 20 (I) | 18 (G, 2$^{nd}$ locus) | 10 (O) | 4 (C1) |
| PI 437654 | Sat_210-Satt610 (1621167-2665159bp) 134 genes (SCN QTL1) | Sat_212-AW132402 (9166013-11869071bp) 460 genes (SCN QTL2) | Satt665-Satt484 (36229108-38708296bp) 378 genes (SCN QTL3) | GMGLPSI2-Sct_189 (41872927-45550697bp) 505 genes (SCN QTL4) | | | |
| PI 467312 | Sat_210-Satt610 (1621167-2665159bp) 134 genes (SCN QTL1) | | | | Sct_187-Sat_372 (60463046-61095649bp) 93 genes (SCN QTL5) | | |

TABLE 1-continued

QTLs underlying SCN resistance identified in new resistant soybean PIs and mapped on different soybean chromosomes (LGs).

| | QTLs | | | | | | |
|---|---|---|---|---|---|---|---|
| Source | 18 (G, rhg1) | 8 (A2, Rhg4) | 11 (B1) | 20 (I) | 18 (G, $2^{nd}$ locus) | 10 (O) | 4 (C1) |
| PI 438489B | Satt163-Satt217 (998312-4692481bp) 457 genes (SCN QTL8) | Sat 406-Satt341 (3987571-13200142bp) 1421 genes (SCN QTL9) | | | | | Satt565-Satt194 (511086-2402538bp) 295 genes (SCN QTL7) Satt294-Sat__207 (40154806-42774138bp) 207 genes (SCN QTL6) |
| PI 567516C | | | | Satt612-Satt472 (56453661-58136436bp) 194 genes (SCN QTL10) | | Satt592-Sat__038 (42983781-45480599bp) 336 genes (SCN QTL11) | |

In addition, the disclosure provides candidate genes underlying these QTL regions defined by markers flanking the QTLs. Some of these genes may be introduced by marker-assisted selection (MAS) from a resistant plant using gene identification, marker development, transformation, and molecular breeding methods. Preferably, the resistant plant comprises a homozygous genomic fragment of the resistant PI lines. Examples of such resistant PI lines include but are not limited to, PI 437654, PI 467312, PI 438489B, and PI 567516C. The markers may also be utilized for introgressing SCN resistance into non-resistant soybean germplasm.

It is disclosed herein genomic regions (i.e., QTLs) responsible for resistance to multi-SCN races (HG types) in four soybean plant introductions, PI 437654, PI 467312, PI 438489B, and PI 567516C. These QTLs were mapped in genomic regions on chromosomes 4, 8, 10, 11, 18, and 20, respectively. Some of these QTLs have been previously reported, while some have not been reported in other SCN-resistant sources of cultivated soybeans, G. max. In addition, markers developed from these regions may facilitate the development of near-isogenic lines (NILs) using the marker-assisted backcrossing (MAB) approach leading to fine-mapping.

Candidate genes underlying these QTL regions may be cloned by utilizing comprehensive approaches that combine genomics, proteomics and metabolic tools. In one embodiment, these genes, either alone or in combination, may be introduced into a host soybean plant known to be susceptible to SCN. The genes may be placed in a construct and introduced into the host soybean plant by transformation. Transformation may be performed as a number of known soybean transformation methods. In another embodiment, the identity of the gene(s) that may be responsible for nematode resistance may be obtained by a series of deletion experiments wherein a portion of a QTL is removed and tested to determine if the truncated QTL fragments still confer upon nematode resistance to a soybean strain that is otherwise susceptible to nematode infection.

In another embodiment, the present disclosure provides a method of introgressing SCN resistance into non-resistant soybean germplasm. Loci associated with SCN resistance in soybean lines known to be resistant to SCN are used in marker-assisted selection (MAS) during introgession of SCN resistance into elite soybean germplasm. Examples of soybean lines known to be resistant to one or more races of SCN include PI 437654, Peking, PI 90763, PI 467312, PI 438489B, and PI 567516C. The method of the present invention can be used to breed soybeans resistant to all SCN races. The SCN races of particular commercial importance are races 1, 2, 3, 5, 6, 9, and 14.

The present disclosure also provides a number of markers associated with the QTLs which may be useful for plant breeding. It is disclosed here a method for generating a soybean plant by performing a step (a) of determining the presence or absence of a marker gene or a fragment thereof. In one aspect, the marker gene may be one or more of the polynucleotide molecules of SEQ ID Nos. 1-22. Step (a) may be performed using DNA hybridization or PCR. In another aspect, the method may further include a step (b) of introgressing the trait of SCN resistance into an SCN sensitive soybean germplasm, with the step (b) preceding step (a). In yet another aspect, the nucleic acid markers as disclosed herein may be used in soybean lines known to be resistant to one or more SCN races or in lines whose susceptibility to SCN is unknown. For example, the markers may be used in genetic mapping of soybean lines to be used in and/or which have been developed in a breeding program, allowing for marker-assisted selection during introgression of SCN resistance into elite germplasm.

It is also disclosed a number of recombinant inbred lines (RILs) that are resistant to single or multi-race of SCN. These RILs are genetically homozygous lines and are listed in Table 2.

BRIEF DESCRIPTION OF THE DRAWINGS

FIG. 1 lists the genes (SEQ ID Nos. 23-156) identified within SCN QTL1.

FIG. 2 lists the genes (SEQ ID Nos. 157-616) identified within SCN QTL2.

FIG. 3 lists the genes (SEQ ID Nos. 617-994) identified within SCN QTL3.

FIG. 4 lists the genes (SEQ ID Nos. 995-1499) identified within SCN QTL4.

FIG. 5 lists the genes (SEQ ID Nos. 1500-1592) identified within SCN QTL5.

FIG. 6 lists the genes (SEQ ID Nos. 1593-1799) identified within SCN QTL6.

FIG. 7 lists the genes (SEQ ID Nos. 1800-2094) identified within SCN QTL7.

FIG. 8 lists the genes (SEQ ID Nos. 2095-2551) identified within SCN QTL8.

FIG. 9 lists the genes (SEQ ID Nos. 2552-3972) identified within SCN QTL9.

FIG. 10 lists the genes (SEQ ID Nos. 3973-4166) identified within SCN QTL10.

FIG. 11 lists the genes (SEQ ID Nos. 4167-4502) identified within SCN QTL11.

FIG. 12 shows the 22 flanking markers (SEQ ID Nos. 1-22) found to be associated with the 11 QTLs: QTL1-11 as listed in Table 1.

DETAILED DESCRIPTION

Previous studies have suggested that multiple genes with quantitative inheritance patterns may be responsible for soybean resistance to SCN and that different soybean germplasm may contain different SCN resistant genes (Anand and 1Rao Arelli 1989; Guo et al. 2005; Guo et al. 2006b; Mansur et al. 1993; Yue et al. 2001a). This disclosure provides novel QTLs that are associated with SCN resistance in various plant introductions (PIs). SCN resistance genes underlying these QTL regions discovered from these soybean plants may be introduced into other soybean varieties or germplasm using transgenic approaches or by marker-assisted selection (MAS) with genetic markers.

It is to be understood that the materials and methods in this disclosure are taught by way of example, and not by limitation. The disclosed instrumentalities may be broader than the particular methods and materials described herein, which may vary within the skill of the art. It is also to be understood that the terminology used herein is for the purpose of describing particular embodiments only, and is not intended to be limiting. Further, unless defined otherwise, all technical and scientific terms used herein have the same meaning as commonly understood by one of ordinary skill in the related art. The following terminology and grammatical variants are used in accordance with the definitions set out below.

Among several PIs with multi-race resistance, PI 567516C, originating from China (http://www.ars-grin.gov/) has been reported to be resistant to SCN races 1, 2, 3 (Arelli et al. 1997; Xie et al. 1998). PI 567516C is also genetically unique from most other SCN resistant sources, such as Peking and PI 88788 (Chen et al. 2006). In addition, PI 567516C is the only PI identified to be resistant to SCN race LY1 (Young 1998, Arelli and Young 2005, Arelli et al. 2009). Although several SCN resistant PIs have been utilized for the genetic characterization of QTLs associated with SCN resistance, limited information has been gained on quantitative resistance of PI 437654, PI 467312, PI 438489B, and PI 567516C, exotic soybean accessions with broad-based resistance to multiple SCN races.

In this disclosure, different genetic populations are developed by crossing four SCN resistant PIs, namely, PI 437654, PI 467312, PI 438489B, and PI 567516C, with susceptible cultivars, such as Essex, Hutcheson, and Magellan. F2 lines and recombinant inbred lines (RILs) from each of these genetic populations were phenotyped and molecularly genotyped. Genetic linkage analysis and QTL analysis have mapped 12 QTL regions to Chromosomes 4, 8, 10, 11, 18, and 20 (Table 1). Some of these 12 QTLs are unique and have not been reported from other SCN-resistance sources.

More specifically, to identify QTL/gene(s) underlying SCN resistance in these PIs, F2:3 progenies and F6/F7 recombinant inbred lines (RILs) derived from the crosses of Essex×PI 437654, Hutcheson×PI 467312, Magellan×PI 438489B, and Magellan×PI 567516C have been developed using the single seed descent (SSD) method, respectively. These RILs were molecularly genotyped with the simple single repeat (SSR) markers and bio-assayed in greenhouse to identify and map quantitative trait loci (QTL) associated with resistance to different races of soybean cyst nematode (SCN). Greenhouse bioassays may be used to characterize the phenotypes of these mapping populations for six SCN races (PA1, −2, −3, −5, −14, and LY1). Based upon the genetic marker profiling and female index (FI) of equal or less than 10%, several RILs in each cross (listed in Table 2) have been shown to be highly resistant to single or multi-race of SCN. The lines from each cross are from the same generation. Based on a 1-100% scale, a FI of ≤10% is used as a threshold value to select a RIL resistant to either single or multi race of SCN. These SCN resistant inbred lines (germplasm) can be employed for the development of new soybean variety using the marker-assisted breeding (MAB) or conventional breeding methods.

Simple sequence repeats (SSR) and single nucleotide polymorphism (SNP) markers may be used for genotyping these genetic populations. Following genetic linkage analysis using the JoinMap 3.0 program, permutation tests and composite interval mapping (CIM) were performed to identify and map QTL using the MapQTL 5.0 or QTLNetwork 2.0 programs. Performing primary QTL mapping using 250-300 progenies, 12 putative QTL regions on Chromosomes 4, 8, 10, 11, 18, and 20 (corresponding to LGs C1, A2, O, B1, G, and I, respectively) have been detected and mapped. The identity of these QTL has been confirmed by analyzing the F6 or F7 RIL mapping populations and comparing to the sequence information of soybean physical and genetic maps (http://soybase.org/gbrowse).

TABLE 2

Recombinant inbred lines (RILs) with high levels of resistance (FI < 10%) to either single or multi-races of soybean cyst nematode (SCN).

| No | Essex × PI 437654 | | Hutcheson × PI 467312 | | Magellan × PI 437489B | | Magellan × PI 567516C | |
|---|---|---|---|---|---|---|---|---|
| | RIL | Race | RIL | Race | RIL | Race | RIL | Race |
| 1 | EP011 | 1, 2, 3, 14 | 195-007 | 5 | MPB0002 | 5 | MPC0102 | 5 |
| 2 | EP013 | 1, 3 | 195-023 | 3 | MPB0011 | 3, 5 | MPC0136 | 3 |
| 3 | EP015 | 1, 3, 5 | 195-033 | 14 | MPB0461 | 3, 5 | MPC0143 | 2, 5 |

TABLE 2-continued

Recombinant inbred lines (RILs) with high levels of resistance (FI < 10%) to either single or multi-races of soybean cyst nematode (SCN).

| No | Essex × PI 437654 RIL | Race | Hutcheson × PI 467312 RIL | Race | Magellan × PI 437489B RIL | Race | Magellan × PI 567516C RIL | Race |
|---|---|---|---|---|---|---|---|---|
| 4 | EP034 | 2, 3, 5, 14 | 195-037 | 14 | MPB0502 | 3, 5 | MPC0341 | 5 |
| 5 | EP038 | 1, 3 | 195-040 | 14 | MPB0530 | 3, 5 | MPC0373 | LY1 |
| 6 | EP044 | 2, 3, 5 | 195-046 | 14 | MPB0580 | 2 | MPC0422 | 5 |
| 7 | EP049 | 1, 3 | 195-048 | 14 | MPB0663 | 3, 5 | MPC0460 | 5 |
| 8 | EP056 | 1, 3, 5 | 195-052 | 3 | MPB0731 | 1, 5 | MPC0626 | LY1 |
| 9 | EP102 | 1, 2, 3, 5 | 195-060 | 3 | MPB0787 | 2 | MPC0671 | 3 |
| 10 | EP110 | 2, 3 | 195-066 | 3, 14 | MPB0809 | 1, 5 | MPC0711 | 5 |
| 11 | EP117 | 2, 3, 5 | 195-074 | 14 | MPB0816 | 1, 3, 5 | MPC0724 | LY1 |
| 12 | EP139 | 1, 2, 3, 5 | 195-078 | 3 | MPB0819 | 3, 5 | MPC0777 | LY1 |
| 13 | EP155 | 1, 2, 3, 5 | 195-088 | 5 | MPB0855 | 3, 5 | MPC0824 | 5 |
| 14 | EP158 | 1, 3, 5 | 195-094 | 3 | MPB0920 | 3, 5 | MPC0840 | 5 |
| 15 | EP163 | 2, 3, 5, 14 | 195-106 | 5 | MPB0923 | 14 | MPC0960 | 5, LY1 |
| 16 | EP167 | 1, 3, 5 | 195-121 | 3 | MPB0931 | 14 | MPC1004 | 5 |
| 17 | EP194 | 1, 3 | 195-123 | 14 | MPB0990 | 3, 5 | MPC1017 | 5 |
| 18 | EP213 | 1, 3 | 195-150 | 3 | MPB1030 | 1, 3, 5 | MPC1046 | LY1 |
| 19 | EP219 | 1, 3, 5 | 195-155 | 5 | MPB1059 | 5 | MPC1259 | LY1 |
| 20 | EP220 | 2, 3, 5, 14 | 195-162 | 3, 5 | MPB1061 | 1, 3, 5 | MPC1270 | 5 |
| 21 |  |  | 195-168 | 14 | MPB1091 | 5, 14 | MPC1680 | 3 |
| 22 |  |  | 195-194 | 14 | MPB1117 | 3, 5 | MPC1785 | 5 |
| 23 |  |  | 195-198 | 14 | MPB1136 | 3, 5 | MPC1854 | 1, 5 |
| 24 |  |  | 195-200 | 14 | MPB1188 | 3, 5 | MPC1959 | 5 |
| 25 |  |  | 195-207 | 14 | MPB1219 | 1, 3, 5 | MPC2059 | LY1 |
| 26 |  |  | 195-210 | 3, 5 | MPB1288 | 3, 5 | MPC2090 | 5 |
| 27 |  |  | 195-220 | 14 | MPB1376 | 3, 5 |  |  |
| 28 |  |  | 195-223 | 3 | MPB1382 | 5 |  |  |
| 29 |  |  | 195-239 | 14 | MPB1500 | 1, 3, 5 |  |  |
| 30 |  |  |  |  | MPB1532 | 3, 5 |  |  |
| 31 |  |  |  |  | MPB1547 | 2 |  |  |
| 32 |  |  |  |  | MPB1561 | 3, 5 |  |  |
| 33 |  |  |  |  | MPB1594 | 3, 5 |  |  |
| 34 |  |  |  |  | MPB1652 | 5 |  |  |
| 35 |  |  |  |  | MPB1660 | 5 |  |  |

The present disclosure also provides a marker selection method that may prove useful in a soybean breeding program. This marker selection method allows the use of markers-associated selection for one or more loci at any stage of population development in a two-parent population, multiple parent population, or a backcross population. Such populations are described in Fehr, W. R. 1987, Breeding Methods for Cultivar Development, in J. R. Wilcox (ed.) Soybeans: Improvement, Production, and Uses, 2d Ed., the disclosures of which are hereby incorporated herein by reference.

In one aspect, the marker-assisted selection may be performed by in a step-wise fashion whereby different SCN resistance loci are selected in more than one generation. Alternatively, the marker-assisted selection may be performed in a simultaneous fashion whereby one or more loci are selected in the same generation. Marker-assisted selection for SCN resistance may be done before, in conjunction with, or after biological testings, assays and selection for other traits such as seed yield, seed composition, among others.

The DNA from target populations may be obtained from any plant organs, and each DNA sample may represent the genotype of single or multiple plant individuals (including seed).

The present disclosure provides a system and a method for expressing a protein that may enhance a host's capability to resist SCN infection. Although soybean plants are the most preferred host for purpose of this disclosure, the genetic constructs described herein may be introduced into other eukaryotic organisms, if the traits conferred upon these organisms by the constructs are desirable.

The term "transgenic plant" refers to a host plant into which a gene construct has been introduced. A gene construct, also referred to as a construct, an expression construct, or a DNA construct, generally contains as its components at least a coding sequence and a regulatory sequence. A gene construct typically contains at least on component that is foreign to the host plant. For purpose of this disclosure, all components of a gene construct may be from the host plant, but these components are not arranged in the host in the same manner as they are in the gene construct. A regulatory sequence is a non-coding sequence that typically contribute to the regulation of gene expression, at the transcription or translation levels. It is to be understood that certain segments in the coding sequence may be translated but may be later removed from the functional protein. An example of these segments is the so-called signal peptide, which may facilitate the maturation or localization of the translated protein, but is typically removed once the protein reaches its destination. Examples of a regulatory sequence include but are not limited to a promoter, an enhancer, and certain post-transcriptional regulatory elements.

After its introduction into a host plant, a gene construct may exist separately from the host chromosomes. Preferably, the entire gene construct, or at least part of it, is integrated onto a host chromosome. The integration may be mediated by a recombination event, which may be homologous, or non-homologous recombination. The term "express" or "expression" refers to production of RNAs using DNAs as template through transcription or translation of proteins from RNAs or the combination of both transcription and translation. The term "chromosome(s)" may be referred to as "chrs" or "chr."

A "host cell," as used herein, refers to a prokaryotic or eukaryotic cell that contains heterologous DNA which has been introduced into the cell by any means, e.g., electroporation, calcium phosphate precipitation, microinjection, transformation, viral infection, and/or the like. A "host plant" is a plant into which a transgene is to be introduced. A "parental plant" is the original plant into which genetic changes are to be introduced in order to create a genetically altered plant.

A "vector" is a composition for facilitating introduction, replication and/or expression of a selected nucleic acid in a cell. Vectors include, for example, plasmids, cosmids, viruses, yeast artificial chromosomes (YACs), etc. A "vector nucleic acid" is a nucleic acid vector into which heterologous nucleic acid is optionally inserted and which can then be introduced into an appropriate host cell. Vectors preferably have one or more origins of replication, and one or more sites into which the recombinant DNA can be inserted. Vectors often have convenient markers by which cells with vectors can be selected from those without. By way of example, a vector may encode a drug resistance gene to facilitate selection of cells that are transformed with the vector. Common vectors include plasmids, phages and other viruses, and "artificial chromosomes." "Expression vectors" are vectors that comprise elements that provide for or facilitate transcription of nucleic acids which are cloned into the vectors. Such elements may include, for example, promoters and/or enhancers operably coupled to a nucleic acid of interest.

"Plasmids" generally are designated herein by a lower case "p" preceded and/or followed by capital letters and/or numbers, in accordance with standard nomenclatures that are familiar to those of skill in the art. Starting plasmids disclosed herein are either commercially available, publicly available on an unrestricted basis, or can be constructed from available plasmids by routine application of well known, published procedures. Many plasmids and other cloning and expression vectors are well known and readily available to those of skill in the art. Moreover, those of skill readily may construct any number of other plasmids suitable for use as described below. The properties, construction and use of such plasmids, as well as other vectors, is readily apparent to those of ordinary skill upon reading the present disclosure.

When a molecule is identified in or can be isolated from an organism, it can be said that such a molecule is derived from said organism. When two organisms have significant difference in the genetic materials in their respective genomes, these two organisms can be said to be genetically different. For purpose of this disclosure, the term "plant" means a whole plant, a seed, or any organ or tissue of a plant that may potentially develop into a whole plant.

The term "isolated" means that the material is removed from its original environment, such as the native or natural environment if the material is naturally occurring. For example, a naturally-occurring nucleic acid, polypeptide, or cell present in a living animal is not isolated, but the same polynucleotide, polypeptide, or cell separated from some or all of the coexisting materials in the natural system, is isolated, even if subsequently reintroduced into the natural system. Such nucleic acids can be part of a vector and/or such nucleic acids or polypeptides could be part of a composition, and still be isolated in that such vector or composition is not part of its natural environment.

A "recombinant nucleic acid" is one that is made by recombining nucleic acids, e.g., during cloning, DNA evolution or other procedures. A "recombinant polypeptide" is a polypeptide which is produced by expression of a recombinant nucleic acid. An "amino acid sequence" is a polymer of amino acid residues (a protein, polypeptide, etc.) or a character string representing an amino acid polymer, depending on context. Either the given nucleic acid or the complementary nucleic acid can be determined from any specified polynucleotide sequence.

The terms "nucleic acid," or "polynucleotide" refer to a deoxyribonucleotide, in the case of DNA, or ribonucleotide in the case of RNA polymer in either single- or double-stranded form, and unless otherwise specified, encompasses known analogues of natural nucleotides that can be incorporated into nucleic acids in a manner similar to naturally occurring nucleotides. A "polynucleotide sequence" is a nucleic acid which is a polymer of nucleotides (A,C,T,U,G, etc. or naturally occurring or artificial nucleotide analogues) or a character string representing a nucleic acid, depending on context. Either the given nucleic acid or the complementary nucleic acid can be determined from any specified polynucleotide sequence.

A "subsequence" or "fragment" is any portion of an entire sequence of a DNA, RNA or polypeptide molecule, up to and including the complete sequence. Typically a subsequence or fragment comprises less than the full-length sequence, and is sometimes referred to as the "truncated version."

Nucleic acids and/or nucleic acid sequences are "homologous" when they are derived, naturally or artificially, from a common ancestral nucleic acid or nucleic acid sequence. Proteins and/or protein sequences are homologous when their encoding DNAs are derived, naturally or artificially, from a common ancestral nucleic acid or nucleic acid sequence. Similarly, nucleic acids and/or nucleic acid sequences are homologous when they are derived, naturally or artificially, from a common ancestral nucleic acid or nucleic acid sequence. The homologous molecules can be termed homologs. Homology is generally inferred from sequence identity between two or more nucleic acids or proteins (or sequences thereof). The precise percentage of identity between sequences that is useful in establishing homology varies with the nucleic acid and protein at issue, but as little as 25% sequence identity is routinely used to establish homology. Higher levels of sequence identity, e.g., 30%, 40%, 50%, 60%, 70%, 80%, 90%, 95% or 99% or more can also be used to establish homology. Methods for determining sequence identity percentages (e.g., BLASTP and BLASTN using default parameters) are described herein and are generally available.

The terms "identical" or "sequence identity" in the context of two nucleic acid sequences or amino acid sequences of polypeptides refers to the residues in the two sequences which are the same when aligned for maximum correspondence over a specified comparison window. A "comparison window", as used herein, refers to a segment of at least about 20 contiguous positions, usually about 50 to about 200, more usually about 100 to about 150 in which a sequence may be compared to a reference sequence of the same number of contiguous positions after the two sequences are aligned optimally. Methods of alignment of sequences for comparison are well-known in the art. Optimal alignment of sequences for comparison may be conducted by the local homology algorithm of Smith and Waterman (1981) *Adv. Appl. Math.* 2:482; by the alignment algorithm of Needleman and Wunsch (1970) *J. Mol. Biol.* 48:443; by the search for similarity method of Pearson and Lipman (1988) *Proc. Nat. Acad. Sci U.S.A.* 85:2444; by computerized implementations of these algorithms (including, but not limited to CLUSTAL in the PC/Gene program by Intelligentics, Mountain View Calif., GAP, BESTFIT, BLAST, FASTA, and TFASTA in the Wisconsin Genetics Software Package, Genetics Computer Group (GCG), 575 Science Dr., Madison, Wis., U.S.A.); the CLUSTAL program is well described by Higgins and Sharp (1988) *Gene* 73:237-244 and Higgins and Sharp (1989) *CABIOS* 5:151-153; Corpet et al. (1988) *Nucleic Acids Res.* 16:10881-10890; Huang et al (1992) *Computer Applications in the Biosciences* 8:155-165; and Pearson et al. (1994) *Methods in Molecular Biology* 24:307-331. Alignment is also often performed by inspection and manual alignment.

In one class of embodiments, the polypeptides herein are at least 70%, generally at least 75%, optionally at least 80%, 85%, 90%, 98% or 99% or more identical to a reference polypeptide, e.g., those that are encoded by the genes responsible for SCN resistance. Sequence similarity may be measured by BLASTP (or CLUSTAL, or any other available alignment software) using default parameters. Similarly, nucleic acids can also be described with reference to a starting nucleic acid, e.g., they can be 50%, 60%, 70%, 75%, 80%, 85%, 90%, 98%, 99% or more identical to a reference nucleic acid, e.g., those that are set forth by any one of the candidate genes disclosed herein or a fragment thereof, e.g., as measured by BLASTN (or CLUSTAL, or any other available alignment software) using default parameters. When one molecule is said to have certain percentage of sequence identity with a larger molecule, it means that when the two molecules are optimally aligned, said percentage of residues in the smaller molecule finds a match residue in the larger molecule in accordance with the order by which the two molecules are optimally aligned.

In another embodiment, DNA sequences that are substantially identical to the candidate genes may be used to generate a transgenic plant that is more resistant to SCN than the host. The term "substantially identical" as applied to nucleic acid or amino acid sequences means that a nucleic acid or amino acid sequence comprises a sequence that has at least 90% sequence identity or more, preferably at least 95%, more preferably at least 98% and most preferably at least 99%, compared to a reference sequence using the programs described above (preferably BLAST) using standard parameters. For example, the BLASTN program (for nucleotide sequences) uses as defaults a word length (W) of 11, an expectation (E) of 10, M=5, N=−4, and a comparison of both strands. For amino acid sequences, the BLASTP program uses as defaults a word length (W) of 3, an expectation (E) of 10, and the BLOSUM62 scoring matrix (see Henikoff & Henikoff, *Proc. Natl. Acad. Sci. USA* 89:10915 (1989)). Percentage of sequence identity is determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity. Preferably, the substantial identity exists over a region of the sequences that is at least about 50 residues in length, more preferably over a region of at least about 100 residues, and most preferably the sequences are substantially identical over at least about 150 residues. In a most preferred embodiment, the sequences are substantially identical over the entire length of the coding regions.

The term "polypeptide" is used interchangeably with the terms "polypeptides" and "protein(s)", and refers to a polymer of amino acid residues. A 'mature protein' is a protein which is full-length and which, optionally, includes glycosylation or other modifications typical for the protein in a given cellular environment.

The term "variant" or "mutant" with respect to a polypeptide refers to an amino acid sequence that is altered by one or more amino acids with respect to a reference sequence. The variant may have "conservative" changes, wherein a substituted amino acid has similar structural or chemical properties, e.g., replacement of leucine with isoleucine. Alternatively, a variant may have "nonconservative" changes, e.g., replacement of a glycine with a tryptophan. Analogous minor variation can also include amino acid deletion or insertion, or both. Guidance in determining which amino acid residues can be substituted, inserted, or deleted without eliminating biological or immunological activity can be found using computer programs well known in the art, for example, DNASTAR software.

As used herein, the term "resistant" or "resistance" means that the FI (%) between a subject plant and a control plant is 50% or less. More preferably, the transgenic plant or progeny thereof has a FI (%) of 20% or less, even more preferably, at 10% or less. The FI (%) may be calculated as a percentage of number of female cyst nematodes on a subject plant divided by the average number of female nematodes on a control plant, such as Hutcheson (susceptible control) or a host plant after said subject plant and the control plant are grown under comparable condition for a given period of time.

A variety of additional terms are defined or otherwise characterized herein. In practicing the instrumentalities described herein, many conventional techniques in molecular biology, microbiology, and recombinant DNA are optionally used. These techniques are well known to those of ordinary skill in the art. For example, one skilled in the art would be familiar with techniques for in vitro amplification methods, including the polymerase chain reaction (PCR), for the production of the homologous nucleic acids described herein.

The markers that are genetically linked to the QTLs disclosed herein, or other similarly placed markers, may be used in soybean breeding for marker-assisted selection of resistance to different races of SCN, including but not limited to races 1, 2, 3, 5, 14 and LY1.

Selection for resistant strains based on two markers that flank a QTL is generally more reliable than selections based on one marker linked to the QTL. Flanking-marker selection relies on two markers thereby reducing the number of false positive due to recombination between one marker and the QTL, and consequently, reducing the probability selecting a line that is susceptible. It is to be recognized, however, that when markers are closely linked to a QTL, results from single-marker selections may be acceptable.

According to another aspect of the present disclosure, a new phenotypically superior SCN-resistant soybean plant may be produced which possesses desirable traits but is substantially free from undesirable characteristics currently associated with SCN-resistant soybean lines. The first step for producing such an improved soybean line may involve providing one or more plants from a parental soybean plant line which comprises in its genome one or more molecular markers disclosed above that are genetically linked to SCN resistance. Preferably, the parental plant line is purebreeding for one or more of such molecular markers.

The second step in this method comprises introgressing SCN resistance into a recipient soybean plant line which is not resistant or less resistant to SCNs by performing marker-assisted selection based upon the one or more molecular markers in the parent mentioned in the first step. The progeny thus obtained may be backcrossed to obtain a new improved plant having the one or more molecular markers in their genome which are associated with SCN resistance.

Plants thus selected may then be used to develop new SCN-resistant recombinant soybean plant lines, for example, by single seed descent. Alternatively, the plant may optionally be further treated to selective breeding by performing additional backcrosses and selections, based upon the presence of one or more of the markers, for multiple generations. The presence of one or more of the markers may be readily determined by single nucleotide polymorphism (SNP) analysis of the plant's genomic DNA.

Marker-assisted selection may also be used to confirm previous selection for SCN resistance or susceptibility made by challenging plants with SCNs in the field or greenhouse and scoring the resulting phenotypes. Alternatively, plants can be analyzed by SNP analysis to determine the presence of the molecular markers disclosed herein in order to confirm the presence of a genomic locus associated with SCN resistance. This method can be applied to a soybean plant, soybean seeds or other tissues.

With the completion of the soybean genome sequencing project, genes within each QTL may be identified using the genomic information that are publicly available, for example, at the website maintained by NCBI. These genes may be cloned using genomic library or by PCR using genomic DNA, or cDNA as templates.

Alternatively, markers linked to each of the mapped QTL may also be used in positional cloning of genes that reside within those QTL. Positional cloning first involves creating a physical map of a contig (contiguous overlapping of cloned DNA inserts), in the genomic region encompassing one or more marker loci and the target gene. The target gene is then identified and isolated within one or more clones residing in the contig. Having a clone of a gene allows it to be used in genetic studies, transformation, and the development of transgenic plants and novel phenotypes.

It is to be recognized to that resistance to one race of SCN, or to multiple races, is likely to be controlled by more than one gene or more than one genomic locus. Genes found to be associated with SCN resistance can also be introduced into a parental plant by transformation in order to create a transgenic plant carrying the SCN resistance gene(s). Transformation of a plant cell can be accomplished by a variety of different methodology. Methods that have general utility include, for example, *Agrobacterium* based systems, using either binary and/or cointegrate plasmids of both *A. tumifaciens* and *A. rhyzogenies*, (See e.g., U.S. Pat. No. 4,940,838, U.S. Pat. No. 5,464,763), the biolistic approach (See e.g, U.S. Pat. No. 4,945,050, U.S. Pat. No. 5,015,580, U.S. Pat. No. 5,149,655), microinjection, (See e.g., U.S. Pat. No. 4,743,548), direct DNA uptake by protoplasts, (See e.g., U.S. Pat. No. 5,231,019, U.S. Pat. No. 5,453,367) or needle-like whiskers (See e.g., U.S. Pat. No. 5,302,523). Any method for the introduction of foreign DNA or RNA into a plant cell and for expression therein may be used within the context of the present disclosure.

EXAMPLES

The following nonlimiting examples report general procedures, reagents and characterization methods that teach by way of example, and should not be construed in a narrowing manner that limits the disclosure to what is specifically disclosed. Those skilled in the art will understand that numerous modifications may be made and still the result will fall within the spirit and scope of the present invention.

Example 1

Methods and Materials

The following genetic populations were generated using the Single Seed Descent method (RILs stands for Recombinant Inbred Lines):

205 F7:9 RILs of Essex×PI 437654
250 F7:8 RILs of Magellan×PI 437654
230 F7:8 RILs of Hutchison×PI 467312
250 F2:3 progenies of Magellan×PI 4384898
250 F2:3 progenies of Magellan×PI 567516C
250 F6:7 RILs of Magellan×PI 4384898
250 F6:7 RILs of Magellan×PI 567516C Single Seed Descent is a common method to generate recombinant inbred lines (RILs) in genetics study. By way of example, to obtain F6:7 RILs, one would start from a genetically segregating F2 population of a biparent cross. At maturity, one single seed of each F2 plant was harvested and individually recorded, i.e., labeled with an ID. These F2 seeds were grown to produce F3 plants. Again, one single seed of each F3 plant was harvested. The process was repeated until F6 generation was reached. The F6 plants were grown and harvested in bulk. These F6 were grown in row and harvested to generate F7 RILs. At this F7 stage, most of the genes in the genome are homozygous as a result of several generations of genetic recombination.

DNA extraction and molecular marker analysis were performed as described below. Briefly, genomic DNA was isolated from young leaf tissue of the parents, F2 plants, or RILs using an automated DNA extraction instrument AutoGen 960 (AutoGen Inc., Holliston, Mass.) following the CTAB protocol as described by the manufacturer. The DNA concentration was quantified with a spectrophotometer (NanoDrop Technologies Inc., Centreville, Del.) and diluted to concentration of 20 ng/ul for polymerase chain reaction (PCR) amplification of SSR marker analysis and 50 ng/ul for the GoldenGate assays of SNP marker genotyping.

For fluorescent-labeled SSR markers, PCR amplifications were performed in 12.5 ul final volume on Eppendorf 96- or 384-well thermal cyclers (Eppendorf AG, Germany). Each reaction contained 40-50 ng of, genomic DNA, 0.13 uM of forward primer (labeled) and 0.2 uM of reverse primer, 0.2 mM of each dNTP, and 1 unit of Taq DNA polymerase (GenScript Corp., Piscataway, N.J.). The thermal cycler program was performed at 94° C. for 5 min, followed by 35 cycles of denaturation at 94° C. for 30 sec, annealing at 47° C. or 52° C. for 30 sec, and extension at 72° C. for 45 sec. A 10-min extension at 72° C. followed the last cycle. The PCR products were separated using an ABI3100 or 3730 DNA sequencer (ABI Applied BioSystems, Foster City, Calif.).

The allele of each marker was analyzed with GeneMapper 3.7 software (ABI Applied BioSystems, Foster City, Calif.). For SNP markers, the universal soy linkage panel (the USLP 1.0) containing 1,536 SNP loci that were discovered and mapped onto the integrated molecular genetic linkage map as previously described (Hyten et al. 2008) was utilized to genotype F6:7 RTL mapping populations using the Illumina GoldenGate assay (Fan et al. 2006).

A total of 5 ul of 50 ng/ul of RNase-treated genomic DNA sample was activated by biotinylation, followed by the oligonucleotide/target annealing step, in which the SNP-specific oligonucleotide annealed to the activated DNA by ramping the temperature from 70° C. to 30° C. over 2 h. Three oligonucleotide sequences, two allele-specific oligos (ASO) and one locus-specific oligo (LSO) designed for each SNP, contain regions of genomic complementary and universal PCR primer sites. The LSO also contained a unique IllumiCode sequence complementary to a particular bead type. Following the assay oligonucleotide hybridization, wash steps to remove excess and mis-hybridized oligos, and adding a master mix of extension and ligation, the assay of oligonucleotide extension and ligation were implemented at 45° C. for 15 min.

DNA polymerase was used to extend the ASO and fill the gaps between the ASO and LSO; and a DNA ligase was employed to seal the nick between the extended ASO and LSO to form PCR template that can be amplified with three universal PCR primers. These universal primers were 5'-labeled with Cy3, Cy5, and biotin. The PCR amplification was then performed following a thermal cycler program: 10 min at 37° C. followed by 3 min at 95° C.; 34 cyclers of denaturation at 95° C. for 35 sec, annealing at 56° C. for 35 sec, and extension at 72° C. for 2 min. A 10-min extension at 72° C. followed the last cycle.

The resulting double-stranded PCR products were immobilized onto paramagnetic particles followed by steps of washing and denaturing. The released single-stranded DNAs were then hybridized to their complementary bead type through their unique IllumiCode sequence of the Sentrix array matrix (SAM) under a temperature gradient program from 60° C. to 45° C. for at least 12 h. The hybridized SAM was rinsed and dried for 20 min in dark. The array imaging was performed using the Illumina BeadStation (Illumina, San Diego, Calif.).

The allele calling for each SNP locus was conducted with the BeadStudio 3.0 software (Illumina, San Diego, Calif.) based on the intensities detected from the two channels, Cy3 and Cy5, for the two respective alleles of each SNP. The clusters of homozygote and heterozygous genotypes for each SNP were manually checked and identified for polymorphisms between the two parental lines. The polymorphic SNP loci were then employed for the genetic linkage analysis and QTL mapping.

Soybean cyst nematode (SCN) bioassays were performed in the greenhouse at the University of Missouri-Columbia according to established methods (Arelli et al., 1997). All SCN races 1, 2, 3, 5, 14, and LY1 (corresponding to HG types 2.5.7; 1.2.5.7; 0; 1.2.7, 1.3.6.7, and 1.2.5.6.7, respectively) (Niblack et al. 2002) that were used in this Example have been maintained for many generations at the University of Missouri-Columbia (Arelli et al. 1997; Arelli et al. 2000). The population purity of each race and the success of a phenotyping experiment were monitored and evaluated by SCN reaction to indicator lines, Peking, Pickett, PI 88788, PI 90763, PI 437654, PI 209332, PI 89772, PI 548316 and Hutcheson (susceptible control).

More particularly, soybean seeds were germinated for three days in germination pouches and then seedlings were transplanted into micropots (one plant in each micropot) filled with steam-pasteurized sandy soil. Five plants of each indicator lines and five single-plant replications per RIL (two independent experiments for all races) were planted together in random way. Twenty four micropots each were placed in a plastic container and maintained at 27±10° C. in a thermal-regulated water bath. Two days after transplanting, roots of each plant were inoculated with 2000±25 SCN eggs. Thirty days after transplanting, roots were harvested and washed to collect female nematode. Nematode cysts were then counted under a stereo-microscope. The female index (FI) was calculated to evaluate SCN response of each individual seedling of all plants, including parents, F2:3 progenies, RILs, and indicator lines. The FI (%) was calculated as a percentage of number of female cyst nematodes on a given individual divided by the average number of female nematodes on cultivar Hutcheson.

Data processing and analysis were performed as described in the following text. Female index (FI) of F2:3 progenies and RILs were tested for normality using the UNIVARIATE procedure of SAS 9.1 (SAS Institute, Cary, N.Y.). The Shapiro-Wilk (W) statistical method was used to test the null hypothesis that FI (%) were normally distributed among F2:3 progenies or RILs (Elliott 1999). Linkage analysis was performed with the computer program JoinMap 3.0 (van Ooijen and Voorrips 2001) to construct a genetic linkage map using the Kosambi mapping function. A likelihood of odds (LOD) threshold score of 3.0 and a maximum distance of 50 cM were used for initial linkage grouping of markers. Chromosome numbers (Chr.) were assigned according to the designation of the soybean linkage groups (LGs) described in the SoyBase website (http://www.soybase.org) and the soybean composite map (Song et al. 2004). Composite interval mapping (CIM) was performed to identify QTL controlling FI using the MQM method with the program MapQTL 5.0 or QTLNetwork 2.0 and the appropriate cofactor selection (van Ooijen and Voorrips 2001). The permutation test (Churchill and Doerge 1994) was performed with 1000 runs to determine the P=0.05 genome-wide significance level for declaring QTL for FI significant. The proportion of the phenotypic variance explained by the QTL effects was estimated by CIM at the QTL peaks. The total phenotypic variance explained by the significant QTL was determined using a multivariate ANOVA model of SAS.

Molecular genetic linkage analysis was performed using the methodology described below. Nearly 600 fluorescent-labeled SSR markers were surveyed for DNA polymorphisms between two parental lines of each genetic population. Of these, from 250 to 300 markers, which produced mainly co-dominant loci, were polymorphic. These markers were utilized for genotyping of the F2:3 or RIL mapping populations. For each genetic population, a molecular genetic linkage map encompassing 20 soybean chromosomes and fragments was constructed. These chromosomes and fragments covered approximately 1,600 to 2500 cM. Overall, marker order and genetic distance between markers in the constructed genetic map had a linear relationship with the composite linkage map (Song et al. 2004).

Example 2

Identification of QTLs Associated with SCN Resistance in PI 437654

Four major QTLs associated with SCN resistance have been identified in PI 437654 (Table 1). These QTLs may be defined by flanking markers on the genome sequence. The genomic regions encompassed by these QTLs contain many genes encoding proteins or metabolites that may play a role in SCN resistance. These genes may also include networking regulators or transcription factors.

The first QTL ("SCN QTL1") is located on LG G (Chromosome 18) from Sat_210 to Satt610 (i.e. from 1620984 by to 2664659 bp), which contains 134 predicted genes. The gene identifiers of these genes are listed in FIG. 1. The second QTL ("SCN QTL2") is located on LG A2 (Chromosome 8) from Sat_212 to AW132402 (i.e. from 9166105 by to 11868971 bp), including 460 predicted genes. The gene identifiers of these genes are listed in FIG. 2. The third QTL ("SCN QTL3") is located on LG B1 (Chromosome 11) from Satt665 to Satt484 (i.e. from 36229108 by to 38708296 bp). This QTL includes 378 predicted genes, whose identifiers are listed in FIG. 3. The fourth QTL ("SCN QTL4") is located on LG I (Chromosome 20) from GMGIPSI2 to Sct_189 (i.e. from 41872927 by to 45550697 bp), including 505 predicted genes. The gene identifiers of these genes are listed in FIG. 4.

In addition, about 160 genetic markers have been identified within this region which may be used for fine mapping the QTLs with NILs.

Example 3

Identification of QTLs Associated with SCN Resistance in PI 467312

Two QTL regions have been identified for PI 467312 (Table 1). One QTL is identical to the SCN QTL1 as described above. The other QTL ("SCN QTL5") is located on the same Chromosome 18 but is located in a different region, from Sct_187 to Sat_372 (i.e. from 60463046 by to 61095649 bp), including 93 predicted genes. The gene identifiers of these genes are listed in FIG. 5.

Example 4

Identification of QTLs Associated with SCN Resistance in PI 438489B

For 438489B, based on the results of primary QTL mapping in F2:3 progenies and confirmation study in F7 RIL population derived from the Magellan×PI 438489B population, two new QTLs were detected which are associated with resistance to two SCN races, 5 and 14. These two QTLs were mapped to two distinct genomic regions of Chr. 4 (corresponding to LG C1) (Table 1). The first QTL ("SCN QTL6") responsible for resistance to race 5 (also called "R5-QTL") was flanked by the SSR markers Satt294 and Sat_207 with LOD score of 7.5. A favorable allele from PI 438489B conferred greater resistance and had an additive effect on the race 5 SCN female index (FI). In reference to the soybean physical map (http://soybeanphysicalmap.org) and the 8× assembly sequence information of the soybean genome (http://www-.phytozome.net), the R5-QTL was in the supercontig 111 and was physically positioned between 40154806 and 42774138 bp. At least 207 soybean genes were predicted to exist within this genomic location, based on gene annotation (Table 1 and FIG. 6).

The second QTL ("SCN QTL7") is also on chromosome 4 and is for resistance to race 14 (tentatively designated R14-QTL). This QTL was flanked by the SSR markers Satt565 and Satt194 with LOD score of 8.5. A favorable allele from PI 438489B conferred greater resistance and had an additive effect on FI. The R14-QTL was in the supercontig 170 and is physically positioned between 511086 and 2402538 bp. 295 soybean genes were predicted to exist within this genomic location based on gene annotation (Table 1). The gene identifiers of these genes are listed in FIG. 7.

Also from this population, two previously identified QTLs were detected and mapped on Chrs. 18 and 8 (corresponding to LGs G and A2, respectively). The first of the two previously identified QTLs ("SCN QTL8") was concurrently responsible for resistance to three races 1, 2, and 3 with LOD scores of 8.0, 7.5, and 16.0, respectively, and flanked by the SSR markers Satt163 and Satt217. A favorable allele from PI 438489B conferred greater resistance and had an additive effect on all SCN female index (FI). The "SCN QTL8" was in the supercontig 110 and physically positioned between 998312 and 4692481 by (http://www.phytozome.net). This genomic region contains 457 soybean genes predicted according to gene annotation. The gene identifiers of these genes are listed in FIG. 8.

The second of the two previously identified QTLs ("SCN QTL9") was also concurrently associated with resistance to races 1 and 3 with LOD scores of 4.7 and 10.2, respectively, and flanked by the SSR markers Sat_406 and Satt341. A favorable allele from PI 438489B conferred greater resistance and had an additive effect on all SCN female index (FI). The "SCN QTL9" was in the supercontig 5 and physically positioned between 3987571-13200142 bp by on Chr. 8 (http://www.phytozome.net). Within the genomic region, 1421 genes were predicted based on gene annotation. The gene identifiers of these genes are listed in FIG. 9.

Example 5

Identification of QTLs Associated with SCN Resistance in PI 567516C

Based on the results of primary QTL mapping in F2:3 progenies and confirmation study in the F7 RIL population, two new QTLs were detected in PI 567516C which were significantly associated with resistance to multi-races of SCN and were mapped to Chrs. 18 and 10 (corresponding to LGs G and O, respectively) (Table 1). The first QTL ("SCN QTL10") was located on a new genomic region flanked by the SSR markers Satt612 and Satt472 on Chr. 18 (LG G) with LOD scores of 6.5, 7.2, 3.8, 10.3, and 6.3 for races 1, 2, 3, 5, and LY1, respectively. Favorable alleles from PI 567516C conferred greater resistance and had an additive effect on FI. In reference to the soybean physical map (http://soybeanphysicalmap.org) and the 8× assembly sequence information of the soybean genome (http://www.phytozome.net), this QTL was located in supercontig 8 and was physically positioned between 56453661 and 58136436 bp, in which six SNP loci of the USLP 1.0 soybean array were found to be closely associated with the QTL. In addition, 194 soybean genes were predicted to lie within this genomic region based on gene annotation data (Table 1). The gene identifiers of these genes are listed in FIG. 10.

The second QTL ("SCN QTL11") was mapped to a new genomic region flanked by the SSR markers Sat_038 and Satt592 on Chr. 10. Between these two markers, the marker Sat331 was closely associated with the QTL peak, with LOD scores of 6.6, 8.2, 4.2, 7.0, and 11.7 for races 1, 3, 5, 14, and LY1, respectively. A favorable allele was inherited from PI 567156C and had an additive effect on FI. In reference to the soybean physical map (http://soybeanphysicalmap.org) and the 8× assembly sequence information of the soybean genome (http://www.phytozome.net), this QTL was in the supercontig 124 and was physically positioned between 42983781 and 45480599 bp, in which five SNP loci of the USLP 1.0 soybean array were found to be closely associated with the QTL. In addition, 336 soybean genes were predicted to exist within this genomic region based on the gene annotation (Table 1). The gene identifiers of these genes are listed in FIG. 11.

Example 6

Characterization of the QTLs to Identify Individual Genes Responsible for SCN Resistance All QTLs identified in the Examples above are summarized in Table 1. Gene identifiers of those flanking markers (SEQ ID Nos. 1-22) associated with these QTLs are listed in FIG. 12. Many other markers may also exist within each QTL which may be useful in fine-mapping the loci responsible for SCN resistance.

A series of different soybean populations may be developed to facilitate fine mapping. An integrated approach may be applied to these fine mapping populations to pinpoint candidate genes associated with SCN resistance and narrow down the QTL regions until resistance genes underlying these QTL regions are cloned. Individual genes shown to be responsible for SCN resistance are introduced into soybean strains that are susceptible to SCN infection.

All genes encompassed by the QTLs listed in Table 1 and described in the Examples above are listed by their gene identifiers in FIGS. 1-11. The sequences of these genes may be obtained from publicly available databases and are hereby incorporated expressly into this disclosure by reference. Examples of such databases include by are not limited to GenBank maintained by NCBI, as well as soybean specific databases at the following link: http://soybase.org.

While the foregoing instrumentalities have been described in some detail for purposes of clarity and understanding, it will be clear to one skilled in the art from a reading of this disclosure that various changes in form and detail can be made without departing from the true scope of the invention. For example, all the techniques and apparatus described above may be used in various combinations. All publications, patents, patent applications, or other documents cited in this application are incorporated by reference in their entirety for all purposes to the same extent as if each individual publication, patent, patent application, or other document were individually indicated to be incorporated by reference for all purposes.

REFERENCES

In addition to those references that are cited in the text, additional information for those abbreviated citations is listed below. The content of all patents, patent applications or other publications cited in this disclosure are incorporated by reference into this disclosure.

1 Anand S C, Gallo K M, Baker I A, Hartwig E E (1988) Soybean plant introductions with resistance to races 4 or 5 of soybean cyst nematode. Crop Sci 28:563-564.
2 Anand S C, Rao Arelli A P (1989) Genetic analyses of soybean genotypes resistant to soybean cyst nematode race 5. Crop Sci 29:1181-1184.
3 Arelli P R, Sleper D A, Yue P, Wilcox J A (2000) Soybean reaction to races 1 and 2 of *Heterodera glycines*. Crop Sci 40:824-826.
4 Arelli P R, Wilcox J A, Myers J, Gibson P T (1997) Soybean germplasm resistant to races 1 and 2 of *Heterodera glycines*. Crop Sci 37:1367-1369.
5 Arelli P R, Young I D (2005) Genetics of resistance in soybean PI 567516C to LY1 nematode population infecting cv. Hartwig. Crop Sci Soc Am p. 234 (Abstracts).
6 Arelli P R, Young I D, Concibido V C (2009) Inheritance of resistance in soybean PI 567516C to LY1 nematode population infecting cv. Hartwig. Euphytica 165:1-4.
7 Caldwell B E, Brim C A, Ross J P (1960) Inheritance of resistance of soybeans to the cyst nematode, *Heterodera glycines*. Agron J 52:635-636.
8 Chen Y, Wang D, Arelli P R, Ebrahimi M, Nelson R I (2006) Molecular marker diversity of SCN-resistant sources in soybean. Genome 49:938-949.
9 Churchill G A, Doerge R W (1994) Empirical threshold values for quantitative trait mapping. Genetics 138:963-971.
10 Concibido V C, Denny R I, Boutin S R, Hautea R, Orf J H, Young N D (1994) DNA marker analysis of loci underlying resistance to soybean cyst nematode (*Heterodera glycines* Ichinohe). Crop Sci 34:240-246.
11 Concibido V C, Denny R I, lange D A, Orf J H, Young N D (1996) RFIP mapping and marker-assisted selection of soybean cyst nematode resistance in PI 209332. Crop Sci 36:1643-1650.
12 Concibido V C, Diers B W, Arelli P R (2004) A decade of QTL mapping for cyst nematode resistance in soybean. Crop Sci 44:1121-1131.
13 Cregan P B, Mudge J, Fickus E W, Danesh D, Denny R, Young N D (1999) Two simple sequence repeat markers to select for soybean cyst nematode resistance conditioned by the rhg1 locus. Theor Appl Genet 99:811-818.
14 Elliott R J (1999) learning SAS in the computer lab (2nd Ed.) Duxbury Thomson learning, USA:39-48.
15 Fan J, Gunderson K, Bibikova M, Yeakley J, Chen J, Garcia E W, lebruska l, laurent M, Shen R, Barker D (2006) Iliumina universal bead Methods 410:57-73.
16 Guo B, Sleper D A, Arelli P R, Shannon J G, Nguyen H T (2005) Identification of QTLs associated with resistance to soybean cyst nematode races 2, 3 and 5 in soybean PI 90763. Theor Appl Genet 111:965-971.
17 Guo B, Sleper D A, Nguyen H T, Arelli P R, Shannon J G (2006b) Quantitative trait loci underlying resistance to three soybean cyst nematode populations in soybean PI 404198A. Crop Sci 46:224-233.
18 Hyten D, Song Q, Choi I, Yoon M, Specht J, Matukumalli L, Nelson R, Shoemaker R, Young N, Cregan P (2008) High-throughput genotyping with the GoldenGate assay in the complex genome of soybean. Theor Appl Genet 116: 945-952.
19 Mansur L M, Carriquiry A L, Rao-Arelli A P (1993) Generation mean analysis of resistance to race-3 of soybean: Icyst nematode. Crop Sci 33:1249-1253.
20 Matson A L, Williams L F (1965) Evidence of a fourth gene for resistance to the soybean cyst nematode. Crop Sci 5:477.
21 Meksem K, Doubler T W, Chancharoenchai V N, Njiti V, Chang S J C, Rao Arellj A P, Cregan P B, Gray L E, Gibson P T, Lightfoot D A (1999) Clustering among loci underlying soybean resistance to *Fusarium solani*, SDS and SCN in near-isogenic lines. Theor Appl Genet 99:1131-1142.
22 Niblack T L, Arelli P R, Noel G R, Opperman C H, Orf J H, Schmitt D P, Shannon J G, Tylka G L (2002) A revised classification scheme for genetically diverse populations of *Heterodera glycines*. J Nematol 34:279-288.
23 Rao-Arelli A P (1994) Inheritance of resistance to *Heterodera glycines* race 3 in soybean accessions. Plant Dis: 78:898-900.
24 Schapaugh W T, Owen P A, Clark K M, Sleper D A (1998) Registration of 'Magellan' soybean. Crop Sci 38:892.
25 Song Q J, Marek L F, Shoemaker R C, Lark K G, Concibido V C, Delannay X, Specht J E, Cregan P B (2004) A new integrated genetic linkage map of the soybean. Theor Appl Genet 109:122-128.
26 van Ooijen j h, Voorrips R E (2001) JoinMap 3.0 software for the calculation of genetic linkage maps. Plant Research Internation, Wageningen, the Netherlands.
27 Vooriips R E (2002) MapChart: software for the graphical presentation of the linkage maps and QTLs. J Hered 93:77-78.
28 Wang D, Arelli P R, Shoemaker R C, Diers B W (2001) Loci underlying resistance to Race 3 of soybean cyst nematode in *Glycine soja* plant introduction 468916. Theor Appl Genet 103:561-566.
29 Webb D M, Baltazar B M, Rao-Arelli P A, Schupp J, Clayton K, Keim P, Beavis W D (1995) Genetic mapping of soybean cyst nematode race-3 resistance loci in soybean PI 437654. Theor Appl Genet 91:574-581.
30 Winter S M J, Shelp B J, Anderson T R, Welacky T W, Rajcan 1 (2007) QTL associated with horizontal resistance to soybean cyst nematode in *Glycine soja* P1464925B. Theor Appl Genet 114:461-472.
31 Wu X, Blake S, Sleper D A, Shannon J G, Cregan P, Nguyen H T (2008) QTL, additive, and epistatic effects for SCN resistance in PI 437654. Theor Appl Genet (accepted).
32 Xie M, Arelli P R, Sleper D A (1998) Genetic relationships among soybean plant introductions with resistance to *Heterodera glycines* using RFLP's Soybean Genetics Newsletter 25:157-163.
33 Young L D (1995) Soybean germplasm resistant to race 3, 5, and 14 of soybean cyst nematode. Crop Sci: 35:895-896.
34 Young L D (1998) *Heterodera glycines* populations selected for reproduction on Hartwig soybean. J Nematol 30:523
35 Yue P, Sleper D A, Arelli P R (2001a) Mapping resistance to multiple races of *Heterodera glycines* in soybean PI 89772 Crop Sci 41:1589-95.

SEQUENCE LISTING

The patent contains a lengthy "Sequence Listing" section. A copy of the "Sequence Listing" is available in electronic form from the USPTO web site (http://seqdata.uspto.gov/?pageRequest=docDetail&DocID=US08692064B2). An electronic copy of the "Sequence Listing" will also be available from the USPTO upon request and payment of the fee set forth in 37 CFR 1.19(b)(3).

We claim:

1. A method for generating a transgenic plant using a host plant, said transgenic plant being more resistant to soybean cyst nematode (SCN) when compared to the host plant, said method comprising a step of introducing at least one transgene into said host plant, said at least one transgene being located within the chromosomal region as defined by one QTL selected from the group consisting of SCN QTL 1-11.

2. A method for generating a new soybean cyst nematode (SCN) resistant plant by crossing two parental strains, said new plant being more resistant to SCN than at least one of the two parental strains, said method comprising a step of introducing a genomic region into said new plant through the crossing, said genomic region being the chromosomal region of claim 1 containing the transgene.

3. The method of claim 2, wherein the genomic region comprises less than 100,000 nucleotides.

4. The method of claim 2, wherein the genomic region comprises less than 10,000 nucleotides.

5. A method for generating a soybean plant, said method comprising (a) introgressing SCN resistance into an SCN sensitive soybean germplasm, (b) determining the presence or absence of a marker gene or a fragment thereof and a transgene, said marker gene being selected from the group consisting of the polynucleotide molecules of SEQ ID Nos. 1-22 and said transgene being the transgene of claim 1, and (c) allowing the germplasm generated in (a) to develop into a soybean plant resistant to soybean cyst nematode (SCN) if the marker and transgene are present, wherein step (a) precedes step (b).

6. The method of claim 5, wherein the soybean plant is generated through one or more crosses of two or more parental soybean plants.

7. The method of claim 5, wherein the presence or absence of the marker gene is determined by using DNA hybridization.

8. The method of claim 5, wherein the presence or absence of the marker gene is determined by using DNA polymerase chain reaction (PCR).

* * * * *